US007553641B2

(12) United States Patent
Rathjen et al.

(10) Patent No.: US 7,553,641 B2
(45) Date of Patent: *Jun. 30, 2009

(54) TUMOUR NECROSIS FACTOR BINDING LIGANDS

(75) Inventors: Deborah A. Rathjen, Flagstaff Hill (AU); Roger Aston, Gloucester (GB)

(73) Assignee: Arana Therapeutics Limited, Macquarie Park (AU)

( * ) Notice: Subject to any disclaimer, the term of this patent is extended or adjusted under 35 U.S.C. 154(b) by 0 days.

This patent is subject to a terminal disclaimer.

(21) Appl. No.: 11/759,787

(22) Filed: Jun. 7, 2007

(65) Prior Publication Data

US 2007/0287177 A1    Dec. 13, 2007

Related U.S. Application Data

(63) Continuation of application No. 11/326,996, filed on Jan. 5, 2006, which is a continuation of application No. 10/702,681, filed on Nov. 5, 2003, now abandoned, which is a continuation of application No. 10/453,176, filed on Jun. 2, 2003, now abandoned, which is a continuation of application No. 10/359,934, filed on Feb. 7, 2003, now abandoned, which is a continuation of application No. 10/327,541, filed on Dec. 20, 2002, now abandoned, which is a continuation of application No. 10/265,451, filed on Oct. 3, 2002, now abandoned, which is a continuation of application No. 09/736,630, filed on Dec. 13, 2000, now Pat. No. 6,593,458, which is a continuation of application No. 09/364,039, filed on Jul. 30, 1999, now Pat. No. 6,416,757, which is a continuation of application No. 08/823,893, filed on Mar. 17, 1997, now Pat. No. 5,959,087, which is a continuation of application No. 08/344,133, filed on Nov. 23, 1994, now Pat. No. 5,644,034, which is a continuation-in-part of application No. 07/828,956, filed as application No. PCT/AU90/00337 on Aug. 7, 1990, now abandoned.

(30) Foreign Application Priority Data

Aug. 7, 1989 (AU) ........................ PJ5662
Nov. 24, 1989 (AU) ........................ PJ7576

(51) Int. Cl.
*C12N 5/10* (2006.01)
*A61K 48/00* (2006.01)

(52) U.S. Cl. .................... 435/70.21; 424/93.1
(58) Field of Classification Search ........................ None
See application file for complete search history.

(56) References Cited

U.S. PATENT DOCUMENTS

| | | | |
|---|---|---|---|
| 4,603,106 A | 7/1986 | Cerami et al. |
| 4,816,567 A | 3/1989 | Cabilly et al. |
| 4,822,776 A | 4/1989 | Cerami et al. |
| 4,833,092 A | 5/1989 | Geysen |
| 4,863,727 A | 9/1989 | Zimmerman et al. |
| 4,870,163 A | 9/1989 | Rubin et al. |
| 5,075,236 A | 12/1991 | Yone et al. |
| 5,183,657 A | 2/1993 | Buurman |
| 5,194,392 A | 3/1993 | Geysen |
| 5,223,395 A | 6/1993 | Gero |
| 5,225,539 A | 7/1993 | Winter |
| 5,231,024 A | 7/1993 | Moeller et al. |
| 5,237,024 A | 8/1993 | Allberry et al. |
| 5,342,613 A | 8/1994 | Creaven et al. |
| 5,360,716 A | 11/1994 | Ohmoto et al. |
| 5,395,760 A | 3/1995 | Smith et al. |
| 5,436,154 A | 7/1995 | Barbanti et al. |
| 5,506,265 A | 4/1996 | Blitstein-Willinger |
| 5,530,101 A | 6/1996 | Queen et al. |
| 5,539,084 A | 7/1996 | Geysen |
| 5,585,089 A | 12/1996 | Queen et al. |

(Continued)

FOREIGN PATENT DOCUMENTS

AU         89902/82 A1     4/1983

(Continued)

OTHER PUBLICATIONS

Owens et al., Journal of Immunological Methods, 1994, 168: 149-165.*
Opposition file history of European Patent Application No. 90911467.0, Opposition No. 2116, Publication No. 0 486 526, (Feb. 24, 1997-Jan. 26, 2001), pp. 1-373.
Appeal file history against the Decision of Opposition Division of European Patent Office dated Nov. 11, 1999, of Application No. 90911467.0, Opposition No. 2116, Publication No. 0 486 526, Appeal Proceedings No. T0129/00-334 (Jan. 24, 2000-Sep. 13, 2000), pp. 1-62.
Opposition documents: English Translation of BASF's Opposition dated Feb. 24, 1997.
Opposition documents: English Translation of BASF's Submission dated May 29, 1998.
Opposition documents: English Translation of BASF's Submission dated Aug. 30, 1999.

(Continued)

*Primary Examiner*—Ilia Ouspenski
(74) *Attorney, Agent, or Firm*—Morrison & Foerster LLP

(57) ABSTRACT

The present invention relates to cell lines that produce ligands that bind to human tumor necrosis factor alpha (TNF) in a manner such that upon binding of these ligands to TNF the biological activity of TNF is modified. In preferred forms cell lines produce ligands that bind to TNF in a manner such that the induction of endothelial procoagulant activity of the TNF is inhibited; the binding of TNF to receptors on endothelial cells is inhibited; the induction of fibrin deposition in the tumor and tumor regression activities of the TNF are enhanced; and the cytotoxicity and receptor binding activities of the TNF are unaffected or enhanced on tumor cells. The ligand is preferably an antibody, F(ab) fragment, single domain antibody (dABs), single chain antibody or a serum binding protein. It is preferred, however, that the ligand is a monoclonal antibody or F(ab) fragment thereof.

188 Claims, 28 Drawing Sheets

U.S. PATENT DOCUMENTS

| | | | |
|---|---|---|---|
| 5,595,915 A | 1/1997 | Geysen | |
| 5,605,690 A | 2/1997 | Jacobs et al. | |
| 5,644,034 A | 7/1997 | Rathjen et al. | |
| 5,654,407 A | 8/1997 | Boyle et al. | |
| 5,656,272 A | 8/1997 | Le et al. | |
| 5,658,570 A | 8/1997 | Newman et al. | |
| 5,658,803 A | 8/1997 | Kuo | |
| 5,672,347 A | 9/1997 | Aggarwal et al. | |
| 5,693,761 A | 12/1997 | Queen et al. | |
| 5,693,762 A | 12/1997 | Queen et al. | |
| 5,698,195 A | 12/1997 | Le et al. | |
| 5,698,419 A | 12/1997 | Wolpe et al. | |
| 5,700,788 A | 12/1997 | Mongelli et al. | |
| 5,712,155 A | 1/1998 | Smith et al. | |
| 5,730,975 A | 3/1998 | Hotamisligil et al. | |
| 5,741,488 A | 4/1998 | Feldman et al. | |
| 5,750,105 A | 5/1998 | Newman et al. | |
| 5,776,947 A | 7/1998 | Kroemer et al. | |
| 5,782,792 A | 7/1998 | Jones et al. | |
| 5,795,967 A | 8/1998 | Aggarwal et al. | |
| 5,808,029 A | 9/1998 | Brockhaus et al. | |
| 5,872,210 A | 2/1999 | Medabalimi | |
| 5,888,511 A | 3/1999 | Skurkovich et al. | |
| 5,919,452 A | 7/1999 | Le et al. | |
| 5,958,413 A | 9/1999 | Anagnostopulos et al. | |
| 5,959,087 A | 9/1999 | Rathjen et al. | |
| 5,993,833 A | 11/1999 | De Lacharriere et al. | |
| 5,994,510 A | 11/1999 | Adair et al. | |
| 5,998,577 A | 12/1999 | Geysen | |
| 6,015,558 A | 1/2000 | Hotamisligil et al. | |
| RE36,755 E | 6/2000 | Smith et al. | |
| 6,090,382 A | 7/2000 | Salfeld et al. | |
| 6,172,202 B1 | 1/2001 | Marcucci et al. | |
| 6,180,370 B1 | 1/2001 | Queen et al. | |
| 6,190,691 B1 | 2/2001 | Mak | |
| 6,194,451 B1 | 2/2001 | Alpegiani et al. | |
| 6,201,105 B1 | 3/2001 | Smith et al. | |
| 6,258,562 B1 | 7/2001 | Salfeld et al. | |
| 6,277,969 B1 | 8/2001 | Le et al. | |
| 6,284,471 B1 | 9/2001 | Le et al. | |
| 6,309,640 B1 | 10/2001 | Cerami et al. | |
| 6,358,920 B1 | 3/2002 | Blaschuk et al. | |
| 6,416,757 B1 | 7/2002 | Rathjen et al. | |
| 6,417,158 B1 | 7/2002 | Hauptmann et al. | |
| 6,419,927 B1 | 7/2002 | Cerami et al. | |
| 6,419,944 B2 | 7/2002 | Tobinick | |
| 6,448,380 B2 | 9/2002 | Rathjen et al. | |
| 6,451,983 B2 | 9/2002 | Rathjen et al. | |
| 6,498,237 B2 | 12/2002 | Rathjen et al. | |
| 6,509,015 B1 | 1/2003 | Salfeld et al. | |
| 6,548,640 B1 | 4/2003 | Winter | |
| 6,569,996 B1 | 5/2003 | Blaschuk et al. | |
| 6,572,852 B2 | 6/2003 | Smith et al. | |
| 6,593,458 B1 | 7/2003 | Rathjen et al. | |
| 2001/0021513 A1 | 9/2001 | Puijk et al. | |
| 2002/0010180 A1 | 1/2002 | Feldmann et al. | |
| 2003/0049256 A1 | 3/2003 | Tobinick | |
| 2003/0135029 A1 | 7/2003 | Rathjen et al. | |
| 2003/0139577 A1 | 7/2003 | Rathjen et al. | |
| 2003/0139580 A1 | 7/2003 | Rathjen et al. | |
| 2003/0162948 A1 | 8/2003 | Rathjen et al. | |
| 2003/0166874 A1 | 9/2003 | Rathjen et al. | |
| 2003/0170204 A1 | 9/2003 | Rathjen et al. | |
| 2003/0171553 A1 | 9/2003 | Rathjen et al. | |
| 2003/0171554 A1 | 9/2003 | Rathjen et al. | |
| 2003/0171555 A1 | 9/2003 | Rathjen et al. | |
| 2003/0199678 A1 | 10/2003 | Rathjen et al. | |
| 2003/0208047 A1 | 11/2003 | Rathjen et al. | |
| 2003/0208049 A1 | 11/2003 | Rathjen et al. | |
| 2003/0216552 A1 | 11/2003 | Rathjen et al. | |
| 2003/0225254 A1 | 12/2003 | Rathjen et al. | |
| 2003/0228605 A1 | 12/2003 | Slootstra et al. | |
| 2003/0232970 A1 | 12/2003 | Rathjen et al. | |
| 2003/0232971 A1 | 12/2003 | Rathjen et al. | |
| 2004/0002588 A1 | 1/2004 | Rathjen et al. | |
| 2004/0002589 A1 | 1/2004 | Rathjen et al. | |
| 2004/0002590 A1 | 1/2004 | Rathjen et al. | |
| 2004/0014227 A1 | 1/2004 | Frederick et al. | |
| 2004/0092721 A1 | 5/2004 | Rathjen et al. | |
| 2004/0126376 A1 | 7/2004 | Rathjen et al. | |
| 2004/0214993 A2 | 10/2004 | Rathjen et al. | |
| 2006/0140951 A1 | 6/2006 | Rathjen et al. | |
| 2006/0140952 A1 | 6/2006 | Rathjen et al. | |
| 2006/0159677 A1 | 7/2006 | Rathjen et al. | |
| 2006/0182746 A1 | 8/2006 | Rathjen et al. | |
| 2006/0204499 A1 | 9/2006 | Rathjen et al. | |
| 2006/0233802 A1 | 10/2006 | Rathjen et al. | |
| 2007/0065426 A1 | 3/2007 | Rathjen et al. | |
| 2007/0077248 A1 | 4/2007 | Rathjen et al. | |
| 2007/0280932 A1 | 12/2007 | Rathjen et al. | |
| 2008/0234469 A1 | 9/2008 | Rathjen et al. | |

FOREIGN PATENT DOCUMENTS

| | | |
|---|---|---|
| AU | 61511/86 A1 | 2/1987 |
| AU | 31252/89 | 9/1989 |
| AU | 72626/91 | 5/1991 |
| EP | 0 101 681 A1 | 3/1983 |
| EP | 0 101 681 B1 | 3/1983 |
| EP | 0 138 855 A1 | 5/1985 |
| EP | 0 138 855 B1 | 5/1985 |
| EP | 0 138 855 B2 | 5/1985 |
| EP | 0 186 833 A2 | 7/1986 |
| EP | 0 186 833 A3 | 7/1986 |
| EP | 0 186 833 B1 | 7/1986 |
| EP | 0 212 489 A2 | 3/1987 |
| EP | 0 212 489 A3 | 3/1987 |
| EP | 0 212 489 B1 | 3/1987 |
| EP | 0 218 868 A2 | 4/1987 |
| EP | 0 218 868 A3 | 4/1987 |
| EP | 0 239 400 A2 | 9/1987 |
| EP | 0 239 400 A3 | 9/1987 |
| EP | 0 239 400 B1 | 9/1987 |
| EP | 0 260 610 A2 | 3/1988 |
| EP | 0 260 610 A3 | 3/1988 |
| EP | 0 260 610 B1 | 3/1988 |
| EP | 0 288 088 A2 | 10/1988 |
| EP | 0 288 088 A3 | 10/1988 |
| EP | 0 288 088 B1 | 10/1988 |
| EP | 0 308 378 A2 | 3/1989 |
| EP | 0 308 378 A3 | 3/1989 |
| EP | 0 308 378 B1 | 3/1989 |
| EP | 0 323 806 A1 | 7/1989 |
| EP | 0 323 806 B1 | 7/1989 |
| EP | 0 350 690 A2 | 1/1990 |
| EP | 0 350 690 A3 | 1/1990 |
| EP | 0 351 789 A2 | 1/1990 |
| EP | 0 351 789 A3 | 1/1990 |
| EP | 0 351 789 B1 | 1/1990 |
| EP | 0 366 043 A1 | 5/1990 |
| EP | 0 366 043 B1 | 5/1990 |
| EP | 0 380 068 A1 | 8/1990 |
| EP | 0 380 068 B1 | 8/1990 |
| EP | 0 393 438 A2 | 10/1990 |
| EP | 0 393 438 A3 | 10/1990 |
| EP | 0 393 438 B1 | 10/1990 |
| EP | 0 398 327 A1 | 11/1990 |
| EP | 0 398 327 B1 | 11/1990 |
| EP | 0 412 486 A1 | 2/1991 |
| EP | 0 412 486 B1 | 2/1991 |
| EP | 0 433 900 A1 | 6/1991 |
| EP | 0 433 900 B1 | 6/1991 |
| EP | 0 415 216 B1 | 10/1991 |
| EP | 0 451 216 A1 | 10/1991 |

| | | |
|---|---|---|
| EP | 0 453 898 A2 | 10/1991 |
| EP | 0 453 898 A3 | 10/1991 |
| EP | 0 453 898 B1 | 10/1991 |
| EP | 0 486 526 A1 | 5/1992 |
| EP | 0 486 526 B1 | 5/1992 |
| EP | 0 486 526 B2 | 5/1992 |
| EP | 0 512 528 A2 | 11/1992 |
| EP | 0 512 528 A3 | 11/1992 |
| EP | 0 512 528 B1 | 11/1992 |
| EP | 0 526 905 A2 | 2/1993 |
| EP | 0 526 905 A3 | 2/1993 |
| EP | 0 526 905 B1 | 2/1993 |
| EP | 0 566 647 A1 | 10/1993 |
| EP | 0 566 647 B1 | 10/1993 |
| EP | 0 585 705 A1 | 3/1994 |
| EP | 0 585 705 B1 | 3/1994 |
| EP | 0 610 201 A1 | 8/1994 |
| EP | 0 610 201 B1 | 8/1994 |
| EP | 0 614 984 A2 | 9/1994 |
| EP | 0 614 984 A3 | 9/1994 |
| EP | 0 614 984 B1 | 9/1994 |
| EP | 0 663 836 A1 | 7/1995 |
| EP | 0 663 836 B1 | 7/1995 |
| EP | 0 682 040 A1 | 11/1995 |
| EP | 0 682 040 B1 | 11/1995 |
| EP | 0 706 795 A2 | 4/1996 |
| EP | 0 706 795 A3 | 4/1996 |
| EP | 0 861 850 A1 | 9/1998 |
| EP | 0 861 850 B1 | 9/1998 |
| EP | 0 867 509 A2 | 9/1998 |
| EP | 0 867 509 A3 | 9/1998 |
| EP | 0 867 509 B1 | 9/1998 |
| EP | 0 869 179 A1 | 10/1998 |
| EP | 0 870 827 A2 | 10/1998 |
| EP | 0 870 827 A3 | 10/1998 |
| EP | 0 870 827 B1 | 10/1998 |
| EP | 1 097 945 A2 | 5/2001 |
| EP | 1 097 945 A3 | 5/2001 |
| GB | 2188638 A | 10/1987 |
| GB | 2188638 B | 10/1987 |
| JP | 61-047500 A | 3/1986 |
| JP | 63-093799 A | 4/1988 |
| JP | 1-268645 A | 10/1989 |
| JP | 02-227095 A | 9/1990 |
| WO | WO-84/03564 A1 | 9/1984 |
| WO | WO-87/03489 A1 | 6/1987 |
| WO | WO-88/02632 A1 | 4/1988 |
| WO | WO-89/08460 A1 | 9/1989 |
| WO | WO-89/09610 A1 | 10/1989 |
| WO | WO-90/00400 A1 | 1/1990 |
| WO | WO-90/00902 A1 | 2/1990 |
| WO | WO-90/01950 A1 | 3/1990 |
| WO | WO-90/06514 A1 | 6/1990 |
| WO | WO-91/02078 A1 | 2/1991 |
| WO | WO-91/04054 A1 | 4/1991 |
| WO | WO-91/09967 A1 | 7/1991 |
| WO | WO-92/01047 A1 | 1/1992 |
| WO | WO-92/01059 A1 | 1/1992 |
| WO | WO-92/01472 A1 | 2/1992 |
| WO | WO-92/02190 A1 | 2/1992 |
| WO | WO-92/07076 A1 | 4/1992 |
| WO | WO-92/11383 A1 | 7/1992 |
| WO | WO-92/13095 A1 | 8/1992 |
| WO | WO-92/16553 A1 | 10/1992 |
| WO | WO-93/02108 A1 | 2/1993 |
| WO | WO-93/06213 A1 | 4/1993 |
| WO | WO-93/09872 A1 | 5/1993 |
| WO | WO-93/11236 A1 | 6/1993 |
| WO | WO-94/08609 A1 | 4/1994 |
| WO | WO-94/08619 A1 | 4/1994 |
| WO | WO-98/51344 A1 | 11/1998 |
| WO | WO-00/29851 A1 | 5/2000 |
| WO | WO-00/62790 A2 | 10/2000 |
| WO | WO-00/62790 A3 | 10/2000 |
| WO | WO-01/60769 A1 | 8/2001 |
| WO | WO-02/31510 A1 | 4/2002 |
| WO | WO-02/066984 A2 | 8/2002 |
| WO | WO-02/066984 A3 | 8/2002 |
| WO | WO-03/010536 A2 | 2/2003 |
| WO | WO-03/010536 A3 | 2/2003 |
| WO | WO-2004/039962 A2 | 5/2004 |
| WO | WO-2004/077062 A2 | 9/2004 |
| WO | WO-2004/077062 A3 | 9/2004 |
| WO | WO-2004/077062 B1 | 9/2004 |

OTHER PUBLICATIONS

Opposition documents: English Translation of BASF's Statement of Grounds of Appeal dated May 29, 2000.

Opposition documents: English Translation of BASF's Request for Restitutio in Integrum dated Jun. 5, 2000.

Aaskov, J.G. et al. (1989). "Serologically Defined Linear Epitopes in the Envelope Protein of Dengue 2 (Jamaica Strain 1409)," *Arch. Virol.* 105(3-4):209-221.

Abbas, A.K. et al. (2003). Schematic Diagram of a Secreted IgC Molecule *In Cellular and Molecular Immunology* Fifth Edition, Saunders, Elsevier: USA, one page.

Aderka, D. (1991). "Role of Tumor Necrosis Factor in the Pathogenesis of Intravascular Coagulopathy of Sepsis: Potential New Therapeutic Implications," *Isr. J. Med. Sci.* 27:52-60.

Aderka, D. et al. (1989). "IL-6 Inhibits Lipopolysaccharide-Induced Tumor Necrosis Factor Production in Cultured Human Monocytes, U937 Cells, and in Mice," *J. Immunol.* 143(11):3517-3523.

Aderka, D. et al. (1992). "The Possible Role of Tumor Necrosis Factor (TNF) and Its Natural Inhibitors, The Soluble-TNF Receptors, In Autoimmune Diseases," *Israel J. Med. Sci..* 28:126-130.

Aggarwal, B. et al. (1985). "Human Tumor Necrosis Factor. Production, Purification, and Characterization," *J. Biol. Chem.* 260(4):2345-2354.

Aggarwal, B.B. et al. (Dec. 1985). "Characterization of Receptors For Human Tumour Necrosis Factor and Their Regulation by $^{\gamma}$-Interferon," *Nature* 318:665-667.

Aggarwal, B.B. et al. eds. (1992). *Tumor Necrosis Factors: Structure, Function, and Mechanism of Action* Marcel Dekker, Inc. NY pp. ix-xi. (Table of Contents Only.).

Akama, H. et al. (1990). "Mononuclear Cells Enhance Prostaglandin $E_2$ Production of Polymorponuclear Leukocytes Via Tumor Necrosis Factor α," *Biochemical and Biophysical Research Communications* 168(2):857-862.

Alberts, B. et al. (1983). "How Cells Are Studied" Chapter 4 *In Molecular Biology of the Cell* Garland Publishing, Inc. pp. 182-183.

Alexander, H. et al. (Apr. 1992). "Altering the Antigencity of Proteins," *Proc. Natl. Acad. Sci. USA* 89:3352-3356.

Alonso-Whipple, C. et al. (Oct. 1988). "Epitope Mapping of Human Luteinizing Hormone Using Monoclonal Antibodies," *Endocrinology* 123(4):1854-1860.

Alzani, R. et al. (1995). "Mechanism of Suramin-Induced Deoligomerization of Tumor Necrosis Factor β," *Biochemistry* 34(19):6344-6350.

Ameloot, P. et al. (2001). "Identification of Tumor Necrosis Factor (TNF) Amino Acids Crucial for Binding to the Murine p75 TNF Receptor and Construction of Receptor-selective Mutants," *J. Biol. Chem.* 276(40):37426-37430.

American Thoracic Society, Centers for Disease Control and Prevention (2000). "Targeted Tuberculin Testing and Treatment of Latent Tuberculosis Infection," *Am J. Respir. Crit. Care Med.* 161:S221-S247.

Amit, A.G. et al. (1986). "Three-Dimensional Structure of an Antigen-Antibody Complex at 2.8 A Resolution," *Science* 233(4765):747-753.

Anonymous. (Jan. 1992). "Characterization of Antipeptide Antibodies," *Chiron Pinnacles* 2(1):1-12.

Anonymous. (Apr. 1992). "Quantitative Peptide Hormone Receptor Studies on Extensive Analog Sets," *Chiron Pinnacles* 2(2):1-12.

Anonymous. (Jan. 1993). "Using Antigen Competition to Identify Sequential (Linear) Epitopes," *Chiron Pinpoints* 3(2):1-4.

Anonymous. (Sep. 1993). "Mapping Antibody-Defined Linear Epitopes," *Chiron Pinpoints* pp. 1-8.

Anonymous. (1997). "New Monoclonal Antibody Effective Treatment for Crohn's Disease Therapy," *Doctor's Guide* located at <http://www.main.pslgroup.com> last visited Jan. 20, 2003, three pages.

Anonymous. (2004). "Antibodies Can Bind Linear Peptides That Represent Adjacent Amino Acids That Form a Part of the Epitope, Though Real Linear Peptides That Represent a Complete Epitope are Rare." Quote from *Open Biosystems: Antibody Services* located at <http://www.openbiosystems.com/pepscanpeptidearrays.php> last visited on Oct. 19, 2004, one page.

Anonymous. (2004). "In Fact, Linear and Simple Discontinous Epitopes Form a Small Portion of Most Epitopes. In Most Cases, The Amino Acids That Make up Epitopes are Located on Different Strands for the Protein. These Epitopes, Known as the Discontinuous Scattered Type, are Difficult to Map. Strategies That are Being Used to Map These Produce Useful Data Only When the Structure and Conformation of the Protein is Known." Quote from *Open Biosystems: Antibody Services* located at <http://www.openbiosystems.com/pepscanpeptidearrays.php> last visited on Oct. 19, 2004, one page.

Arend, W.P. (2002). "The Mode of Action of Cytokine Inhibitors," *J. Rheumatol.* 29(S65):16-21.

Arendt, A. et al. (1993) "Optimization of Peptide Synthesis on Polyethylene Rods," *Pept. Res.* 6(6):346-352.

Arnason, B. (1999). "TNF Neutralization in MS: Results of a Randomized, Placebo-Controlled Multicenter Study," *Neurology* 53:457-465.

Aston, R. et al. (1985). "Monoclonal Antibodies to Growth Hormone and Prolactin," *Pharmac. Therapeut.* 27:403-424.

Aston, R. et al. (1989). "Antibody-Mediated Enhancement of Hormone Activity," *Mol. Immunol.* 26(5):435-446.

Atassi, M.Z. (Nov. 15, 1984). "Antigenic Structures of Proteins: Their Determination Has Revealed Important Aspects of Immune Recognition and Generated Strategies for Synthetic Mimicking of Protein Binding Sites," *FEBS Eur J Biochem.* 145(1):1-20.

Atherton, E. et al. (1975). "Polyamide Supports for Polypeptide Synthesis," *Journal of the American Chemical Society* 97(22):6584-6585.

Atherton, E. et al. (1978). "A Mild Procedure for Solid Phase Peptide Synthesis: Use of Fluorenylmethozycarbonylamino-acids," *J.C.S. Chem. Comm.* pp. 537-539.

Aujame, L. et al. (1997). "High Affinity Human Antibodies by Phage Display," *Human Antibodies* 8(4):155-168.

Austgulen, R. et al. (1987). "Fibroblast Growth-Stimulatory Activity Released from Human Monocytes," *Scand. J. Immunol.* 26:621-629.

Avrameas, S. et al. (1971). "Communication to the Editors: Peroxidase Labelled Antibody and Fab Conjugates with Enhanced Intracellular Penetration," *Immunochemistry* 8:1175-1179.

Banner, D.W. et al. (1993). "Crystal Structure of the Soluble Human 55 kd TNF Receptor-Human TNFβ Complex: Implications for TNF Receptor Activiation," *Cell* 73:431-445.

Barbanti, E. et al. (1991). "A High-Affinity Neutralizing Anti-Human TNF-Alpha Monoclonal Antibody That Cross-Reacts with Human TNF-Beta," *2nd International Congress on the Immune Consequences of Trauma, Shock and Sepsis Mechanisms and Therapeutic Approaches* Munich Germany (Mar. 6-9, 1991) Abstract No. OR 37, one page.

Barbas, C.F. III et al. (1993). "High Affinity Self-Reactive Human Antibodies by Design and Selection: Targeting the Integrin Ligand Binding Site," *Proc. Natl. Acad. Sci. USA* 90:10003-10007.

Barbas, C.F. III et al. (1994). "In vitro Evolution of a Neutralizing Human Antibody to Human Immunodeficiency Virus Type 1 to Enhance Affinity and Broaden Strain Cross-Reactivity," *Proc. Natl. Acad. Sci. USA* 91:3809-3813.

Barbuto, J.A.M. et al. (1993). "Production of Neutralizing Antibodies to Tumor Necrosis Factor by Human Tumor-Infiltrating B Lymphocytes," *Proceedings of the 84th Annual Meeting of theAmerican Association For Cancer Research* (May 19-22, 1993) Orlando, FL. 34:487 Abstract 2904.

Bard, F. et al. (2000). "Peripherally Administered Antibodies Against Amyloid B-Peptide Enter the Central Nervous System and Reduce Pathology in a Mouse Model or Alzheimer Disease," *Nature Medicine* 6(8):916-919.

Barlow, D.J. et al. (Aug. 21, 1986). "Continuous and Discontinuous Protein Antigenic Determinants," *Nature* 322:747-748.

Bates, E.J. et al. (Jul. 1995). "Inhibitory Effects of Arachidonic Acid ($20:4_1$n-6) and its Monohydroperoxy- and Hydroxy-Metabolites on Procoagulant Activity in Endothelial Cells," *Atherosclerosis* 116:125-133.

Bazzoni, F. et al. (1995). "How Do Tumor Necrosis Factor Receptors Work," *J. Inflamm.* 45:221-238.

Bazzoni, F. et al. (1996). "Seminars in Medicine of the Beth Isreal Hospital; Boston: The Tumor Necrosis Factor Ligand and Receptor Families," *New England Journal of Medicine Flier*, J.S. et al. eds., 334(26):1717-1725.

Beck, J. et al. (1987). "Increased Production of TNF-α in Multiple Sclerosis," Abstract D.2., *Immunobiology* 175(1/2):91-92.

Beck, J. et al. (1988). "Increased Production of Interferon Gamma and Tumor Necrosis Factor Precedes Clinical Manifestation in Multiple Sclerosis: Do Cytokines Trigger Off Exacerbations," *Acta. Neurol. Scand.* 78:318-323.

Bendtzen, K. et al. (1989). "Native Inhibitors (Autoantibodies) of IL-1α and TNF," *Immunolgy Today* 10(7):222.

Bendtzen, K. et al. (1990). "Auto-Antibodies to IL-1α and TNFα In Normal Individuals and In Infectious and Immunoinflammatory Disorders," *In The Physiological and Pathological Effects of Cytokines*, Wiley-Liss, Inc. 10B:447-452.

Berkow, R.L. et al. (Dec. 1, 1987). "Enhancement of Neutrophil Superoxide Production by Preincubation with Recombinant Human Tumor Necrosis Factor," *J. Immunology* 139(11):3783-3791.

Bernstein, C.N. et al. (2001). "Cancer Risk in Patients with Inflammatory Bowel Disease," *Cancer* 91:854-862.

Bès, C. et al. (Apr. 18, 2003). "Mapping the Paratope of Anti-CD4 Recombinant Fab 13B8.2 by Combining Parallel Peptide Synthesis and Site-Directed Mutagenesis," *The J. of Biol. Chem.* 278(16):14265-14273.

Beutler, B. et al. (1985). "Identity of Tumour Necrosis Factor and the Macrophage-Secreted Factor Cachetin," *Nature* 316:552-554.

Beutler, B. et al. (1985). "Passive Immunization Against Cachectin/Tumor Necrosis Factor Protects Mice from Lethal Effect of Endotoxin," *Science* 229:869-871.

Beutler, B. et al. (1985). "Purification of Cachectin, A Lipoprotein Lipase-Suppressing Hormon Secreted by Endotoxin-Induced Raw 264.7 Cells," *J. Exp. Med.* 161:984-995.

Beutler, B. et al. (1986). "Cachectin and Tumour Necrosis Factor as Two Sides of the Same Biological Coin," *Nature* 320:584-588.

Beutler, B. et al. (1989). "The Biology of Cachetctin/TNF—A Primary Mediator of the Host Response," *Ann. Rev. Immunol.* 7:625-655.

Bevilacqua, M.P. et al. (Jun. 1986). "Recombinant Tumor Necrosis Factor Induces Procoagulant Activity in Cultured Human Vascular Endothelium: Characterization and Comparison with the Actions of Interleukin 1," *Proc. Natl. Acad. Sci. USA Medical Sciences* 83:4533-4537.

Bhardwaj, V. et al. (Aug. 1992). "Subjugation of Dominant Immunogenic Determinants Within a Chimeric Peptide," *Eur. J. Immunol.* 22(8):2009-2016.

Bittorf, T. (2000). "cDNA Cloning and Functional Analysis of a Truncated STAT5a Protein from Autonomously Growing FDCP-1 Cells," *Cell Signal* 12:721-730.

Bloom, J.W. et al. (Sep. 1, 1993). "Epitope Mapping and Functional Analysis of Three Murine IgG1 Monoclonal Antibodies to Human Tumor Necrosis Factor-α," *J. Immunol.* 151(5):2707-2716.

Blundell, T. et al. (1988). "Knowledge-Based Protein Modelling and Design," *Eur. J. Biochem.* 172:513-520.

Bodmer, J.-L. et al. (Jan. 2002). "The Molecular Architecture of the TNF Superfamily," *Trends Biochem Sci.* 27(1):19-26.

Boekstegers, P. et al. (1994). "Changes in Skeletal Muscle $PO_2$, After Administration of Anti-TNFα-Antibody in Patients With Severe Sepsis: Comparison to Interleukin-6 Serum Levels, Apache II, and Elebute Scores," *Shock* 1:246-253.

Borras, E. et al. (2002). "Findings on T Cell Specificity Revealed by Synthetic Combinatorial Libraries," *Journal of Immunological Methods* 267:79-97.

Borrebaeck, C.A.K. ed. (1995). *Antibody Engineering* Second Edition, Oxford University Press, p. 291.

Boulianne, G.L. et al. (Dec. 13-19, 1984). "Production of Functional Chimaeric Mouse/Human Antibody," *Nature* 312(5995):643-646.

Boyle, P. et al. (1993). "A Novel Monoclonal Human IgM Autoantibody Which Binds Recombinant Human and Mouse Tumor Necrosis Factor-α," *Cellular Immunology* 152:556-568.

Boyle, P. et al. (1993). "The B5 Monoclonal Human Autoantibody Binds to Cell Surface TNFα on Human Lymphoid Cells and Cell Lines and Appears to Recognize a Novel Epitope," *Cellular Immunology* 152:569-581.

Bradbury, A. et al. (1995). "The Cloning of Hybridoma V Regions for Their Ectopic Expression in Intracellular and Intercellular Immunization," Chapter 10 *In Antibody Engineering*, Borrebaeck, C.A.K. ed., IRL Press: Oxford, UK, pp. 295-361.

Braden, B.C. et al. (1995). "Structural Features of the Reactions Between Antibodies and Protein Antigens," *FASEB J.* 9:9-16.

Braden, B.C. et al. (1998). "Anatomy of an Antibody Molecule: Structure, Kinetics, Thermodynamics and Mutational Studies of the Antilysozyme Antibody D1.3," *Immunol Rev.* 163:45-57.

Brennan, F.M. et al. (1989). "Inhibitory Effect of the TNFα Antibodies on Synovial Cell Interleukin-1 Production in Rheumatoid Arthritis," *The Lancet* pp. 244-247.

Bringman, T. et al. (1987). "Monoclonal Antibodies to Human Tumor Necrosis Factors Alpha and Beta: Application for Affinity Purification, Immunoassays, and as Structural Probes," *Hybridoma* 6(5):489-507.

Briscoe, H. et al. (Oct. 2003). "A Novel Tumor Necrosis Factor (TNF) Mimetic Peptide Prevents Recrudescence of *Mycobacterium bovis* Bacillus Calmette-Guerin (BCG) Infection in CD4$^+$ T Cell-Depleted Mice," *J. Leukoc. Biol.* 68:538-544.

Britton, W.J. et al. (May 1998). "A Tumor Necrosis Factor Mimetic Peptide Activates a Murine Macrophage Cell Line to Inhibit Mycobacterial Growth in a Nitric Oxide-Dependent Fashion," *Infection and Immunity* 66(5):2122-2127.

Brockhaus, M. et al. (1990). "Identification of Two Types of Tumor Necrosis Factor Receptors on Human Cell Lines by Monoclonal Antibodies," *Proc. Nato. Sci. USA* 87:3127-3131.

Brok, H.P.M. et al. (2002). "Prevention of Experimental Autoimmune Encephalomyelitis in Common Marmosets Using an Anti-IL-12p40 Monoclonal Antibody," *J. Immunol.* pp. 6554-6563.

Bruggemann, M. et al. (1989). "The Immonocenicity of Chimeric Antibodies," *J. Exp. Med.* 170:2153-2157.

Burrows, S.R. et al. (Jan. 1992). "The Specificity of Recognition of a Cytotoxic T Lymphocyte Epitope," *Eur. J. Immunol.* 22(1):191-195.

Burton, D.R. et al. (Nov. 27, 1980). "The C1q Receptor Site on Immunoglobulin G," *Nature* 288:338-344.

Burton, D.R. et al. (1991). "A Large Array of Human Monoclonal Antibodies to Type 1 Human Immunodeficiency Virus From Combinatorial Libraries of Asymptomatic Seropositive Individuals," *Proc. Natl. Acad. Sci. USA* 88:10134-10137.

Burton, D.R. et al. (1992) "Antibodies From Libraries," *Nature* 359(6398):782-783.

Burton, D.R. et al. (1994). "Human Antibodies From Combinatorial Libraries,"*Adv. Immunol.* 57:191-280.

Carswell, E.A. et al. (Sep. 1975). "An Endotoxin-Induced Serum Factor that Causes Necrosis of Tumors," *Proc. Natl. Acad. Sci. USA* 72(9):3666-3670.

Carter, J.M. et al. (1989). "Characterization of Hardware for Peptide Synthesis using Geysen's Method, and Epitope Scanning of a Malarial Protein," *In Proc. 11$^{th}$ Amer. Peptide Symp.*, Rivier, J.E. et al. eds., ESCOM, Leiden, 721-723.

Cazaubon, S. et al. (Jun. 1989). "Monoclonal Antibodies to Protein Kinase Cγ. Functional Relationship Between Epitopes and Cofactor Binding Sites," *Eur. J. Biochem.* 182(2):401-406.

Cerami, A. et al. (1985). "Weight Loss Associated With an Endotoxin-Induced Mediator From Peritoneal Macrophages: The Role of Cachectin (Tumor Necrosis Factor)," *Immunol. Lett.* 11:173-177.

Chaudhari, U. et al. (2001). "Efficacy and Safety of Infliximab Monotherapy for Plaque-Type Psoriasis: A Randomised Trial," *Lancet* 357:1842-1847.

Chen, Y. et al. (Nov. 1999). "Selection and Analysis of an Optimized Anti-VEGF Antibody: Crystal Structure of an Affinity-Matured Fab in Complex with Antigen," *J. Mol. Biol.* 293:865-881.

Choulier, L. et al. (2001). "Delineation of a Linear Epitope by Multiple Peptide Synthesis and Phage Display," *Journal of Immunological Methods* 249:253-264.

Choulier, L. et al. (2002). "Comparative Properties of Two Peptide-Antibody Interactions as Deduced from Epitope Delineation," *J. Immunol. Methods* 259(1-2):77-86.

Clackson, T. et al. (1991). "General Applications of PCR to Gene Cloning and Manipulation" Chapter 12 *In PCR: A Practical Approach* McPherson, M.J. et al. eds., IRL Press at Oxford University Press, pp. 187-214.

Clackson, T. et al. (1991). "Making Antibody Fragments Using Phage Display Libraries," *Nature* 352:624-628.

Clark, W.R. (1991). "Types of Antibody Reactions," *In The Experimental Foundations of Modern Immunolgy*, Fourth Edition, John Wiley & Sons, Inc.: New York, NY, pp. 143-155.

Colman, P.M. (1988). "Structure of Antibody-Antigen Complexes: Implications for Immune Recognition," *Adv Immunol.* 43:99-132.

Colman, P.M. (1991). "Antigen-Antigen Receptor Interactions," *Curr. Opin. Struct. Biol.* 1:232-236.

Colman, P.M. et al. (1987). "Three-Dimensional Structure of a Complex of Antibody with Influenza Virus Neuraminidase," *Nature* 326:358-363.

Connolly, M.L. (Jun. 1993). "The Molecular Interface Package," *J. Mol. Graphics* 11:139-141.

Cook, K.M. et al. (1985). "Topographic and Functional Assay of Antigenic Determinants of Human Prolactin with Monoclonal Antibodies," *Molec. Immun.* 22(7):795-801.

Corey, E. et al. (1997). "Prostate-Specific Antigen: Characterization of Epitopes by Synthetic Peptide Mapping and Inhibition Studies," *Clin. Chemistry* 43(4):575-584.

Corti, A. et al. (1992). "Antigenic Regions of Tumor Necrosis Factor Alpha and Their Topographic Relationships with Structural/Functional Domains," *Mol. Immunol.* 29(4):471-479.

Corti, A. et al. (1992). "Oligomeric Tumour Necrosis Factor α Slowly Converts into Inactive Forms at Bioactive Levels," *Biochem. J.* 284(Pt3):905-910.

Corti, A. et al. (1993). "Evidences That Syngeneic Alpha-Type Anti-Idiotypic Antibodies May Non-Competitively Inhibit Idiotype/Oligomeric Antigen Interactions by Affecting Idiotype Avidity," *Mol. Immunol.* 30(12):1123-1131.

Costabile, M. et al. (Oct. 1, 2001). "A Novel Long Chain Polyunsaturated Fatty Acid, β-Oxa 21:3n-3, Inhibits T Lymphocyte Proliferation, Cytokine Production, Delayed-Type Hypersensitivity, and Carrageenan-Induced Paw Reaction and Selectivity Targets Intracellular Signals," *J. Immunol.* 167(7):3980-3987.

Craig, L. et al. (1998). "The Role of Structure in Antibody Cross-Reactivity Between Peptides and Folded Proteins," *J. Mol. Biol.* 281:183-201.

Crameri, A. et al. (1996). "Construction and Evolution of Antibody-Phage Libraries by DNA Shuffling," *Nature Medicine* 2(1):100-102.

Creasey, A.A. et al. (1987). "Biological Effects of Recombinant Human Tumor Necrosis Factor and Its Novel Muteins on Tumor and Normal Cell Lines," *Cancer Res.* 47:145-149.

Creaven, P.J. et al. (1991). "Response to Tumor Necrosis Factor in Two Cases of Psoriasis," *J. of the Am. Acad. Dermatol.* 24:735-737.

Cross, A.S. et al. (1989). "Pretreatment with Recombinant Murine Tumor Necrosis Factor α/Cachectin and Murine Interleukin 1 α Protects Mice From Lethal Bacterial Infection," *The Journal of Experimental Medicine* 169:2021-2027.

Dall'Acqua, W. et al. (1998). "A Mutational Analysis of Binding Interactions in an Antigen—Antibody Protein-Protein Complex," *Biochemistry* 37:7981-7991.

Damiani, G. et al. (May 1988). "Generation and Characterization of Monoclonal Antibodies to 28-, 35-, and 65-Kilodalton Proteins of *Mycobacterium tuberculosis*," *Infect Immun.* 56(5):1281-1287.

Danis, V.A. et al. (Jul. 1991). "Effects of Granulocyte-Macrophage Colony-Stimulating Factor (GM-CSF), IL-2, Interferon-Gamma (IFN-γ), Tumour Necrosis Factor-Alpha (TNF-α) and IL-6 on the Production of Immunoreactive IL-1 and TNF-α by Human Monocytes," *Clin. Exp. Immunol.* 85(1):143-150.

Danis, V.A. et al. (Aug. 1992). "Circulating Cytokine Levels in Patients with Rheumatoid Arthritis: Results of a Double Blind Trial with Sulphasalazine," *Ann Rheum.Dis.* 51(8):946-950.

Davenport, C. et al. (1992). "Stimulation of Human B Cells Specific For *Candida Albicans* For Monoclonal Antibody Production," *FEMS Microbiol. Immunol.* 86:335-343.

Davies, D.R. et al. (1990). "Antibody-Antigen Complexes," *Annu Rev Biochem.* 59:439-473.

Davies, D.R. et al. (1993). "Antibody Structure," *Acc. Chem. Res.* 26:421-427.

Davies, S.J. et al. (2004). "Involvement of TNF in Limiting Liver Pathology and Promoting Parasite Survival During Schistosome Infection," *International Journal for Parasitology* 34:27-36.

de Haard, H.J. et al. (1999). "A Large Non-Immunized Human Fab Fragment Phage Library That Permits Rapid Isolation and Kinetic Analysis of High Affinity Antibodies," *The Journal of Biological Chemistry* 274(26):18218-18230.

de Haard, H.J.W. et al. (Sep. 1998). "Selection of Recombinant, Library-Derived Antibody Fragments Against p24 for Human Immunodeficiency Virus Type 1 Diagnostics," *Clin. Diagn. Lab. Immunol.* 5(5):636-644.

Di Giovine, F. et al. (1988). "Tumour Necrosis Factor in Synovial Exudates," *Annals of the Rheumatic Diseases* 47:768-772.

Diamond, A.G. et al. (1984). "Localized Conformational Changes Induced in a Class I Major Histocompatibility Antigen by the Binding of Monoclonal Antibodies," *J. Immun.* 132(3):1169-1175.

Dionyssopoulou, H. et al. (Jul. 31, 2000). "Synthetic Peptides as Putative Therapeutic Agents in Transplantation Medicine: Application of PEPSCAN to the Identification of Functional Sequences in the Extracellular Domain of the Interleukin-2 Receptor Beta Chain (IL-2Rβ)," *J. Immunol. Methods* 241:83-95.

Dong, L. et al. (2003). "Human CD30: Structural Implications From Epitope Mapping and Modeling Studies,"*J. Mol. Recogn.* 16:28-36.

Dueñas, M. et al. (1996). "Selection of Phage Displayed Antibodies Based on Kinetic Constants," *Molecular Immunology* 33(7):279-285.

Duncan, A.R. et al. (Apr. 7, 1988). "Localization of the Binding Site for the Human High-Affinity Fc Receptor on IgG," *Nature* 332:563-564.

Duncombe, A.S. et al. (1989). "Tumor Necrosis Factor Mediates Autocrine Growth Inhibition in a Chronic Leukemia," *J. Immunol.* pp. 3828-3834.

Echtenacher, B. et al. (1990). "Requirement of Endogenous Tumor Necrosis Factor/Cachectin for Recovery from Experimental Peritonitis," *J. Immunol.* 145(11):3762-3766.

Eck, M.J. (Oct. 1990). "The Three-Dimensional Structure of Tumor Necrosis Factor (TNF-α) at 2.6 Å Resolution Dallas," *Dissertation—University of Texas Southwestern Medical Center*, Dallas, TX. pp. 1-213.

Eck, M.J. et al. (Sep. 15, 1988). "Crystallization of Trimeric Recombinant Human Tumor Necrosis Factor (Cachectin)," *J. Biol. Chem.* 263(26):12816-12819.

Eck, M.J. et al. (1989). "The Structure of Tumor Necrosis Factor-α at 2.6 Å Resolution," *J. Bio. Chem.* 264(29):17595-17605.

Eck, M.J. et al. (1992). "The Structure of Human Lymphotoxin (Tumor Necrosis Factor-β) at 1.9- Å Resolution," *The Journal of Biological Chemistry* 267(4):2119-2122.

Eck, S.L. et al. (1996). "Gene-Based Therapy" Chapter 5 In *The Pharmacological Basis of Therapeutics*, Goodman and Gilman eds. Ninth Edition, The McGraw Hill Companies pp. 77-101.

Ede, N.J. (2002). "Multiple Parallel Synthesis of Peptides on SynPhase Grafted Supports," *Journal of Immunological Methods* 267:3-11.

Edmundson, A.B. et al. (1991). "Binding of Peptides to Proteins: An Exercise in Molecular Design," *Ciba Found. Symp.* 158:213-225; Discussion pp. 225-230.

Edmundson, A.B. et al. (Jul. 1993). "Principles and Pitfalls in Designing Site-Directed Peptide Ligands," *Proteins* 16(3):246-267.

Edmundson, A.B. et al. (2001). "Binding of Synthetic Peptides by a Human Monoclonal IgM with an Unusual Combining Site Structure," *Journal of Molecular Recognition* 14:229-238.

Elliott, M.J. et al. (1993). "Treatment of Rheumatoid Arthritis with Chimeric Monoclonal Antibodies to Tumor Necrosis Factor α," *Arthritis & Rheumatism* 36(12):1681-1690.

Elliott, M.J. et al. (1994). "Randomised Double-Blind Comparison of Chimeric Monoclonal Antibody to Tumour Necrosis Factor α (cA2) versus Placebo In Rheumatoid Arthritis," *Lancet* 344:1105-1110.

Elliott, M.J. et al. (1994). "Repeated Therapy with Monoclonal Antibody to Tumour Necrosis Factor α (cA2) in Patients with Rheumatoid Arthritis," *Lancet* 344:1125-1127.

Engelmann, H. et al. (1989). "A Tumor Necrosis Factor-Binding Protein Purified to Homogeneity from Human Urine Protects Cells from Tumor Necrosis Factor Toxicity," *J. Biol. Chem.* 264(20):11974-11980.

Engelmann, H. et al. (1990). "Two Tumor Necrosis Factor-Binding Proteins Purified from Human Urine," *J. Biol. Chem.* 265(3):1531-1536.

English Abstract of Japanese Laid-Open publication 1-268645, (1989).

Espevik, T. et al. (1986). "A Highly Sensitive Cell Line, WEHI 164 Clone 13, for Measuring Cytotoxic Factor/Tumor Necrosis Factor from Human Monocytes," *J. Immunol. Methods* 95:99-105.

Ewing, C. et al. (May 1, 1990). "Antibody Activity in Ankylosing Spondylitis Sero To Two Sites on HLA B27.1 at the MHC Groove Region (Within Sequence 65-85), and to a Klebsiella Pneumoniae Nitrogenase Reductase Peptide (Within Sequence 181-199)," *J. Exp. Med.* 171(5):1635-1647.

Exley, A.R. et al. (1989). "Monoclonal Antibody (Mab) to Recombinant Human Tumour Necrosis Factor (rhTHNF) in the Prophylaxis and Treatment of Endotoxic Shock in Cynomolgus Monkeys," Abstract 184, *Clinical Science* 76(S20):50.

Exley, A.R. et al. (1990). "Monoclonal Antibody to TNF in Severe Septic Shock," *The Lancet* 335:1275-1277.

Fauci, A.S. et al. eds. (1998). *Harrison's Priniciples of Internal Medicine*,14th Edition, McGraw Hill Companies, Inc., p. 300.

Felici, F. et al. (Jun. 15, 1993). "Mimicking of Discontinuous Epitopes by Phage-Displayed Peptides. II. Selection of Clones Recognized by a Protective Monoclonal Antibody Against the *Bordetella pertussis* Toxin From Phage Peptide Libraries," *Gene* 128(1):21-27.

Fendly, B.M. et al. (1987). "Murine Monoclonal Antibodies Defining Neutralizing Epitopes on Tumor Necrosis Factor," *Hybridoma* 6(4):359-370.

Ferrante, A. et al. (Nov. 1, 1993). "Killing of *Stahpylococcus aureus* by Tumor Necrosis Factor-α-Activated Neutrophils. The Role of Serum Opsonins, Integrin Receptors, Respiratory Burst, and Degranulation," *J. Immunol.* 151(9):4821-4828.

Ferrante, A. et al. (Apr. 15, 1994). "Interaction of *Staphylococcus aureus* with Human Neutrophils and the Down-Regulation of TNF Receptors," *J. Immunol.* 152(8):3998-4004.

Ferrante, J.V. et al. (Mar. 1997). "Altered Responses of Human Macrophages to Lipopolysaccharide by Hydroperoxy Eicosatetraenoic Acid, Hydroxy Eicosatetraenoic Acid, and Arachidonic Acid," *J. Clin. Invest.* 99:1445-1452.

Ferrieres, G. et al. (1998). "Human Cardiac Troponin 1: Precise Identification of Antigenic Epitopes and Prediction of Secondary Structure," *Clinical Chemistry* 44(3):487-493.

Fersht, A.R. et al. (Mar. 21, 1985). "Hydrogen Bonding and Biological Specificity Analysed by Protein Engineering," *Nature* 314:235-238.

Fiedler, V.B. et al. (1992). "Monoclonal Antibody to Tumor Necrosis Factor α Prevents Lethal Endotoxin Sepsis in Adult Rhesus Monkeys," *J. Lab. Clin. Med.* 120:574-588.

Fiers, W. (1999). "Review: Tumor Necrosis Factor: Characterization at the Molecular, Cellular and in vivo Level," *FEBS Lett.* 285(2):199-212.

Fieser, T.M. et al. (Dec. 1987). "Influence of Protein Flexibility and Peptide Conformation on Reactivity of Monoclonal Anti-Peptide Antibodies with a Protein α-Helix," *Proc. Natl. Acad. Sci. USA* 84:8568-8572.

Finkelman, F.D. et al. (Aug. 1, 1993). "Anti-Cytokine Antibodies as Carrier Proteins. Prolongation of in Vivo Effects of Exogenous Cytokines by Injection of Cytokine-Anti-Cytokine Antibody Complexes," *J. Immunol.* 151(3):1235-1244.

Fisher, C.J. Jr. et al. (1996). "Treatment of Septic Shock with the Tumor Necrosis Factor Receptor:Fc Fusion Protein," *N. Engl. J. Med.* 334(26):1697-1702.

Folks, T.M. et al. (1989). "Tumor Necrosis Factor α Induces Expression of Human Immunodeficiency Virus in a Chronically Infected T-Cell Clone," *Proc. Natl. Acad. Sci. USA* 86:2365-2358.

Fomsgaard, A. et al. (1989). "Auto-Antibodies to Tumour Necrosis Factor α in Healthy Humans and Patients with Inflammatory Diseases and Gram-Negaive Bacterial Infections," *Scand. J. Immunol.* 30:219-223.

Fong, Y. et al. (1989). "Antibodies to Cachectin/Tumor Necrosis Factor Reduce Interleukin 1β and Interleukin 6 Appearance During Lethal Bacteremia," *J. Exp. Med.* 170:1627-1633.

Fong, Y. et al. (1990). "Tumor Necrosis Factor in the Pathophysiology of Infection and Sepsis," *Clin. Immunol. Immunopathol.* 55:157-170.

Forest, K.T. et al. (Feb. 1996). "Assembly and Antigenicity of the Neisseria Gonorrhoeae Pilus Mapped with Antibodies," *Infect. Immun.* 64(2):644-652.

Fournier, A. et al. (1989). "Applications of BOP Reagent in Solid Phase Peptide Synthesis," *Int. J. Peptide Protein Res.* 33:133-139.

Frank, R. (1992). "Spot-Synthesis: An Easy Technique For the Positionally Addressable, Parallel Chemical Synthesis on a Membrane Support," *Tetrahedron* 48(42):9217-9232.

Frank, R. (2002). "The SPOT-Synthesis Technique Synthetic Peptide Arrays on Membrane Supports—Prinicples and Applications," *Journal of Immunological Methods* 267:13-26.

Franklin, M.C. et al. (Apr. 2004). "Insights Into ErbB Signaling From the Structure of the ErbB2-pertuzumab Complex," *Cancer Cell* 5:317-328.

Fransen, L. et al. (1986). "Recombinant Tumor Necrosis Factor: Its Effect and its Synergism with Interferon-γ on a Variety of Normal and Transformed Human Cell Lines," *Eur. J. Cancer. Clin. Oncol.* 22(4):419-426.

Fransen, L. et al. (1986). "Recombinant Tumor Necrosis Factor: Species Specificity for a Variety of Human and Murine Transformed Cell Lines," *Cell. Immunol.* 100:260-267.

Fu, Z.Q. et al. (1995). "Model Complexes of Tumor Necrosis Factor-α with Receptors R1 and R2," *Protein. Eng.* 8(12):1233-1241.

Galloway, C. et al. (1991). "Monoclonal Anti-Tumor Necrosis Factor (TNF) Antibodies Protect Mouse and Human Cells from TNF Cytotoxicity," *J. Immunol. Methods* 140:37-43.

Gao, B. et al. (Jul. 1, 1996). "Multiple Interactive Residues of Recognition—Elucidation of Discontinuous Epitopes with Linear Peptides," *J. Immunol.* 157(1):183-188.

Garnier, J. et al. (1978). "Analysis of the Accuracy and Implications of Simple Methods for Predicting the Secondary Structure of Globular Proteins," *J. Mol. Biol.* 120:97-120.

Gatanaga, T. et al. (1990). "Identification of TNF-LT Blocking Factor(s) in the Serum and Ultrafiltrates of Human Cancer Patients," *Lymphokine Research* 9(2):225-229.

GenBank Accession No. M32046 "Mouse Antibody Response to Group A Strptococcal Carbohydrate," created on Apr. 27, 1993, located at <http://www.ncbi.nlm.nih.gov>, last visited on May 6, 2004.

GenBank Accession No. N90300 "The WashU-Merck EST Project," created on Apr. 2, 1996, located at, located at <http://www.ncbi.nlm.nih.gov>, last visited on May 6, 2004.

GenBank Accession No. P16753, created Aug. 1, 1990, located at <http://www.ncbi.nlm.nih.gov/entrez/viewer.fcgi?db=protein&val=139232>, last visited on Dec. 6, 2004, five pages.

Getzoff, E.D. et al. (Mar. 6, 1987). "Mechanisms of Antibody Binding to a Protein," *Science* 235:1191-1196.

Getzoff, E.D. et al. (1988). "The Chemistry and Mechanism of Antibody Binding to Protein Antigens," *Adv. Immunol.* 43:1-98.

Geysen, H.M. (1985). "Antigen-Antibody Interactions at the Molecular Level: Adventures in Peptide Synthesis," *Immunology Today* 6:364-369.

Geysen, H.M. (1990). "Molecular Technology: Peptide Epitope Mapping and the Pin Technology," *Southeast Asian J. Trop. Med. Public Health* 21:523-533.

Geysen, H.M. et al. (Jul. 1984). "Use of Peptide Synthesis to Probe Viral Antigens for Epitopes to a Resolution of a Single Amino Acid," *Proc. Natl. Acad. Sci.* 81:3998-4002.

Geysen, H.M. et al. (Jan. 1985). "Small Peptides Induce Antibodies with a Sequence and Structural Requirement for Binding Antigen Comparable to Antibodies Raised Against the Native Protein," *Proc. Natl. Acad. Sci. USA* 82(1):178-182.

Geysen, H.M. et al. (1986). "*A Priori* Delineation of a Peptide Which Mimics a Discontinuous Antigenic Determinant," *Molecular Immunology* 23(7):709-715.

Geysen, H.M. et al. (1986). "The Delineation of Peptides Able to Mimic Assembled Epitopes," *In Synthetic Peptides as Antigens: Ciba Found Symp.*, John Wiley & Sons, Inc., 119:130-149.

Geysen, H.M. et al. (1987). "Chemistry of Antibody Binding to a Protein," *Science* 235:1184-1190.

Geysen, H.M. et al. (1987). "Strategies for Epitope Analysis Using Peptide Synthesis," *J. Immunol. Methods* 102:259-274.

Geysen, H.M. et al. (1988). "A Synthetic Strategy for Epitope Mapping" *In Peptides: Chemistry and Biology, Proceedings of the Tenth American Peptide Symposium*, May 23-28, 1987, St. Louis MO, Marshall, G.R. ed., ESCOM Science Publishers: The Netherlands, pp. 519-523.

Geysen, H.M. et al. (1988). "Cognitive Features of Continuous Antigenic Determinants," *Journal of Molecular Recognition* 1(1):32-41.

Geysen, H.M. et al. (1993). "Screening Chemically Synthesized Peptide Libraries for Biologically-Relevant Molecules," *Bioorganic & Medicinal Chemistry Letters* 3:397-404.

Gherardi, E. et al. (1992). "Original and Artificial Antibodies," *Nature* 357(6375):201-202.

Gilbert, D. et al. (1995). "An Idiotype D23-Bearing Polyspecific, Murine Anti-DNA Monoclonal Antibody Forms Glomerular Immune Deposits. Pathogenic Role of Natural Autoantibodies," *Molecular Immunology* 32(7):477-486.

Gillies, S.D. et al. (1989). "High-Level Expression of Chimeric Antibodies Using Adapted cDNA Variable Region Cassettes," *J. Immunol. Methods*, 125:191-202.

Goh, C. (1990). "Tumour Necrosis Factors in Clinical Practice," *Annals of the Academy of Medicine* 19(2):235-239.

Gomme, P.T. et al. (1999). "Evaluation of a Pepscan Approach to Identify Epitopes Recognised by Anti-h TSH Monoclonal Antibodies," *J. Biochem. Biophys. Methods* 38:53-70.

Gomme, P.T. et al. (Sep. 1999). "Characterization of Epitope Regions of Thyrotropin β-Subunit Recognized by the Monoclonal Antibodies mAb279 and mAb299: A Chimeric Peptide Approach," *J. Pept. Res.* 54(3):218-229.

Gorman, S.D. et al. (1990). "Humanisation of Monoclonal Antibodies for Therapy," *Sem. Immunol.* 2:457-466.

Granier, C. ed. (2002). "Special Issue on 'Methods of Parallel Peptide Synthesis and Their Contributions to Deciphering Molecular Interactions in the Immune System," *Journal of Immunological Methods* 267:1-2.

Granier, C. et al. (1989). "Review: The Antigenic Structure of a Scorpion Toxin," *Molecular Immunology* 26(6):503-513.

Grau, G.E. et al. (1987). "Tumor Necrosis Factor (Cachectin) As An Essential Mediator in Murine Cerebral Malaria," *Science* 237:1210-1212.

Gray, P.W. et al. (1984). "Cloning and Expression of cDNA for Human Lymphotoxin, a Lymphokine with Tumour Necrosis Activity," *Nature* 312(20/27):721-724.

Griffiths, A.D. et al. (1993). "Human Anti-Self Antibodies With High Specificity From Phage Display Libraries," *The EMBO Journal* 12(2):725-734.

Gruss, H.J. et al. (1995). "The TNF Ligand Superfamily and Its Relevance for Human Diseases," *Cytokines and Mol. Ther.* 1:75-105.

Güssow, D. et al. (1991). "Humanization of Monoclonal Antibodies" Chapter 5 In *Methods in Enzymology*, Academic Press, Inc.: New York, NY, vol. 203, pp. 99-121.

Haak-Frendscho, M. et al. (Feb. 1994). "Inhibition of TNF by a TNF Receptor Immunoadhesin. Comparison to an Anti-TNF Monoclonal Antibody," *J. Immunol.* 152:1347-1353.

Haber, E. (1992). "Engineered Antibodies as Pharmacological Tools," *Immunol Rev.* 130:189-212.

Hahn, T. et al. (1985). "Use of Monoclonal Antibodies to a Human Cytotoxin For Its Isolation and For Examining the Self-Induction of Resistance to This Protein," *Proc. Natl. Acad. Sci.* USA 82:3814-3818.

Hanauer, S.B. et al. (May 4, 2002). "Maintenance Infliximab for Crohn's Disease: The Accent I Randomised Trial," *Lancet* 359:1541-1549.

Harris, W. J. et al. (1993). "Therapeutic Antibodies—the Coming of Age," *TIBTECH* 11:42-44.

Hasegawa, A. et al. (2003). "Modifying TNFα for Therapeutic Use: A Perspective on the TNF Receptor System," located at <http://bentham.org/mrmc1-1/murali/murali.html> last visited on Jan. 9, 2004, eleven pages.

Hawkins, R.E. et al. (1992). "Selection of Phage Antibodies by Binding Affinity: Mimicking Affinity Maturation," *J. Mol. Biol.* 226:889-896.

Hawkins, R.E. et al. (1993). "The Contribution of Contact and Non-Contact Residues of Antibody in the Affinity of Binding to Antigen. The Interaction of Mutant D1.3 Antibodies with Lysozyme," *J. Mol. Biol.* 234:958-964.

Hayashi, H. et al. (1985). "An Enzyme-Linked Immunosorbent Assay For Recombinant Human Tumor Necrosis Factor Using Monoclonal Antibody," *Recent Adv. Chemother.* 820-821.

Hayder, H. et al. (1999). "Adenovirus-Induced Liver Pathology is Mediated Through TNF Receptors I and II but is Independent of TNF or Lymphotoxin," *J. Immunology* 163:1516-1520.

Hazarika, P. et al. (1988). "Epitope Mapping of Alpha-Transforming Growth Factor: Evidence of an Immunodominant Region," *Life Sci.* 42(24):2525-2531.

Herve, P. et al. (1990). "Monoclonal Anti TNF I Antibody for the Treatment of Severe Acute GvHD in Humans," Abstract 3.25, *Lymphoma Res.* 9:591.

Hilpert, K. et al. (2000). "Characterizing and Optimizing Protease/Peptide Inhibitor Interactions, a New Application for Spot Synthesis," *J. Biochem.* (Tokyo) 128:1051-1057.

Hinshaw, L.B. et al. (1990). "Survival of Primates in $LD_{100}$ Septic Shock Following Therapy with Antibody to Tumor Necrosis Factor (TNFα)," *Circ. Shock* 30:279-292.

Hirai et al. (1987). "Production and Characterization of Monoclonal Antibodies to Human Tumor Necrosis Factor," *J. Immunol. Meth.* 96:57-62.

Hird, V. et al. (1990). "Immunotherapy with Monoclonal Antibodies," Chapter 17 In *Genes and Cancer*, Carney, D. et al eds., John Wiley & Sons: New York, NY, pp. 183-189.

Hodits, R.A. et al. (1995). "An Antibody Fragment from a Phage Display Library Competes for Ligand Binding to the Low Density Lipoprotein Receptor Family and Inhibits Rhinovirus Infection," *The Journal of Biological Chemistry* 270(41):24078-24085.

Hohmann, H-P. et al. (1989). "Two Different Cell Types Have Different Major Receptors for Human Tumor Necrosis Factor (TNFα)," *The Journal of Biological Chemistry* 264(25):14927-14934.

Hohmann, H-P. et al. (Sep. 5, 1990). "Tumor Necrosis Factors-α and -β Bind to the Same Two Types of Tumor Necrosis Factor Receptors and Maximally Activate the Transcription Factor NF-kB at Low Receptor Occupancy and Within Minutes after Receptor Binding," *J. Biol. Chem.* 265:15183-15188.

Holler, E. et al. (1995). "Modulation of Acute Graft-Versus-Host Disease After Allogeneic Bone Marrow Transplantation by Tumor Necrosis Factor α (TNF α) Release in the Course of Pretransplant Conditioning: Role of Conditioning Regimens and Prophylactic Application of a Monoclonal Antibody Neutralizing Human TNFα (MAK 195F)," *Blood* 86:890-899.

Holliger, P. et al. (1995). "Artificial Antibodies and Enzymes: Mimicking Nature and Beyond," *TIBTECH* 13:7-9.

Hoogenboom, H.R. (1992). "By-Passing Immunisation: Human Antibodies from Synthetic Repertoires of Germline $V_H$ Gene Segments Rearranged in Vitro," *J. Mol. Biol.* 227:381-388.

Hoogenboom, H.R. (1997). "Designing and Optimizing Library Selection Strategies for Generating High-Affinity Antibodies," *TIBTECH* 15:62-70.

Hoogenboom, H.R. et al. (1991). "Construction and Expression of Antibody-Tumor Necrosis Factor Fusion Proteins," *Molecular Immunology* 28(9):1027-1037.

Hoogenboom, H.R. et al. (1991). "Multi-Subunit Proteins on the Surface of Filamentous Phage: Methodoligies for Displaying Antibody (Fab) Heavy and Light Chains," *Nucleic Acids Research* 19(15):4133-4137.

Hoogenboom, H.R. et al. (1992). "Building Antibodies from their Genes," *Immunological Reviews* 130:41-68.

Hoogenboom, H.R. et al. (1999). "Selection-Dominant and Nonaccessible Epitopes on Cell-Surface Receptors Revealed by Cell-Panning with a Large Phage Antibody Library," *Eur. J. Biochem.* 260:774-784.

Hopp, T.P. et al. (Jun. 1981). "Prediction of Protein Antigenic Determinants from Amino Acid Sequences," *Proc. Natl. Acad. Sci.* USA 78(6):3824-3828.

Huang, X. et al. (1991). "A Time-Efficient, Linear-Space Local Similarity Algorithm," In *Advances in Applied Mathematics*, Academic Press, Inc., 12(1):337-357.

Huse, W.D. et al. (Dec. 8, 1989). "Generation of a Large Combinatorial Library of the Immunoglobulin Repertoire in Phage Lambda," *Science* 246:1275-1281.

Idriss, H.T. et al. (2000). "TNFα and the TNF Receptor Superfamily: Structure-Function Relationship(s)," *Microscopy Research and Technique* 50:184-195.

Israel, S. et al. (1986). "Binding of Human TNF-α to High-Affinity Cell Surface Receptors: Effect of IFN," *Immunol. Lett.* 12:217-224.

Ivanyi, J. (1982). "Study of Antigenic Structure and Inhibition of Activity of Human Growth Hormone and Chorionic Somatotropin by Monoclonal Antibodies," *Molecular Immunology* 19(12):1611-1618.

Jacob, C.O. et al. (1988). "Tumour Necrosis Factor-α in Murine Autoimmune 'Lupus' Nephritis," *Nature* 331:356-358.

James, K. et al. (1987). "Human Monoclonal Antibody Production: Current Status and Future Prospects," *Journal of Immunological Methods* 100:5-40.

Jameson, B.A. et al. (Jun. 3, 1988). "Location and Chemical Synthesis of a Binding Site for HIV-1 on the CD4 Protein," *Science* 240:1335-1339.

Jarvis, C.D. et al. (1989). "Mouse Antibody Response to Group a Streptococcal Carbohydrate," *J. Immunology* 143(12):4213-4220.

Jersmann, H.P.A. et al. (Apr. 1998). "Enhancement of Lipopolysaccharide-Induced Neutrophil Oxygen Radical Production by Tumor Necrosis Factor Alpha," *Infection and Immunity* 66(4):1744-1747.

Jespers, L.S. et al. (1994). "Guiding the Selection of Human Antibodies from Phage Display Repertoires to a Single Epitope of an Antigen," *Bio/Technology* 12:899:903.

Jia, X-C. et al. (2004). "A Novel Method of Multiplexed Competitive Antibody Binning for the Characterization of Monoclonal Antibodies," *J. Immunol. Methods* 288:91-98.

Jin, L. et al. (1992). "High Resolution Functional Analysis of Antibody-Antigen Interactions," *J. Mol. Biol.* 226:851-865.

Jones, E.Y. et al. (1989). "Structure of Tumour Necrosis Factor," *Nature* 338: 225-228.

Jones, M. et al. (1996). "Does Exposure to Immunosuppressive Therapy Increase the 10 Year Malignancy and Mortality Risks in Rheumatoid Arthritis? A Matched Cohort Study," *British Journal of Rheumatology* 35:738-745.

Josephson, K. et al. (Jul. 2002). "Noncompetitive Antibody Neutralization of IL-10 Revealed by Protein Engineering and X-Ray Crystallography," *Structure* 10:981-987.

Kabat, E.A. (1991). *Sequences of Proteins of Immunological Interest*, 5th Edition, from *US Public Health Services*, NIH publication No. 91-3242, Table of Contents, pp. iii-xi.

Kameyama, K-Z. et al. (1989). "Convenient Plasmid Vectors for Construction of Chimeric Mouse/Human Antibodies," *FEBS Lett.* 244(2):301-306.

Kang, A.S. et al. (1991). "Antibody Redesign by Chain Shuffling From Random Combinatorial Immunoglobulin Libraries," *Proc. Natl. Acad. Sci.* USA 88:11120-11123.

Karpusas, M. et al. (Apr. 2001). "Structure of CD40 Ligand in Complex with the Fab Fragment of a Neutralizing Humanized Antibody," *Structure* 9:321-329.

Kassiotis, G. et al. (2001). "Uncoupling the Proinflammatory From the Immunosuppressive Properties of Tumor Necrosis Factor (TNF) at the p55 TNF Receptor Level: Implications For Phathogenesis and Therapy of Autoimmune Demyelination," *J. Exp. Med.* 193(4):427-434.

Kawasaki, H. et al. (1989). "Analysis of Endotoxin Fever in Rabbits by Using a Monoclonal Antibody to Tumor Necrosis Factor (Cachectin)," *Infection and Immunity* 57(10):3131-3135.

Knight, D.M. et al. (1993). "Construction and Initial Characterization of a Mouse-Human Chimeric Anti-TNF Antibody," *Molec. Immunol.* 30(16):1443-1453.

Kohase, M. et al. (1986). "Induction of $\beta_2$-Interferon by Tumor Necrosis Factor: A Homeostatic Mechanism in the Control of Cell Proliferation," *Cell* 45:659-666.

Korth, C. et al. (Nov. 6, 1997). "Prion (PrP$^{Sc}$)-Specific Epitope Defined by a Monoclonal Antibody," *Nature* 390:74-77.

Kramer, A. (1997). "Molecular Basis of Binding Promiscuity of an Anti-p24 (HIV-1) Monoclonal Antibody," *Cell* 91:799-809.

Kramer, A. et al. (1995). "A General Route to Fingerprint Analyses of Peptide-Antibody Interactions Using a Clustered Amino Acid Peptide Library: Comparison with a Phage Display Library," *Mol. Immunol.* 32(7):459-465.

Kull, F.C. et al. (Sep. 1985). "Cellular Receptor for $^{125}$I-Labeled Tumor Necrosis Factor: Specific Binding, Affinity Labeling, and Relationship to Sensitivity," *Proc. Natl. Acad. Sci. USA* 82:5756-5760.

Kumaratilake, L.M. et al. (May 1995). "A Synthetic Tumor Necrosis Factor-$\alpha$ Agonist Peptide Enhances Human Polymorphonuclear Leukocyte-Mediated Killing of *Plasmodium falciparum* in Vitro and Suppresses *Plasmodium chabaudi* Infection in Mice," *J. Clin. Invest.* 95:2315-2323.

Kunkel, S.L. et al. (1989). "Mechanisms That Regulate the Production and Effects of Tumor Necrosis Factor-$\alpha$," *Critical Rev. Immunol.* 9(2):93-117.

Labrousse, H. et al. (1997). "Effect of Temperature on the Reactivities of Polyreactive and Monospecific Monoclonal IgC Antibodies," *Res. Immunol.* 148:267-276.

Langedijk, J.P.M. et al. (1990). "Location of Epitopes on the Major Core Protein p24 of Human Immunodeficiency Virus," *J. Gen. Virol.* 71:2609-2614.

Langeveld, J.P.M. et al. (2001). "Characterisation of a Protective Linear B Cell Epitope Against Feline Parvoviruses," *Vaccine* 19:2352-2360.

Lassalle, P. et al. (1991). "Potential Implication of Endothelial Cells in Bronchial Asthma," *Int. Arch Allergy Appl. Immunol.* 94:233-238.

Laster, A.J. et al. (Aug. 1987). "Polyspecific Reactivity of a Murine Monoclonal Antibody That Binds to Nuclear Matrix-Associated, Chromatin-Bound Autoantigens," *Clin. Immunol. Immunopathol.* 44(2):187-205.

Laune, D. et al. (1997). "Systematic Exploration of the Antigen Binding Activity of Synthetic Peptides Isolated From the Variable Regions of Immunoglobulins," *The Journal of Biological Chemistry* 272(49):30937-30944.

Laune, D. et al. (1998). "Peptide Models of Immunological Recognition: Paratope Dissection by Multiple Peptide Synthesis," *Clin. Chem. Lab. Med.* 36(6):367-71.

Laune, D. et al. (2000). "Dissection of an Antibody Paratope into Peptides Discloses the Idiotope Recognized by the Cognate Anti-Idiotypic Antibody," *J. Immunol. Methods* 239(1-2):63-73.

Laune, D. et al. (2002). "Application of the Spot Method to the Identification of Peptides and Amino Acids from the Antibody Paratope That Contribute to Antigen Binding," *Journal of Immunological Methods* 267:53-70.

Laver, W.G. et al. (May 18, 1990). "Epitopes on Protein Antigens: Misconceptions and Realities," *Cell* 61:553-556.

Liang et al. (1986). "Production and Characterization of Monoclonal Antibodies Against Recombinant Human Tumor Necrosis Factor/Cachectin," *Biochem. Biophys. Res. Comm.* 137(2):847-854.

Lidbury, B.A. (Apr. 1993). "The Enhancement of Human Tumor Necrosis Factor-$\alpha$ Antiviral Activity In Vivo by Monoclonal and Specific Polyclonal Antibodies," *Lymphokine Cytokine Res.* 12(2):69-74.

Lidbury, B.A. et al. (1994). "The Effect of Enhancing Antibodies on TNF Interactions with its Specific Receptor: Consequences for In Vitro TNF Antiviral Activity," *Biotechnol. Ther.* 5(1-2):27-45.

Liu, Z. et al. (1999). "Fine Mapping of the Antigen-Antibody Interaction of scFv217, are Combinant Antibody Inhibiting RNA Polymerase From Drosophila. Melanogaster," *J. Mol. Recognit.* 12:103-111.

Llanos, R. et al. (1999). "Tubulin Binding Sites on $_\gamma$-Tubulin: Identification and Molecular Characterization," *Biochemistry* 38:15712-15720.

Lo Conte, L. et al. (1999). "The Atomic Structure of Protein-Protein Recognition Sites," *J Mol Biol.* 285:2177-2198.

Loetscher, H. et al. (1990). "Molecular Cloning and Expression of the Human 55 kd Tumor Necrosis Factor Receptor," *Cell* 61:351-359.

Loetscher, H. et al. (Nov. 25, 1990). "Purification and Partial Amino Acid Sequence Analysis of Two Distinct Tumor Necrosis Factor Receptors from HL60 Cells," *J. Biol. Chem.* 265(33):20131-20138.

Loetscher, H. et al. (1993). "Human Tumor Necrosis Factor $\alpha$(TNF $\alpha$) Mutants with Exclusive Specificity for the 55-kDa or 75-kDa TNF Receptors," *J. Biol. Chem.* 268(35):26350-26357.

Love, T.W. et al. (1989). "Recombinant Antibodies Possessing Novel Effector Functions" Chapter 35 *In Methods in Enzymology*, Academic Press, Inc. vol. 178, pp. 515-527.

Lucas, R. et al. (1990). "Generation and Characterization of a Neutralizing Rat Anti-rmTNF-$\alpha$ Monoclonal Antibody," *Immunology* 71:218-223.

Luettig, B. et al. (1989). "Evidence For The Existence of Two Forms of Membrane Tumor Necrosis Factor: An Integral Protein And A Molecule Attached To Its Receptor," *The Journal of Immunology* 143(12):4034-4038.

MacCallum, R.M. et al. (1996). "Antibody-Antigen Interactions: Contact Analysis and Binding Site Topography," *J. Mol. Biol.* 262:732-745.

MacDonald, T.T. et al. (1990). "Tumour Necrosis Factor-Alpha and Interferon-Gamma Production Measured at the Single Cell Level in Normal and Inflamed Human Intestine," *Clin. Exp. Immunol.* 81:301-305.

Mack, P. et al. (Dec. 1991). "The Use of Peptides as Therapeutics & Vaccines," *Australas. Biotechnol.* 1(3):160-163.

Maeji, N.J. et al. (May-Jun. 1991). "Systematic Screening for Bioactive Peptides," *Pept. Res.* 4(3):142-146.

Mahler, S.M. et al. (1997). "Cloning and Expression of Human V-Genes Derived From Phage Display Libraries as Fully Assembled Human Anti-TNF$\alpha$ Monoclonal Antibodies," *Immunotechnology* 3:31-43.

Maini, R.N. et al. (1998). "Therapeutic Efficacy of Multiple Intravenous Infusions of Anti-Tumor Necrosis Factor $\alpha$ Monoclonal Antibody Combined with Low-Dose Weekly Methotrexate in Rheumatoid Arthritis," *Arthritis and Rheumatism* 41(9):1552-1563.

Mariuzza, R. A. et al. (1993). "The Basics of Binding: Mechanisms of Antigen Recognition and Mimicry by Antibodies," *Curr. Opin. Immunol.* 5:50-55.

Marks, J.D. (1992). "Molecular Evolution of Proteins on Filamentous Phage," *The Journal of Biological Chemistry* 267(23):16007-16010.

Marks, J.D. et al. (1991). "By-Passing Immunization: Human Antibodies from V-Gene Libraries Displayed on Phage," *J. Mol. Biol.* 222:581-597.

Marks, J.D. et al. (1991). "Oligonucleotide Primers for Polymerase Chain Reaction Amplification of Human Immunoglobulin Variable Genes and Design of Family-Specific Oligonucleotide Probes," *Eur. J. Immunol.* 21(4):985-991.

Mateo, C. et al. (2000). "Removal of Amphipathic Epitopes From Genetically Engineered Antibodies: Production of Modified Immunoglobulins with Reduced Immunogenicity," *Hybridoma* 19(6):463-471.

Mathison, J.C. et al. (1988). "Participation of Tumor Necrosis Factor in the Mediation of Gram Negative Bacterial Lipopolysaccharide-Induced Injury in Rabbits," *J. Clin. Invest.* 81:1925-1937.

McCafferty, J. et al. (1990). "Phage Antibodies: Filamentous Phage Displaying Antibody Variable Domains," *Nature* 348:552-554.

Meager et al. (1987). "Preparation and Characterization of Monoclonal Antibodies Directed Against Antigenic Determinants of Recombinant Human Tumour Necrosis Factor (rTNF)," *Hybridoma* 6(3):305-311.

Mease, P.J. (2000). "Etanercept in the Treatment of Psoriatic Arthritis and Psoriasis: A Randomised Trial," *Lancet* 356:385-390.

Meulenberg, J.J.M. et al. (1998). "Localization and Fine Mapping of Antigenic Sites on the Nucleocapsid Protein N of Porcine Reproductive and Respiratory Syndrome Virus with Monoclonal Antibodies," *Virology* 252:106-114.

Molina, F. et al. (May/Jun. 1996) "Improved Performances of Spot Multiple Peptide Synthesis,"0 *Peptide Research* 9(3):151-155.

Möller, A et al. (1990). "Monoclonal Antibodies to Human Tumor Necrosis Factor α : In Vitro and In Vivo Application," *Cytokine* 2(3):162-169.

Montero-Julian, F.A. et al. (Feb. 15, 1995). "Pharmacokinetic Study of Anti-Interleukin-6 (IL-6) Therapy With Monoclonal Antibodies: Enhancement of IL-6 Clearance by Cocktails of Anti-IL-6 Antibodies," *Blood* 85(4):917-924.

Moreland, L.W. et al. (1997). "Treatment of Rheumatoid Arthritis with a Recombinant Human Tumor Necrosis Factor Receptor (p75)-Fc Fusion Protein," *N. Engl. J. Med.* 337(3):141-147.

Morrison, S.L. (1985). "Transfectomas Provide Novel Chimeric Antibodies," *Science* 229:1202-1207.

Morrison, S.L. (1989). "Genetically Engineered (Chimeric) Antibodies," *Hospital Practice* pp. 65-80.

Morrison, S.L. et al. (Nov. 1984). "Chimeric Human Antibody Molecules: Mouse Antigen-Binding Domains with Human Constant Region Domains," *Proc. Natl. Acad. Sci. U S A*. 81(21):6851-6855.

Mountain, A. et al. (1992). "Engineering Antibodies For Therapy" Chapter 1 *In Biotechnology and Genetic Engineering Reviews*, vol. 10, pp. 1-142.

Mulé, J.J. et al. (1990). "Antitumor Activity of Recombinant Interleukin 6 in Mice," *The Journal of Experimental Medicine* 171:629-636.

Murch, S.H. et al. (1991). "Serum Concentrations of Tumour Necrosis Factor α in Childhood Chronic Inflammatory Bowel Disease," *Gut* 32:913-917.

Muso, E. et al. (Mar. 1987). "A Polyspecific Monoclonal Anti-DNA Autoantibody Also Binds to Cell-Surface Protein(s)," *Clin. Immunol. Immunopathol*. 42(3):370-374.

Mutter, M. et al. (1986). "Approaches to Synthetic Vaccines: Design of Epitope-Containing Amphiphilic Peptides Matching the Antigenic Structure in the Native Protein," *Helv. Chim. Acta*. 69:985-995.

Mutuberria, R. et al. (2004). "Isolation of Human Antibodies to Tumor-Associated Endothelial Cell Markers by in vitro Human Endothelial Cell Selection with Phage Display Libraries," *J. Immunol. Methods* 287:31-47.

Nagahira, K. et al. (1995). "Epitope Mapping of Monoclonal Antibodies to Tumor Necrosis Factor-α by Synthetic Peptide Approach," *Immunol. Letters* 46:135-141.

Nagai, M. et al. (1988). "Antibody to Tumor Necrosis Factor (TNF) Reduces Endotoxin Fever," *Experientia* 44:606-607.

Nagaoka, M. et al. (2003). "Single Amino Acid Substitution in the Mouse IgG1 Fc Region Induces Drastic Enhancement of the Affinity to Protein A," *Protein Engineering* 16(4):243-245.

Naismith, J.H. et al. (1996). "Seeing Double: Crystal Structures of the Type I TNF Receptor," *J. Mol. Recognition* 9:113-117.

Naismith, J.H. et al. (Feb. 1998). "Modularity in the TNF-Receptor Family," *Trends Biochem. Sci.* 23:74-79.

Nanda, N.K. et al. (Aug. 1, 1995). "Recognition of Multiple Peptide Cores by a Single T Cell Receptor," *J. Exp. Med.* 182(2):531-539.

Natanson, C. et al., (1994) "Selected Treatment Strategies for Septic Shock Based on Proposed Mechanisms of Pathogenesis," *Ann. Int. Med.* 120(9):771-783.

Nawroth, P. et al. (1988). "Tumor Necrosis Factor/Cachectin-Induced Intravascular Fibrin Formation in Meth A Fibrosarcomas," *J. Exp. Med.* 168:637-647.

Nawroth, P.P. et al. (1986). "Modulation of Endothelial Cell Hemostatic Properties by Tumor Necrosis Factor," *J. Exp. Med.* 163:740-745.

Neda, H. (1987) "Analysis of the Tumor Necrosis Factor (TNF) Receptor of Various Tumor Cells," *Sapporo Med J.* 56(2):305-317.

Nedwin, G.E. et al. (1985). "Human Lymphotoxin and Tumor Necrosis Factor Genes: Structure, Homology and Chromosomal Localization," *Nucleic Acids Research* 13(17):6361-6373.

Niedrig, M. et al. (1992). "Inhibition of Viral Replication by Monoclonal Antibodies Directed Against Human Immunodeficiency Virus gp120," *J. Gen. Virol.* 73:2451-2455.

Nisihara, T. et al. (2001). "Humanization and Epitope Mapping of Neutralizing Anti-Human Fas Ligand Monoclonal Antibodies: Structural Insights into Fas/Fas Ligand Interaction," *J. Immunol.* 167:3266-3275.

Nissen-Meyer, J. et al. (1987). "Effect of Antisera Against Recombinant Tumor Necrosis Factor and the Monocyte-Derived Cytotoxin(s) on Monocyte-Mediated Killing of Various Tumor Cells," *Cell. Immunol*. 109:384-396.

Nissim, A. et al. (1994). "Antibody Fragments From a 'Single Pot' Phage Display Library as Immunochemical Reagents," *The EMBO Journal* 13(3):692-698.

Nophar, Y. et al. (1990). "Soluble Forms of Tumor Necrosis Factor Receptors (TNF-Rs). The cDNA for the Type I TNF-R, Cloned Using Amino Acid Sequence Data of its Soluble Form, Encodes both the Cell Surface and a Soluble Form of the Receptor," *EMBO J.* 9(10):3269-3278.

Notredame, C. et al. (Sep. 8, 2000). "T-Coffee: A Novel Method for Fast and Accurate Multiple Sequence Alignment," *J. Mol. Biol.* 302(1):205-217.

Novotny, J. et al. (1987). "Antigenicity of Myohemerythrin," *Science* 238:1584.

Office Action for U.S. Appl. No. 11/326,996, mailed Oct. 26, 2006, 18 pages.

Oh, C.J. et al. (2000). "Treatment with Anti-Tumor Necrosis Factor-α (TNF-α) Monoclonal Antibody Dramatically Decreases the Clinical Activity of Psoriasis Lesions," *J. of the Am. Acad. Dermatol*. 42:829-830.

Old, L.J. (Nov. 8, 1985). "Tumor Necrosis Factor (TNF)," *Science* 230:630-632.

Oliff, A. et al. (1987). "Tumors Secreting Human TNF/Cachectin Induce Cachexia in Mice," *Cell* 50:555-563.

Olsson, P.G. et al. (1991). "Antigenicity of Mouse Monoclonal Antibodies: A Study on the Variable Region of the Heavy Chain," *J. Theor. Biol.* 151:111-122.

Omulecki, A. et al. (1996). "Is Pentoxifylline Effective in the Treatment of Psoriasis," *J. of the Am. Acad. Dermatol.* 34(4):714-715.

Opal, S.M. et al. (1990). "Efficacy of a Monoclonal Antibody Directed Against Tumor Necrosis Factor in Protecting Neutropenic Rats from Lethal Infection with *Pseudomonas aeruginosa*," *The Journal of Infectious Diseases* 161:1148-1152.

Orkin, S.H. et al. (1995). "Report and Recommendations of the Panel to Assess the NIH Investment in Research on Gene Therapy," *NIH* 29 pages.

Osband, M.E. et al. (1990). "Problems in the Investigational Study and Clinical Use of Cancer Immunotherapy," *Immunol. Today* 11(6):193-195.

Padlan, E. A. (1996). "X-Ray Crystallography of Antibodies," In *Advances in Protein Chemistry*, Richards, F.M. et al. eds., Academic Press, Inc., 49:57-133.

Padlan, E.A. et al. (1989). "Structure of an Antibody-Antigen Complex: Crystal Structure of the HyHEL-10 Fab-lysozyme Complex," *Proc Natl Acad Sci* USA 86(15):5938-5942.

Pantophlet, R. et al. (2003). "Fine Mapping of the Interaction of Neutralizing and Nonneutralizing Monoclonal Antibodies with CD4 Binding Site of Human Immunodeficiency Virus Type 1 gp120," *Journal of Virology* 77(1):642-658.

Pantophlet, R. et al. (2003). "Hyperglycosylated Mutants of Human Immunodeficiency Virus (HIV) Type 1 Monomeric gp120 as Novel Antigens for HIV Vaccine Design," *Journal of Virology* 77(10):5889-5901.

Pardridge, W.M. (1994). "New Approaches to Drug Delivery Through the Blood-Brain Barrier," Abstract, *Trends in Biotechnology* 12:239-245.

Parrillo, J.E. (1993). "Pathogenetic Mechanisms of Septic Shock," *New England Journal of Medicine* 328(20):1471-1477.

Parry, N.R. et al. (1989). "Neutralizing Epitopes of Type O Foot-and-Mouth Disease Virus. II. Mapping Three Conformational Sites with Synthetic Peptide Reagents," *J Gen Virol.* 70:1493-1503.

Partsch, G. et al. (1998). "Upregulation of Cytokine Receptors sTNF-R55, sTNF-R75, and sIL-2R in Psoriatic Arthritis Synovial Fluid," *J. Rheumatol.* 25:105-110.

Paul, W.E. ed. (1993). "Immunoglobulins: Structure and Function" Chapter 9 In *Fundamental Immunology*, Third Edition, Raven Press Ltd.: New York, NY, pp. 292-293.

Paulus, H. (1985). "Preparation and Biomedical Applications of Bispecific Antibodies," *Behring Inst. Mitt.* 78:118-132.

Pennica, D. et al. (1984) "Human Tumour Necrosis Factor: Precursor Structure, Expression and Homology to Lymphotoxin," *Nature* 312:724-729.

Pennington, J. (1992). "TNF: Therapeutic Target in Patients with Sepsis," *ASM News* 58(9): 479-482.

Persson, M.A.A. (Mar. 1991). "Generation of Diverse High-Affinity Human Monoclonal Antibodies by Repertoire Cloning," *Proc. Natl. Acad. Sci.* USA 88:2432-2436.

Petersen, C.M. et al. (1989). "Bioactive Human Recombinant Tumor Necrosis Factor-α: An Unstable Dimer?" *Eur. J. Immunol.* 19:1887-1894.

Piguet, P.F. et al. (1987). "Tumor Necrosis Factor/Cachectin is an Effector of Skin and Gut Lesions of the Acute Phase of Graft-vs.-Host Disease," *J. Exp. Med.* 166:1280-1289.

Pini, A. et al. (1998). "Design and Use of a Phage Display Library," *The Journal of Biological Chemistry* 273(34):21769-21776.

Pless, J. et al. (1973). "Boron Tris(trifluoroacetate) for Removal of Protecting Groups in Peptide Chemistry," *Angew Chem. Int. Ed. Engl.* 12(2):147-148.

Poljak, R.J. (1991). "Structure of Antibodies and Their Complexes with Antigens," *Mol Immunol.* 28(12):1341-1345.

Potter, R. (1993). "Enzon Lines Up 11 New Alliances in a Busy Year," *Biotechnology* 11:432-433.

Present, D.H. et al. (May 6, 1999). "Infliximab For the Treatment of Fistulas in Patients with Crohn's Disease," *The New England Journal of Medicine* 340:1398-1405.

Price, K.M. et al. (1990). "The Production and Characterisation of Monoclonal Antibodies to *myc*, c-*erb* B-2 and EFG-Receptor Using a Synthetic Peptide Approach," *Dev. Biol. Stand.* 71:23-31.

Prodinger, W.M. et al. (1998). "Characterization of C3dg Binding to a Recess Formed Between Short Consensus Repeats 1 and 2 of Complement Receptor Type 2 (CR2; CD21)," *J. Immunol.* 161:4604-4610.

Rademacher, T.W. et al. (1988). "The Role of IgG Glycoforms in the Pathogenesis of Rheumatoid Arthritis," *Springer Seminars in Immunopathology* 10:231-249.

Rader, C. et al. (1998). "A Phage Display Approach for Rapid Antibody Humanization: Designed Combinatorial V Gene Libraries," *Proc. Natl. Acad. Sci.* USA 95:8910-8915.

Radford, A.J. et al. (1990). "Epitope Mapping of the *Mycobacterium bovis* Secretory Protein MPB70 Using Overlapping Peptide Analysis," *J. Gen. Microbiol.* 136:265-272.

Ramasamy, R. et al. (Sep. 1990). "Novel Cross-Reactive Epitopes on Asexual Blood Stage Antigens of *Plasmodium falciparum*," *Parasite Immunol.* 12(5):457-471.

Rankin, E.C.C. et al. (1995). "The Therapeutic Effects of an Engineered Human Anti-Tumour Necrosis Factor Alpha Antibody (CDP571) in Rheumatoid Arthritis," *Br. J. Rheumatol.* 34(4):334-342.

Rathjen, D.A. et al. (1986). "Identification of Antigenic Determinants on Insulin Recognized by Monoclonal Antibodies," *Mol. Immunol.* 23(4):441-450.

Rathjen, D.A. et al. (1991). "Antigenic Structure of Human Tumour Necrosis Factor: Recognition of Distinct Regions of TNFα by Different Tumour Cell Receptors," *Mol. Immunol.* 28(1/2):79-86.

Rathjen, D.A. et al. (Jun. 1992). "Selective Enhancement of the Tumour Necrotic Activity of TNF, with Monoclonal Antibody," *Br. J. Cancer* 65(6):852-856.

Rathjen, D.A. et al. (1993). "Differential Effects of Small Tumour Necrosis Factor-α Peptides on Tumour Cell Cytotoxicity, Neutrophil Activation and Endothelial Cell Procoagulant Activity," *Immunology* 80:293-299.

Rathjen, D.A. et al. (1993). "Selective Enhancement of Tumour Necrosis Factor Activity: Mapping Regions with Monoclonal Antibodies," *Bioorganic & Medicinal Chemistry Letters* 3(3):457-462.

Reece, J.C. et al. (Dec. 1, 1993). "Mapping the Major Human T Helper Epitopes of Tetanus Toxin: The Emerging Picture," *J. Immunol.* 151(11):6175-6184.

Reece, J.C. et al. (Jun. 24, 1994). "Scanning for T Helper Epitopes with Human PBMC using Pools of Short Synthetic Peptides," *J. Immunol. Methods.* 172(2):241-254.

Reed, C. et al. (1997). "Crystal Structure of TNF-Alpha Mutant R31D with Greater Affinity for Receptor R1 Compared with R2," *Protein Eng.* 10(10):1101-1107.

Reineke, U. (2004). "Antibody Epitope Mapping Using Arrays of Synthetic Peptides," Chapter 26 In *Methods in Molecular Biology: Antibody Engineering—Methods and Protocols*, Lo, B.K.C. ed., Humana Press, Inc.: Totowa, NJ, vol. 248, pp. 443-463.

Reineke, U. et al. (May 1996). "Mapping Protein-Protein Contact Sites Using Cellulose-Bound Peptide Scans," *Mol. Divers.* 1(3):141-148.

Reineke, U. et al. (1998). "Mapping of the Interleukin-10/interleukin-10 Receptor Combining Site," *Protein Science* 7:951-960.

Reineke, U. et al. (1999). "Antigen Sequence- and Library-Based Mapping of Linear and Discontinuous Protein-Protein-Interaction Sites by Spot Synthesis," *Current Topics in Microbiology and Immunology* 243:23-36.

Reineke, U. et al. (1999). "Evidence for Conformationally Different States of Interleukin-10: Binding of a Neutralizing Antibody Enhances Accessibility of a Hidden Epitope," *J. Mol. Recognition* 12:242-248.

Reineke, U. et al. (Mar. 1999). "A Synthetic Mimic of a Discontinuous Binding Site on Interleukin-10," *Nature Biotechnol.* 17:271-275.

Reineke, U. et al. (2001). "Applications of Peptide Arrays Prepared by the SPOT-Technology," *Current Opinion in Biotechnology* 12:59-64.

Reineke, U. et al. (2001). "Epitope Mapping with Synthetic Peptides Prepared by SPOT Synthesis," In *Antibody Engineering* (Springer Lab Manual), Kontermann/Dubel eds. pp. 433-459.

Reinhart, K. et al. (1995). "Treatment of Severe Sepsis with Anti-TNF Monoclonal Antibody MAK 195F: Dose Dependent Reduction of Mortality in Patients with Elevated IL-6 Serum-Levels," *Supplement to Clin. Intens. Care* 6(2):82 (Abstract.).

Remick, D.G. et al. (1987). "Acute in Vivo Effects of Human Recombinant Tumor Necrosis Factor," *Lab. Invest.* 56(6):583-590.

Rhein, R. (Oct. 4, 1993). "Another Sepsis Drug Down-Immunex'TNF Receptor," *Biotechnology Newswatch*, two pages.

Riechmann, L. et al. (1988). "Reshaping Human Antibodies for Therapy," *Nature* 332:323-327.

Roach, D.R. et al. (Oct. 1999). "Tumor Necrosis Factor (TNF) and a TNF-Mimetic Peptide Modulate the Granulomatous Response to *Mycobacterium bovis* BCG Infection In Vivo," *Infection and Immunity* 67(10):5473-5476.

Robinson, B.S. et al. (1999). "Effects of β-Oxa and β-Thia Polyunsaturated Fatty Acids on Agonist-Induced Increase in Endothelial Cell Adhesion Molecules," *Lipids* 34 Suppl:S341-S342.

Rodda, S.J. (2002). "Peptide Libraries to T Cell Epitope Screening and Characterization," *Journal of Immunological Methods* 267:71-77.

Rodda, S.J. et al. (1986). "The Antibody Response to Myoglobin-I. Systematic Synthesis of Myoglobin Peptides Reveals Location and Substructure of Species-Dependent Continuous Antigenic Determinants," *Mol. Immunol.* 23(6):603-610.

Rodseth, L.E. et al. (Jun. 3, 1994). "Two Crystal Forms of the Extracellular Domain of Type I Tumor Necrosis Factor Receptor," *J. Mol. Biol.* 239(2):332-335.

Różalski, M. et al. (Nov. 15, 1985). "Monoclonal Antibodies Against Histone H5. Epitope Mapping and Binding to Chromatin," *J. Biol. Chem.* 260(26):14379-14386.

Ruddle, N.H. et al. (1990). "An Antibody to Lymphotoxin and Tumor Necrosis Factor Prevents Transfer of Experimental Allergic Encephalomyelitis," *J. Exp. Med.* 172:1193-1200.

Ruff, M.R. et al. (Jan. 1981). "Rabbit Tumor Necrosis Factor: Mechanism of Action," *Infec. Immun.* 31(1):380-385.

Sagawa, Y. et al. (1993). "Is Sustained Production of Tumor Necrosis Factor-α Relevant to the Development of Pustular Psoriasis?" *Dermatology* 187:81-83.

Saiki, R.K. et al. (1985). "Enzymatic Amplification of B-Globin Genomic Sequences and Restriction Site Analysis for Diagnosis of Sickle Cell Anemia," *Science* 230:1350-1354.

Salat, C. et al. (1996). "Hemostatic Parameters in Sepsis Patients Treated With Anti-TNFα-Monoclonal Antibodies," *Shock* 6(4):233-237.

Sambrook, J. et al. (1989). "Screening Expression Libraries with Antibodies and Oligonucleotides," Chapter 12 In *Molecular Cloning: A Laboratoy Manual*, Cold Spring Harbor Laboratory Press, Cold Spring Harbor, NY, pp. 12.1-12.44.

Sato, N. et al. (Jun. 1986). "Actions of Tumor Necrosis Factor on Cultured Vascular Endothelial Cells: Morphologic Modulation, Growth Inhibition, Cytotoxicity," *JNCI* 76(6):1113-1121.

Sattayasai, N. et al. (Sep. 1991). "Subtype-Specificity of Antipeptide Antibodies Raised Against Unique Sequences of Human Interferons-α," *Mol. Immunol.* 28(9):975-983.

Sayle, R.A. et al. (1995). "RasMol: Biomolecular Graphics For All," *Trends in Biochemical Science (TIBS)* 20(9):374-376.

Scallon, B. et al. (2002). "Binding and Functional Comparisons of Two Types of Tumor Necrosis Factor Antagonists," *J. Pharmacol. Exp. Ther.* 301(2):418-426.

Scallon, B. et al. (May 2004). "Addition of an Extra Immunoglobulin Domain to Two Anti-Rodent TNF Monoclonal Antibodies Substantially Increased Their Potency," *Mol. Immunol.* 41(1):73-80.

Scallon, B.J. et al. (1995). "Chimeric Anti-TNF-α Monoclonal Antibody cA2 Binds Recombinant Transmembrane TNF-α and Activates Immune Effector Functions," *Cytokine* 7(3):251-259.

Scanlan, C.N. et al. (Jul. 2002). "The Broadly Neutralizing Anti-Human Immunodeficiency Virus Type 1 Antibody 2G12 Recognizes a Cluster of α1→2 Mannose Residues on the Outer Face of gp120," *Journal of Virology* 76(14):7306-7321.

Schall, T. et al. (1990). "Molecular Cloning and Expression of a Receptor for Human Tumor Necrosis Factor," *Cell* 61:361-370.

Scheurich, P. et al. (1986). "Quantification and Characterization of High-Affinity Membrane Receptors for Tumor Necrosis Factor on Human Leukemic Cell Lines," *Int. J. Cancer* 38:127-133.

Schier, R. et al. (1995). "In vitro and in vivo Characterization of a Human Anti-c-erbB-2 Single-Chain Fv Isolated From a Filamentous Phage Antibody Library," *Immunotechnology* 1:73-81.

Schlayer, H.-J. et al. (1987). "Enhancement of Neutrophil Adherence to Isolated Rat Liver Sinusoidal Endothelial Cells by Supernatants of Lipopolysaccharide-Activated Monocytes," *J. Hepatol.* 5:311-321.

Schmidt, T. (1996). "Molecular Interaction Between the *Strep-* Tag Affinity Peptide and its Cognate Target, Streptavidin," *J. Mol. Biol.* 255:753-766.

Schoofs, P.G. et al. (Jan. 15, 1988). "Epitopes of an Influenza Viral Peptide Recognized by Antibody at Single Amino Acid Resolution," *J. Immunol.* 140(2):611-616.

Schreiber, M. et al. (Dec. 1997). "The V3-Directed Immune Response in Natural Human Immunodeficiency Virus Type 1 Infection is Predominantly Directed Against a Variable, Discontinuous Epitope Presented by the gp120 V3 Domain," *J. Virol.* 71(12):9198-9205.

Schwenger, P. et al. (1996). "Inhibition of Tumor Necrosis Factor-Induced p42/p44 Mitogen Activated Protein Kinase Activation by Sodium Salicylate," *The Journal of Biological Chemistry* 271(14):8089-8094.

Seckinger, P. et al. (1989). "Purification and Biologic Characterization of a Specific Tumor Necrosis Factor α Inhibitor," *The Journal of Biological Chemistry* 264(20):11966-11973.

Selinsky, C.L. et al. (1998). "Multifaceted Inhibition of Anti-Tumour Immune Mechanisms By Soluble Tumour Necrosis Factor Receptor Type I," *Immunology* 94:88-93.

Selmaj, K. et al. (1987). "Tumor Necrosis Factor Mediates Myelin Damage in Organotypic Cultures of Nervous Tissue," Abstract, *Journal of Neuroimmunology* 16(1):159.

Selmaj, K. et al. (1991). "Anti-Tumor Necrosis Factor Therapy Abrogates Autoimmune Demyelination," *Ann. Neurol.* 30:694-700.

Selvey, L.A. et al. (Nov. 1, 1990). "Identification of B-Epitopes in the Human Papillomavirus 18 E7 Open Reading Frame Protein," *J. Immunol.* 145(9):3105-3110.

Shalaby, M.R. et al. (1988). "The Involvement of Human Tumor Necrosis Factors α and β in the Mixed Lymphocyte Reaction," *J. Immunol.* 141(2):499-503.

Shalaby, M.R. et al. (1989). "Prevention of the Graft-Versus-Host Reaction in Newborn Mice by Antibodies to Tumor Necrosis Factor-Alpha," *Transplantation* 47(6):1057-1061.

Shalaby, M.R. et al. (1992). "Development of Humanized Bispecific Antibodies Reactive with Cytotoxic Lymphocytes and Tumor Cells Overexpressing the *HER2* Protooncogene," *J. Exp. Med.* 175:217-225.

Shearman, C.W. et al. (1991). "Construction, Expression and Characterization of Humanized Antibodies Directed Against the Human α/β T Cell Receptor," *The Journal of Immunology* 147(12):4366-4373.

Sheehan, K. et al. (1989). "Generation and Characterization of Hamster Monoclonal Antibodies that Neutralize Murine Tumor Necrosis Factors," *J. Immunol.* 142(11):3884-3893.

Sheriff, S. et al. (1987). "Three-Dimensional Structure of an Antibody-Antigen Complex," *Proc. Natl. Acad. Sci. USA.* 84(22):8075-8079.

Shimamoto, Y. et al. (1988). "Monoclonal Antibodies Against Human Recombinant Tumor Necrosis Factor: Prevention of Endotoxic Shock," *Immunology Letters* 17:311-318.

Shukla, D.D. et al. (Nov. 1989). "Localization of Virus-Specific and Group-Specific Epitopes of Plant Potyviruses by Systematic Immunochemical Analysis of Overlapping Peptide Fragments," *Proc. Natl. Acad. Sci. USA* 86(21):8192-8196.

Siegel, S.A. et al. (1995). "The Mouse/Human Chimeric Monoclonal Antibody cA2 Neutralizes TNF in Vitro and Protects Transgenic Mice from Cachexia and TNF Lethality in Vivo," *Cytokine* 7(1):15-25.

Silva, A.T. (1990). "Prophylactic and Therapeutic Effects of a Monoclonal Antibody to Tumor Necrosis Factor α in Experimental Gram-Negative Shock," *J. Infect. Dis.* 162:421-427.

Simkins, R.A. et al. (1989). "Epitope Mapping and the Detection of Transmissible Gastroenteritis Viral Proteins in Cell Culture Using Biotinylated Monoclonal Antibodies in a Fixed-Cell ELISA," *Arch. Virol.* 107(3-4):179-190.

Simpson, S.Q. et al. (1989). "Role of Tumor Necrosis Factor in Sepsis and Acute Lung Injury," *Critical Care Clinics* 5(1):27-47.

Slootstra, J.W. et al. (1995). "Structural Aspects of Antibody-Antigen Interaction Revealed Through Small Random Peptide Libraries," *Molecular Diversity* 1:87-96.

Slootstra, J.W. et al. (Oct. 1995). "Possible Active Site of the Sweet-Tasting Protein Thaumatin," *Chem. Senses* 20:535-543.

Slootstra, J.W. et al. (1996). "Identification of New Tag Sequences with Differential and Selective Recognition Properties for the Anti-FLAG Monoclonal Antibodies M1, M2, and M5," *Mol. Divers.* 2:156-164.

Slootstra, J.W. et al. (Oct. 1997). "Screening of a Small Set of Random Peptides: A New Strategy to Identify Synthetic Peptides that Mimic Epitopes," *J. Mol. Recognit.* 10:217-224.

Sluyser, M. et al. (1992). "Influence of Estrogen Receptor Variants in Mammary Carcinomas on the Prognostic Reliability of the Receptor Assay," *Mol. & Cell. Endocrinol.* 85:83-88.

Smith, C.A. et al. (1990). "A Receptor for Tumor Necrosis Factor Defines an Unusual Family of Cellular and Viral Proteins," *Science* 248:1019-1023.

Smith, R.A. et al. (Nov. 15, 1986). "Species Specificity of Human and Murine Tumor Necrosis Factor," *J. Biol. Chem.* 261(32):14871-14874.

Smith, R.A. et al. (May 25, 1987). "The Active Form of Tumor Necrosis Factor is a Trimer," *J. Biol. Chem.* 262(15):6951-6954.

Snijders, A. et al. (1991). "Identification of Linear Epitopes on Semliki Forest Virus E2 Membrane Protein and Their Effectiveness as a Synthetic Peptide Vaccine," *J. Gen Virol.* 72:557-565.

Socher, S.H. et al. (Dec. 1987) "Antibodies Against Amino Acids 1-15 Tumor Necrosis Factor Block its Binding to Cell-Surface Receptor," *Proc. Natl. Acad. Sci. USA Biochemistry* 84:8829-8833.

Sprang, S.R. et al. (1990). "Subunit Interactions and the Function of Tumor Necrosis Factor" Chapter 35 In *Current Research in Protein Chemistry: Techniques, Structure, Function*, Villafranca, J. J. ed., Academic Press, Inc.: San Diego, CA, pp. 383-394.

Sprang, S.R. et al. (1992). "The 3-D Structure of TNF" Chapter 2 In *Tumor Necrosis Factors: The Molecules and Their Emerging Role In Medicine*, Beutler, B. ed., Raven Press Ltd.: New York, NY, pp. 11-32.

Stack, W.A. et al. (1997). "Randomised Controlled Trial of CDP571 Antibody to Tumour Necrosis Factor-α in Crohn's Disease," *The Lancet* 349:521-524.

Stanfield, R.L. et al. (1995). "Protein-Peptide Interactions," *Curr. Opin. Stuc. Biol.* 5:103-113.

Starnes, H.F. Jr. et al. (1990). "ANTI-IL-6 Monoclonal Antibodies Protect Against Lethal *Escherichia coli* Infection and Lethal Tumor Necrosis Factor-α Challenge in Mice," *J. Immunol.* 145(12):4185-4191.

Stigler, R. et al. (1995). "Interaction Between a Fab Fragment Against gp41 of Human Immunodeficiency Virus 1 and its Peptide Epitope: Characterization Using a Peptide Epitope Library and Molecular Modeling," *Protein Eng.* 8:471-479.

Sugarman, B.J. et al. (Nov. 22, 1985). "Recombinant Human Tumor Necrosis Factor-α: Effects on Proliferation of Normal and Transformed Cells in Vitro," *Science* 230:943-945.

Sun, X-M. et al. (1988). "Bowel Necrosis Induced by Tumor Necrosis Factor in Rats is Mediated by Platelet-Activating Factor," *J. Clin. Invest.* 81:1328-1331.

Sunahara, N. et al. (1988). "Simple Enzyme Immunoassay Methods for Recombinant Human Tumor Necrosis Factor α and its Antibodies Using A Bacterial Cell Wall Carrier," *J. Immol. Methods* 109:203-214.

Tainer, J.A. et al. (1991). "Defining Antibody-Antigen Recognition: Towards Engineered Antibodies and Epitopes," *Int. Rev. Immunol.* 7:165-188.

Targan, S.R. et al. (1997). "A Short-Term Study of Chimeric Monoclonal Antibody cA2 to Tumor Necrosis Factor α For Crohn's Disease," *New England Journal of Medicine* 337(15):1029-1035.

Tavernier, J. et al. 1990). "Analysis of the Structure-Function Relationship of Tumour Necrosis Factor. Human/Mouse Chimeric TNF Proteins: General Properties and Epitope Analysis," *J. Mol. Biol.* 211:493-501.

Tempest, P.R. et al. (Jun. 1994). "A Humanized Anti-Tumor Necrosis Factor-α Monoclonal Antibody That Acts as a Partial, Competitive Antagonist of the Template Antibody," *Hybridoma* 13(3):183-190.

ten Hove, T. et al. (2002). "Infliximab Treatment Induces Apoptosis of Lamina Propria T Lymphocytes in Crohn's Disease," *Gut* 50:206-211.

Timmerman, P. et al. (2004). "Mapping of a Discontinuous and Highly Conformational Binding Site on Follicle Stimulating Hormone Subunit-Beta (FSH-Beta) Using Domain Scan and Matrix Scan Technology," *Mol. Divers.* 8:61-77.

Tindle, R.W. et al. (Jun. 1990). "Identification of B Epitopes in Human papillomavirus Type 16 E7 Open Reading Frame Protein," *J. Gen. Virol.* 71(Pt. 6):1347-1354.

Tomlinson, I.M. et al. (1992). "The Repertoire of Human Germline $V_H$ Sequences Reveals About Fifty Groups of $V_H$ Segments with Different Hypervariable Loops," *J. Mol. Biol.* 227:776-798.

Tracey, K.J. et al. (1986). "Shock and Tissue Injury Induced by Recombinant Human Cachectin," *Science* 234:470-474.

Tracey, K.J. et al. (1987). "Anti-cachectin/TNF Monoclonal Antibodies Prevent Septic Shock During Lethal Bacteraemia," *Nature* 330:662-664.

Trentham, D.E. (1991). "Immunotherapy and Other Novel Therapies," *Current Opinion in Rheumatology* 3:369-372.

Triantafyllou, B. et al. (Aug.-Dec. 1992). "Use of the Multipin Peptide Synthesis Technique for the Generation of Antipeptide Sera," *Cell Biophys.* 21(1-3):33-52.

Tribbick, G. (2002). "Multipin Peptide Libraries for Antibody and Receptor Epitope Screening and Characterization," *Journal of Immunological Methods* 267:27-35.

Tribbick, G. et al. (Jun. 3, 1991). "Systematic Fractionation of Serum Antibodies Using Multiple Antigen Homologous Peptides as Affinity Ligands," *J. Immunol. Methods.* 139(2):155-166.

Trifilieff, E. et al. (1991). "Antigenic Cross-Reactivity Potential of Synthetic Peptides Immobilized on Polyethylene Rods," *Mol. Immunol.* 28(8):889-896.

Truyens, C. et al. (Nov. 1999). "The Endogenous Balance of Soluble Tumor Necrosis Factor Receptors and Tumor Necrosis Factor Modulates Cachexia and Mortality in Mice Acutely Infected with *Trypanosoma cruzi*," *Infect Immun.* 67:5579-5586.

Tyutyulkova, S. et al. (May-Jun. 1994). "Selection of Functional Human Immunoglobulin Light Chains from a Phage-Display Library," *Appl. Biochem. Biotechnol.* 47(2-3):191-197.

Underwood, J.R. et al. (1994). "Monoclonal Anti-H1 Histone Autoantibodies From Unimmunized Balb/c Mice. Specificity and $V_H$ and $V_L$ Domain Sequences," *Journal of Autoimmunity* 7:291-320.

Vajdos, F.F. et al. (2002). "Comprehensive Functional Maps of the Antigen-Binding Site of an Anti-ErbB2 Antibody Obtained with Shotgun Scanning Mutagenesis," *J. Mol. Biol.* 320:415-428.

Valle, M. et al. (1999). "Selection of Antibody Proves to Correlate Protein Sequence Domains with Their Structural Distribution," *Prot. Sci.* 8:883-889.

Van Amerongen, A. et al. (1994). "Design of Peptides With Improved Affinities for Anti-Human Chorionic Gonadotropin Monoclonal Antibodies," *Peptide Res.* 7(2):83-90.

Van der Goot, F.G. et al. (1999). "Membrane Interaction of TNF in Not Sufficient to Trigger Increase in Membrane Conductance in Mammalian Cells," *FEBS Lett.* 460:107-111.

Van der Heijde, D.M.F.M. et al. (Jan. 1992). "Biannual Radiographic Assessments of Hands and Feet in a Three-Year Prospective Followup of Patients With Early Rheumatoid Arthritis," *Arthritis and Rheumatism* 35(1):26-34.

Van der Poll, T. et al. (1991). "Tumor Necrosis Factor and the Disbalance Between Coagulant and Anticoagulant Mechanisms in Septicemia" In *Update In Intensive Care and Emergency Medicine* 14, Vincent, J.L. ed., Springer-Verlar: Berlin, pp. 269-273.

Van der Poll, T. et al. (1994). "Differential Effects of Anti-Tumor Necrosis Factor Monoclonal Antibodies on Systemic Inflammatory Responses in Experimental Endotoxemia in Chimpanzees," *Blood* 83:446-451.

Van Deventer, S.J.H. et al. (1990). "Experimental Endotoxinemia in Humans: Analysis of Cytokine Release and Coagulation, Fibrinolytic, and Complement Pathway," *Blood* 76:2520-2526.

Van Dolleweerd, C.J. et al. (May 21, 2004). "Peptide Mapping of a Novel Discontinuous Epitope of the Major Surface Adhesion From *Streptococcus mutans*," *The Journal of Biological Chemistry* 279(21):22198-22203.

Van Dulleman, H.M. et al. (1995). "Treatment of Crohn's Disease with Anti-Tumour Necrosis Factor Chimeric Monoclonal Antibody (cA2)," *Gastroenterology* 109(1):129-135.

Van Oosten, B.W. et al. (1996). "Increased MRI Activity and Immune Activation in Two Multiple Sclerosis Patients Treated with the Monoclonal Anti-Tumor Necrosis Factor Antibody cA2," *Neurology* 47:1531-1534.

Van Oosten, B.W. et al. (1997). "Treatment of Multiple Sclerosis with the Monoclonal Anti-CD4 An tibody cM-T412: Results of a Randomized, Double-Blind, Placebo-Controlled, MR-Monitored Phase II Trial," Abstract, *Neurology* 49(2):351-357.

van Ostade, X. et al. (1991). "Localization of the Active Site of Human Tumour Necrosis Factor (hTNF) by Mutational Analysis," *The EMBO Journal* 10(4):827-836.

van Ostade, X. et al. (1993). "Human TNF Mutants With Selective Activity on the p55 Receptor," *Nature* 361:266-269.

van Ostade, X. et al. (1994). "Human Tumor Necrosis Factor Mutants with Preferential Binding to and Activity on Either the R55 or R75 Receptor," *Eur. J. Biochem.* 220:771-779.

van Ostade, X. et al. (1994). "Structure-Activity Studies of Human Tumour Necrosis Factors," *Protein Eng.* 7(1):5-22.

van Regenmortel, M.H.V. (1989). "The Concept and Operational Definition of Protein Epitopes," *Phil. Trans. R. Soc. Lond. B* 323:451-466.

van Regenmortel, M.H.V. (1989). "Structural and Functional Approaches to the Study of Protein Antigenicity," *Immunology Today* 10(8):266-272.

van Regenmortel, M.H.V. et al. (1988). "Operational Aspects of Epitope Identification: Structural Features of Proteins Recognized by Antibodies," In *Vaccines: New Concepts and Developments*, Kohler, H. et al. ed., Longman Scientific & Technical, pp. 113-122.

Vandenbeele, P. et al. (1995). "Two Tumour Necrosis Factor Receptors: Structure and Function," *Trends in Cell Biology* 5:392-399.

Vaughan, T.J. et al. (1996). "Human Antibodies With Sub-Nanomolar Affinities Isolated From a Large Non-Immunized Phage Display Library," *Nature Biotechnology* 14:309-314.

Verhoef, J. et al. (1990). "Prospects for Monoclonal Antibodies in the Diagnosis and Treatment of Bacterial Infections," *Eur. J. Clin. Microbiol. Infect. Dis.* 9(4): 247-250.

Verma, I.M. et al. (1997). "Gene Therapy—Promises, Problems and Prospects," *Nature* 389:239-242.

Vilcek, J. (1998). "The Cytokines: An Overview" Chapter 1 In *The Cytokine Handbook*, Third Edition, Academic Press Ltd., pp. 1-20.

Vilcek, J. et al. (1986). "Fibroblast Growth Enhancing Activity of Tumor Necrosis Factor and its Relationship to Other Polypeptide Growth Factors," *J. Exp. Med.* 163:632-643.

Villard, S. et al. (Jul. 26, 2002). "Low Molecular Weight Peptides Restore the Procoagulant Activity of Factor VIII in the Presence of the Potent Inhibitor Antibody ESH8," *J. Biol. Chem.* 277(30):27232-27239.

Vodyanik, M.A. et al. (2001). "Application of Cooperative Monoclonal Antibodies in the Enzyme Immunoassay for Detection of Human Tumor Necrosis Factor," *Uk Biokhim Zh.* 73(6):77-83. (Only Abstract in English.).

Vodyanik, M.A. et al. (2001). "Functional Properties of Cooperative Monoclonal Antibodies Against Human Tumor Necrosis Factor," *Fiziol Zh.* 47(3):73-79. (Only Abstract in English.).

Von Asmuth, E.J.U. et al. (1990). "Tumour Necrosis Factor Alpha (TNF-α) and Interleukin 6 in a Zymosan-Induced Shock Model," *Scand. J. Immunol.* 32:313-319.

Waldmann, T.A. (1991). "Monoclonal Antibodies in Diagnosis and Therapy," *Science* 252:1657-1662.

Walker, R.E. (1996). "Inhibition of Immunoreactive Tumor Necrosis Factor-Alpha by a Chimeric Antibody in Patients Infected with Human Immunodeficiency Virus Type 1," *Journal of Infect. Dis.* 174(1):63-68.

Wallach, D. et al. (1999). "Tumor Necrosis Factor Receptor and Fas Signaling Mechanisms," *Annu. Rev. Immunol.* 17:331-367.

Ward, S.E. et al. (1989). "Binding Activities of a Repertoire of Single Immunoglobulin Variable Domains Secreted from *Escherichia coli*," *Nature* 341:544-546.

Ware, C.F. et al. (1998). "Tumor Necrosis Factor-Related Ligands and Receptors" Chapter 20 In *The Cytokine Handbook*, Third Edition, Academic Press Ltd., pp. 549-592.

Watanabe, N. et al. (1986). "Analysis of the TNF Receptors of kym cells by affinity cross-linking," Japanese article from *Gan To Kagaku Ryoho* (*Jpn. J. Cancer Chemotherapy*) 13(8):2625-2629, and English translation, 5 pages.

Watanabe, N. et al. (1988). "Synergistic Cytotoxicity of Recombinant Human TNF and Various Anti-Cancer Drugs," *Immunopharmacol. Immunotoxicol.* 10(1):117-127.

Welschof, M. et al. (1999). "The Antigen Binding Domain of Non-Idiotype Human Anti-F(ab')2 Autoantibodies: Study of Their Interaction with IgG Hinge Region Epitopes," *Hum Immunol.* 60:282-290.

Westhoff, W.E. et al. (May 1996). "Detection of Epitopes on Follicle-Stimulating Hormone and FSH-Antiserum-Induced Suppression of Bioactivity of Follicle-Stimulating Hormone and Luteinizing Hormone," *J. Reprod. Immunol.* 30:133-149.

Whittle, N. et al. (1989). "Construction and Expression of a CDR-Grafter Anti-TNF Antibody," Abstract A342, *J. Cell Biochem.* Supl. 13A:96.

Wilson, I.A. et al. (Aug. 1985). "Identical Short Peptide Sequences in Unrelated Proteins Can Have Different Conformations: A Testing Ground for Theories of Immune Recognition," *Proc. Natl. Acad. Sci. USA* '82:5255-5259.

Wilson, I.A. et al. (1993). "Antibody-Antigen Interaction," *Current Opinion in Structural Biology* 3:113-118.

Winter, G. et al. (1991). "Man-made Antibodies," *Nature* 349(6307):293-299.

Winter, G. et al. (1993). "Humanized Antibodies," *Immunology Today* 14(6):243-245.

Winter, G. et al. (1994). "Making Antibodies by Phage Display Technology," *Annu. Rev. Immunol.* 12:433-455.

Wobus, C.E. et al. (Oct. 2000). "Monoclonal Antibodies Against the Adeno-Associated Virus Type 2 (AAV-2) Capsid: Epitope Mapping and Identification of Capsid Domains Involved in AAV-2-Cell Interaction and Neutralization of AAV-2 Infection," *J. Virology* 74(19):9281-9293.

Wood, P.R. et al. (Sep. 1988). "Production and Characterization of Monoclonal Antibodies Specific for *Mycobacterium bovis*," *J. Gen. Microbiol.* 134(1):2599-2604.

Woof, J.M. et al. (1986). "Localisation of the Monocyte-Binding Region on Human Immunoglobulin G," *Molec. Immunol.* 23(3):319-330.

Yamagishi, J-I. et al. (1990). "Mutational Analysis of Structure—Activity Relationships in Human Tumor Necrosis Factor-Alpha," *Prot. Eng.* 3(8):713-719.

Yamamoto, R. et al. (1989). "Histidine-15: An Important Role in the Cytotoxic Activity of Human Tumor Necrosis Factor," *Protein Eng.* 12(7):553-558.

Yamauchi et al. (1989). "Intracellular Hydroxyl Radical Production Induced by Recombinant Human Tumor Necrosis Factor and Its Implication in the Killing of Tumor Cell In Vitro," *Cancer Res.* 49:1671-1675.

Yamazaki, S. et al. (1986). "Proposal of Standardized Methods and Reference For Assaying Recombinant Human Tumor Necrosis Factor," *Jap. J. Med. Sci. Biol.* 39:105-118.

Yan, L. et al. (1991). "Preparation and Characterization of Monoclonal Antibodies Against Recombinant Human Tumor Necrosis Factor Alpha," *Chinese J. of Biotechnology* 7(2):121-126.

Yang, W.P. et al. (1995). "CDR Walking Mutagenesis for the Affinity Maturation of a Potent Human Anti-HIV-1 Antibody into the Picomolar Range," *J. Mol. Biol.* 254(3):392-403.

Yokota, S-I. et al. (1996). "A Polyreactive Human Anti-Lipid A Monoclonal Antibody Having Cross Reactivity to Polysaccharide Portions of *Pseudomonas aeruginosa* Lipopolysaccharides," *FEMS Immunology and Medical Microbiology* 14:31-38.

Yone, K. et al. (Aug. 18, 1995). "Epitopic Regions for Antibodies Against Tumor Necrosis Factor α," *J. Biol. Chem.* 270(33):19509-19515.

Zebedee, S.L. et al. (1992). "Human Combinatorial Antibody Libraries to Hepatitis B Surface Antigen," *Proc. Natl. Acad. Sci. USA* 89:3175-3179.

Zeder-Lutz, G. et al. (Feb. 1993). "Monoclonal Antipeptide Antibodies: Affinity and Kinetic Rate Constants Measured for the Peptide and the Cognate Protein Using a Biosensor Technology," *Mol. Immunol.* 30(2):145-155.

Zhang, M. et al. (1998). "Tumor Necrosis Factor" Chapter 19 In *The Cytokine Handbook*, Third Edition, Academic Press Ltd., pp. 517-547.

Zhang, X-M. et al. (1992). "Site-Directed Mutational Analysis of Human Tumor Necrosis Factor-α Receptor Binding Site and Structure-Functional Relationship," *J. Biol. Chem.* 267(33):24069-24075.

Zwick, M.B. et al. (Jun. 2003). "A Novel Human Antibody Against Human Immunodeficiency Virus Type 1 gp120 Is V1, V2, and V3 Loop Dependent and Helps Delimit the Epitope of the Broadly Neutralizing Antibody Immunoglobulin G1 b12," *Journal of Virology* 77(12):6965-6978.

Zwierzina, H. (1993). "Practical Aspects of Cytokine Therapy," *Stem Cells* 11:144-153.

Non-Final Office Action mailed Feb. 23, 2007, for U.S. Appl. No. 11/362,327, filed Feb. 23, 2006, 15 pages.

Non-Final Office Action mailed Oct. 11, 2007, for U.S. Appl. No. 11/362,327, filed Feb. 23, 2006, 10 pages.

Non-Final Office Action mailed Mar. 4, 2008, for U.S. Appl. No. 11/737,608, filed Apr. 19, 2007, eight pages.

Non-Final Office Action mailed Jul. 3, 2008, for U.S. Appl. No. 11/362,327, filed Feb. 23, 2006, eight pages.

Non-Final Office Action mailed Oct. 30, 2008, for U.S. Appl. No. 11/761,228, filed Jun. 11, 2007, 11 pages.

* cited by examiner

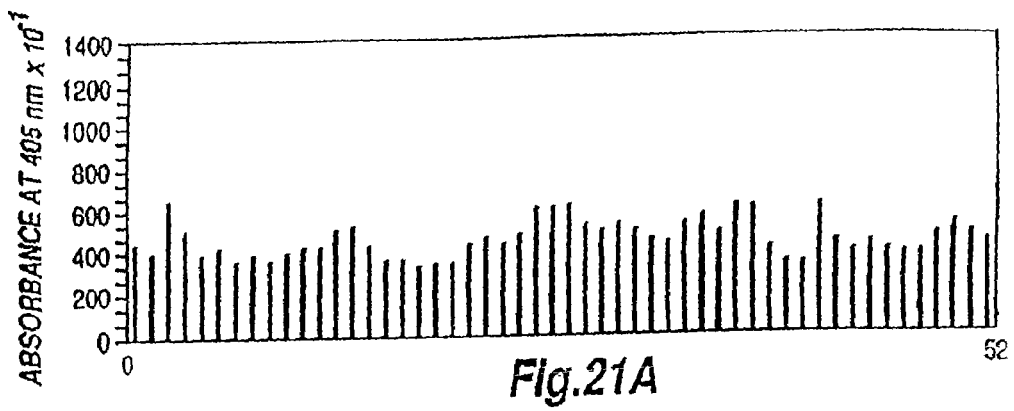
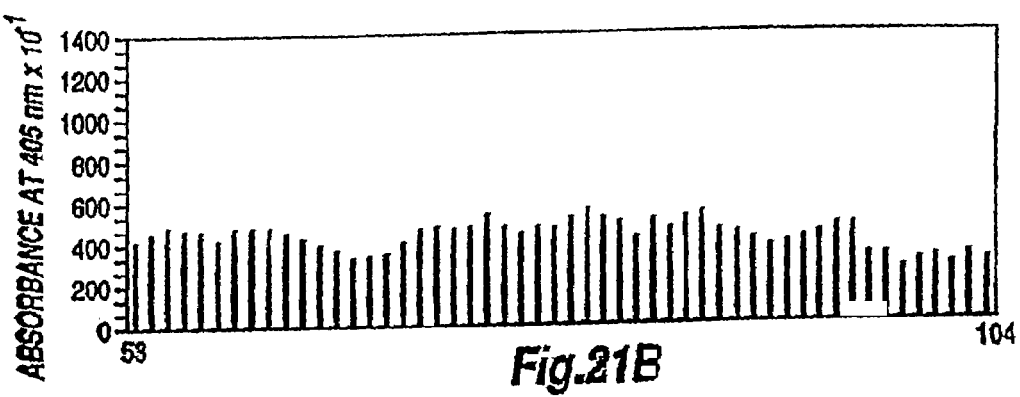
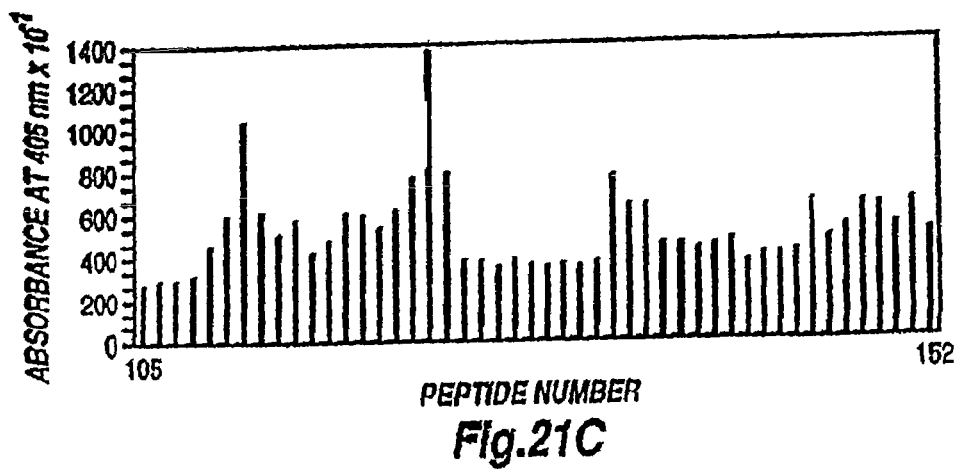

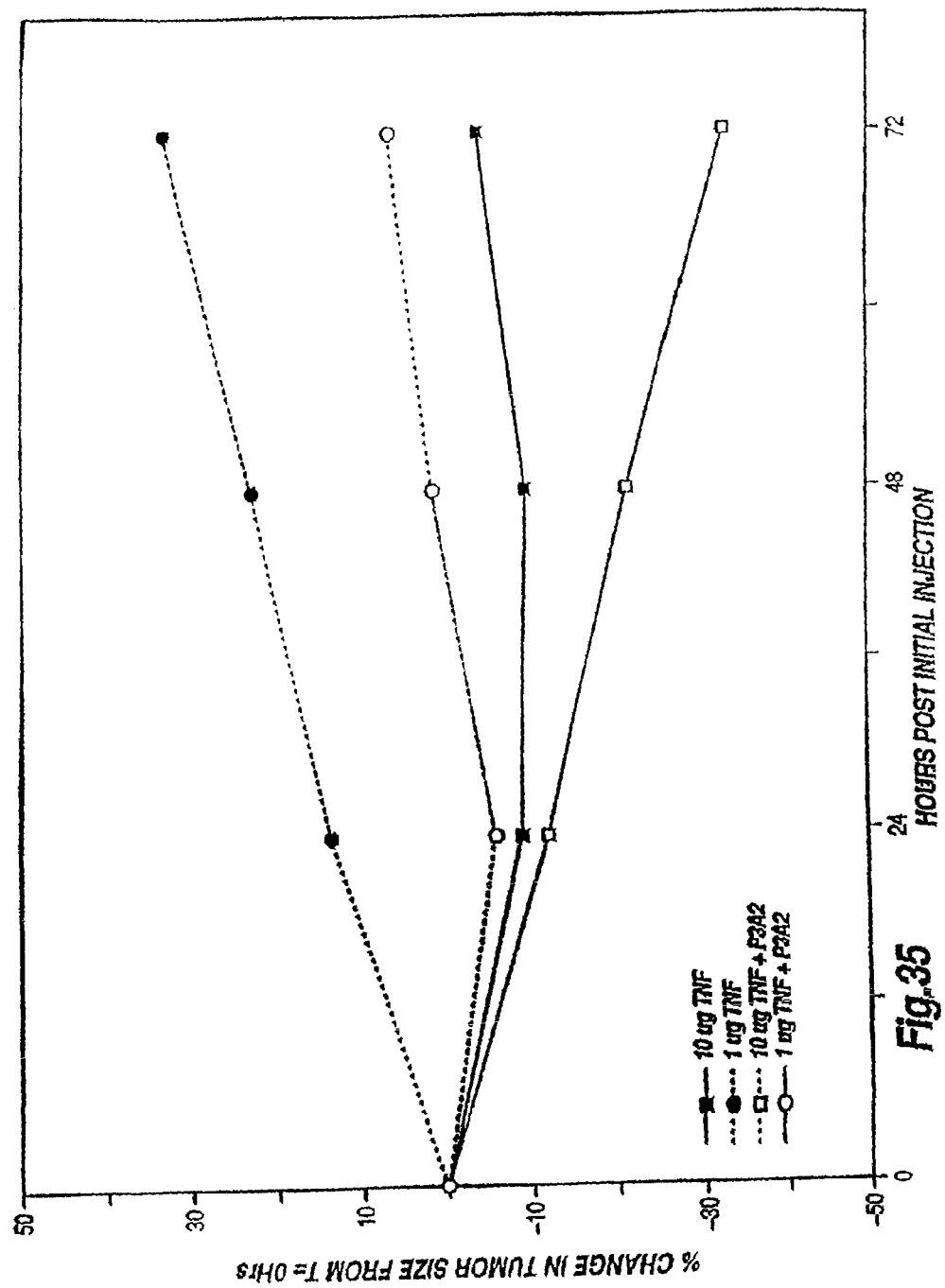

TUMOUR NECROSIS FACTOR BINDING LIGANDS

CROSS REFERENCE TO RELATED APPLICATIONS

This application is a continuation of application Ser. No. 11/326,996, filed Jan. 5, 2006, which is a continuation of application Ser. No. 10/702,681, filed Nov. 5, 2003 (now abandoned), which is a continuation of application Ser. No. 10/453,176, filed Jun. 2, 2003 (now abandoned), which is a continuation of application Ser. No. 10/359,934, filed Feb. 7, 2003 (now abandoned), which is a continuation of application Ser. No. 10/327,541, filed Dec. 20, 2002 (now abandoned), which is a continuation of application Ser. No. 10/265,451 (now abandoned), filed Oct. 3, 2002, which is a continuation of application Ser. No. 09/736,630 (now U.S. Pat. No. 6,593,458), filed Dec. 13, 2000, which is a continuation of application Ser. No. 09/364,039 (now U.S. Pat. No. 6,416,757), filed July 30, 1999, which is a continuation of application Ser. No. 08/823,893, filed Mar. 17, 1997 (now U.S. Pat. No. 5,959,087), which is a continuation of application Ser. No. 08/344,133, filed Nov. 23, 1994 (now U.S. Pat. No. 5,644,034), which is a continuation-in-part of application Ser. No. 07/828,956, filed Feb. 18, 1992 (now abandoned), which is a national phase filing of international application PCT/AU90/00337, filed 7 Aug. 1990, published in English on Feb. 21, 1991, which claims the benefit of Australian applications AU PJ5662, filed Aug. 7, 1989, and AU PJ7576, filed Nov. 24, 1989, the disclosures of which are incorporated herein by reference in their entirety.

FIELD OF THE INVENTION

The present invention relates to ligands which bind to human tumour necrosis factor alpha (TNF) in a manner such that upon binding the biological activity of TNF is modified. The type of modification shown here is distinct from previous descriptions of antibodies which bind to TNF alpha and inhibit all TNF alpha activity. The new discovery shows how the different activities of TNF alpha can be selectively inhibited or enhanced. In addition, the present invention relates to a composition comprising a molecule bound to TNF and to methods of therapy utilising TNF and molecules active against TNF.

BACKGROUND OF THE INVENTION

Tumor necrosis factor alpha (TNF) is a product of activated macrophages first observed in the serum of experimental animals presensitized with *Bacillus Calmette-Guerin* or *Corynebacterium parvum* and challenged with endotoxin (LPS). Following the systematic administration of TNF haemorrhagic necrosis was observed in some transplantable tumours of mice while in vitro TNF caused cytolytic or cytostatic effects on tumour cell lines.

In addition to its host-protective effect, TNF has been implicated as the causative agent of pathological changes in septicemia, cachexia and cerebral malaria. Passive immunization of mice with a polyclonal rabbit serum against TNF has been shown to protect mice against the lethal effects of LPS endotoxin, the initiating agent of toxic shock, when administered prior to infection.

The gene encoding TNF had been cloned allowing the usefulness of this monokine as a potential cancer therapy agent to be assessed. While TNF infusion into cancer patients in stage 1 clinical trials has resulted in tumour regression, side-effects such as thrombocytopaenia, lymphocytopaenia hepatotoxicity, renal impairment and hypertension have also been reported. These quite significant side-effects associated with the clinical use of TNF are predictable in view of the many known effects of TNF, some of which are listed in Table 1.

TABLE 1

BIOLOGICAL ACTIVITIES OF TNF

ANTI-TUMOUR
ANTI-VIRAL
ANTI-PARASITE
FUNCTION cytotoxic action on tumour cells
pyrogenic activity
angiogenic activity
inhibition of lipoprotein lipase
activation of neutrophils
osteoclast activation
induction of endothelial, monocyte and tumour cell procoagulant activity
induction of surface antigens on endothelial cells
induction of IL-6
induction of c-myc and c-fos
induction of EGF receptor
induction of IL-1
induction of TNF synthesis
induction of GM-CSF synthesis
increased prostaglandin and collagenase synthesis
induction of acute phase protein C3

Of particular importance is the activation of coagulation which occurs au a consequence of TNF activation of endothelium and also peripheral blood monocytes. Disseminated intravascular coagulation is associated with toxic shock and many cancers including gastro-intestinal cancer, cancer of the pancreas, prostate, lung, breast and ovary, melanoma, acute leukaemia, myeloma, myeloproliferative syndrome and myeloblastic leukaemia. Clearly modifications of TNF activity such that tumour regression activity remains intact but other undesirable effects such as activation of coagulation are removed or masked would lead to a more to advantageous cancer therapy, while complete abrogation of TNF activity is sought for successful treatment of toxic shock.

Segregation of hormonal activity through the use of site-specific antibodies (both polyclonal and monoclonal) can result in enhanced hormonal activity (Aston et al, 1989, Mol. Immunol. 26, 435). To date few attempts have been made to assign antigenicity or function to particular regions of the TNF molecule for which the three-dimensional structure is now known. Assignment of function to such regions would permit the development of MAbs and other ligands of therapeutic use. Polyclonal antibodies to amino acids 1 to 15 have been reported to block Hela R19 cell receptor binding by TNF (Socher et al, 1987, PNAS 84, 8829) whilst monoclonal antibodies recognising undefined conformational epitopes on TNF have been shown to inhibit TNF cytotoxicity in vitro (Bringman and Aggarwal, 1987, Hybridoma 6, 489). However, the effects of these antibodies on other TNF activities is unknown.

SUMMARY OF THE PRESENT INVENTION

The present inventors have produced panels of monoclonal antibodies active against human TNF and have characterised them with respect to their effects on the anti-tumour effect of TNF (both in vitro and in vivo), TNF receptor binding, activation of coagulation (both in vitro and in vivo) and defined their topographic specificities. This approach has led the inventors to show that different topographic regions of TNF alpha are associated with different activities. Therefore the inventors enable the identification of antibodies or ligands which selectively enhance or inhibit TNF alpha activity, thereby providing for improved therapeutic agents and regimes including TNF alpha.

In a first aspect the present invention consists in a ligand capable of binding to human TNF, the ligand being characterised in that when it binds to TNF the following biological activities of the TNF are inhibited:

1. Tumour regression;
2. Induction of endothelial procoagulant;
3. Induction of tumour fibrin deposition;
4. Cytotoxicity; and
5. Receptor binding.

In a preferred embodiment of all aspects the present invention the ligand is selected from the group consisting of antibodies, F(ab) fragments restructured antibodies (CDR grafted humanized antibodies) single domain antibodies (dAbs), single chain antibodies, serum binding proteins, receptors and natural inhibitors. The ligand may also be a protein or peptide which has been synthesized and which is analogous to one of the foregoing fragments. However, it is presently preferred that the ligand is a monoclonal antibody or F(ab) fragment thereof.

In a second aspect the present invention consists in a ligand capable of binding to human TNF, the ligand being characterized in that when it binds to TNF the induction of endothelial procoagulant, tumour regression, induction of tumour fibrin deposition, cytotoxicity and receptor binding activities of the TNF are inhibited, the ligand binding to the TNF such that the epitope of the TNF defined by the topographic regions of residues 1-18 ($Val_1$-$Arg_2$-$Ser_3$-$Ser_4$-$Ser_5$-$Arg_6$-$Thr_7$-$Pro_8$-$Ser_9$-$Asp_{10}$-$Lys_{11}$-$Pro_{12}$-$Val_{13}$-$Ala_{14}$-$His_{15}$-$Val_{16}$-$Val_{17}$-$Ala_{18}$), 58-65 ($Ile_{58}$-$Tyr_{59}$-$Ser_{60}$-$Gln_{61}$-$Val_{62}$-$Leu_{63}$-$Phe_{64}$-$Lys_{65}$), 115-125 ($Tyr_{115}$-$Glu_{116}$-$Pro_{117}$-$Ile_{118}$-$Tyr_{119}$-$Leu_{120}$-$Gly_{121}$-$Gly_{122}$-$Val_{123}$-$Phe_{124}$-$Gln_{125}$) and 138-149 ($Arg_{138}$-$Pro_{139}$-$Asp_{140}$-$Tyr_{141}$-$Leu_{142}$-$Asp_{143}$-$Phe_{144}$-$Ala_{145}$-$Glu_{146}$-$Ser_{147}$-$Gly_{148}$-$Gln_{149}$), or the topographic region of residues 1-18 ($Val_1$-$Arg_2$-$Ser_3$-$Ser_4$-$Ser_5$-$Arg_6$-$Thr_7$-$Pro_8$-$Ser_9$-$Asp_{10}$-$Lys_{11}$-$Pro_{12}$-$Val_{13}$-$Ala_{14}$-$His_{15}$-$Val_{16}$-$Val_{17}$-$Ala_{18}$), 108-128 ($Gly_{108}$-$Ala_{109}$-$Glu_{110}$-$Ala_{111}$-$Lys_{112}$-$Pro_{113}$-$Trp_{114}$-$Tyr_{115}$-$Glu_{116}$-$Pro_{117}$-$Ile_{118}$-$Tyr_{119}$-$Leu_{120}$-$Gly_{121}$-$Gly_{122}$-$Val_{123}$-$Phe_{124}$-$Gln_{125}$-$Leu_{126}$-$Glu_{127}$-$Lys_{128}$), or the topographic region of residues 56-79 ($Tyr_{56}$-$Leu_{57}$-$Ile_{58}$-$Tyr_{59}$-$Ser_{60}$-$Gln_{61}$-$Val_{62}$-$Leu_{63}$-$Phe_{64}$-$Lys_{65}$-$Gly_{66}$-$Gln_{67}$-$Gly_{68}$-$Cys_{69}$-$Pro_{70}$-$Ser_{71}$-$Thr_{72}$-$His_{73}$-$Val_{74}$-$Leu_{75}$-$Leu_{76}$-$Thr_{77}$-$His_{78}$-$Thr_{79}$), 110-127 ($Glu_{110}$-$Ala_{111}$-$Lys_{112}$-$Pro_{113}$-$Trp_{114}$-$Tyr_{115}$-$Glu_{116}$-$Pro_{117}$-$Ile_{118}$-$Tyr_{119}$-$Leu_{120}$-$Gly_{122}$-$Gly_{122}$-$Val_{123}$-$Phe_{124}$-$Gln_{125}$-$Leu_{126}$-$Glu_{127}$) and 135-155 ($Glu_{135}$-$Ile_{136}$-$Asn_{137}$-$Arg_{138}$-$Pro_{139}$-$Asp_{140}$-$Tyr_{141}$-$Leu_{142}$-$Asp_{143}$-$Phe_{144}$-$Ala_{145}$-$Glu_{146}$-$Ser_{147}$-$Gly_{148}$-$Gln_{149}$-$Val_{150}$-$Tyr_{151}$-$Phe_{152}$-$Gly_{153}$-$Ile_{154}$-$Ile_{155}$) is substantially prevented from binding to naturally occurring biologically active ligands.

In a third aspect the present invention consists in a ligand which binds to human TNF in at least two regions selected from the group consisting predominantly of the topographic region of residues 1-20 ($Val_1$-$Arg_2$-$Ser_3$-$Ser_4$-$Ser_5$-$Arg_6$-$Thr_7$-$Pro_8$-$Ser_9$-$Asp_{10}$-$Lys_{11}$-$Pro_{12}$-$Val_{13}$-$Ala_{14}$-$His_{15}$-$Val_{16}$-$Val_{17}$-$Ala_{18}$-$Asn_{19}$-$Pro_{20}$), the topographic region of residues 56-77 ($Tyr_{56}$-$Leu_{57}$-$Iles_{58}$-$Tyr_{59}$-$Ser_{60}$-$Gln_{61}$-$Val_{62}$-$Leu_{63}$-$Phe_{64}$-$Lys_{65}$-$Gly_{66}$-$Gln_{67}$-$Gly_{68}$-$Cys_{69}$-$Pro_{70}$-$Ser_{71}$-$Thr_{72}$-$His_{73}$-$Val_{74}$-$Leu_{75}$-$Leu_{76}$-$Thr_{77}$), the topographic region of residues 108-127 ($Gly_{108}$-$Ala_{109}$-$Glu_{110}$-$Ala_{111}$-$Lys_{112}$-$Pro_{113}$-$Trp_{114}$-$Tyr_{115}$-$Glu_{116}$-$Pro_{117}$-$Ile_{118}$-$Tyr_{119}$-$Leu_{120}$-$Gly_{121}$-$Gly_{122}$-$Val_{123}$-$Phe_{124}$-$Gln_{125}$-$Leu_{126}$-$Glu_{127}$) and the topographic region of residues 138-149 ($Arg_{138}$-$Pro_{139}$-$Asp_{140}$-$Tyr_{141}$-$Leu_{142}$-$Asp_{143}$-$Phe_{144}$-$Ala_{145}$-$Glu_{146}$-$Ser_{147}$-$Gly_{148}$-$Gln_{149}$).

In a preferred embodiment of the third aspect of the present invention the ligand binds to human TNF in the topographic regions of residues 1-18, 58-65, 115-125 and 136-149. Such sequence regions are topographically represented in FIG. 23.

In a further preferred embodiment of the third aspect of the present invention the ligand binds to human TNF in the topographic regions of residues 1-18 ($Val_1$-$Arg_2$-$Ser_3$-$Ser_4$-$Ser_5$-$Arg_6$-$Thr_7$-$Pro_8$-$Ser_9$-$Asp_{10}$-$Lys_{11}$-$Pro_{12}$-$Val_{13}$-$Ala_{14}$-$His_{15}$-$Val_{16}$-$Val_{17}$-$Ala_{18}$) and 108-128 ($Gly_{108}$-$Ala_{109}$-$Glu_{110}$-$Ala_{111}$-$Lys_{112}$-$Pro_{113}$-$Trp_{114}$-$Tyr_{115}$-$Glu_{116}$-$Pro_{117}$-$Ile_{118}$-$Tyr_{119}$-$Leu_{120}$-$Gly_{121}$-$Gly_{122}$-$Val_{123}$-$Phe_{124}$-$Gln_{125}$-$Leu_{126}$-$Glu_{127}$-$Lys_{128}$). Such sequence regions are topographically represented in FIG. 24.

In a further preferred embodiment of the second aspect of the present invention the ligand binds to human TNF in the topographic regions of residues 56-79, 110-127 and 136-155. Such sequence regions are topographically represented in FIG. 25.

In a particularly preferred embodiment of the first, second and third aspects of the present invention the ligand is a monoclonal antibody selected from the group consisting of the monoclonal antibodies designated MAb 1, MAb 47 and MAb 54. Samples of the hybridoma cell lines which produce MAb 1, MAb 54 and MAb 47 have been deposited with the European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom. MAb 1 was deposited on 3 Aug. 1989 and accorded Accession No. 89080301; MAb 54 was deposited on 31 Aug. 1989 and accorded Accession No. 89083103; MAb 47 was deposited on 14 Dec. 1989 and accorded Accession No. 89121402, under the terms and conditions of the Budapest Treaty for the Deposit of Microorganisms for Patent purposes.

In a fourth aspect the present invention consists in a composition comprising TNF in combination with the ligand of the first, second or third aspect of the present invention, characterised in that the ligand is bound to the TNF.

In a fifth aspect the present invention consists in a method of treating toxic shock comprising administering either the ligand of the first, second or third aspect of the present invention or the composition of the fourth aspect of the present invention.

In a sixth aspect the present invention consists in a ligand capable of binding to human TNF, the ligand being characterised in that when it binds to TNF the induction of endothelial procoaglulant activity of the TNF is inhibited; binding of TNF to receptors on endothelial cells is inhibited; the induction of tumour fibrin deposition and tumour regression activities of the TNF are enhanced; the cytotoxicity is unaffected and tumour receptor binding activities of the TNF are unaffected or enhanced.

In a seventh aspect the present invention consists in a ligand capable of binding to human TNF, the ligand being characterized in that when it binds to TNF the induction of endothelial procoagulant activity of the TNF is inhibited; the binding of the TNF to receptors on endothelial cells is inhibited, the induction of tumour fibrin deposition and tumour regression activities of the TNF are enhanced; and the cytotoxicity and receptor binding activities of the TNF are unaffected; the ligand binding to the TNF such that the epitope of the TNF defined by the topographic regions of residues 1-30, 117-128 and 141-153 is substantially prevented from binding to naturally occurring biologically active ligands.

In an eighth aspect the present invention consists of a ligand which binds to human TNF in the topographic regions of residues 1-30, 117-128 and 141-153.

In a preferred embodiment of the eighth aspect of the present invention the ligand binds to human TNF in the topographic regions of residues 1-26, 117-128 and 141-153. Such sequence regions are topographically represented in to FIG. 26.

In a preferred embodiment of the sixth, seventh and eighth aspects of the present invention the ligand is the monoclonal antibody designated MAb 32. A sample of the hybridoma. producing MAb 32 was deposited with The European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom on 3 Aug. 1989 and was accorded Accession No. 89080302, under the terms and conditions of the Budapest Treaty for the Deposit of Microorganisms for Patent purposes.

In a ninth aspect the present invention consists in a composition comprising TNF in combination with a ligand of the sixth, seventh or eighth aspects of the present invention characterised in that the ligand is bound to TNF. No previous documentation of administering MAbs with TNF in order to modify activity of the administered cytokine exists.

In a tenth aspect the present invention consists in a method of treating tumours the growth of which is inhibited by TNF, comprising administering either the ligand of the sixth, seventh or eighth aspects of the present invention or the composition of the ninth aspect of the present invention.

In an eleventh aspect the present invention consists in a ligand which binds to residues 1-18 of human TNF (peptide 301).

In a twelfth aspect the present invention consists in a ligand capable of binding to human TNF, the ligand being characterized in that when it binds to TNF the induction of endothelial procoagulant activity of the TNF is inhibited; the binding of TNF to receptors on endothelial cells is inhibited; the induction of tumour fibrin deposition and tumour regression activities of the TNF are enhanced; the cytotoxicity of the TNF are unaffected and tumour receptor binding activities of the to TNF are unaffected or enhanced, the ligand binding to TNF such that the epitope of the TNF defined by the topographic region of residues 1-18 is substantially prevented from binding to naturally occurring biologically active ligands.

In a thirteenth aspect the present invention consists in a composition comprising TNF in combination with a ligand of the eleventh or twelfth aspects of the present invention characterized in that the ligand is bound to the TNF.

In a fourteenth aspect the present invention consists in a method of treating tumours the growth of which is inhibited by TNF, comprising administering either the ligand of the eleventh or twelfth aspect of the present invention or the composition of the thirteenth aspect of the prevent invention.

In a fifteenth aspect the present invention consists in a ligand capable of binding to human TNF, the ligand being characterised in that when it binds to TNF the cytotoxicity and tumour regression activities of the TNF are unaffected, the induction of endothelial procoagulant and induction of tumour fibrin deposition activities of the TNF are inhibited and receptor binding activities of the TNF are unaffected.

In a sixteenth aspect the present invention consists in a ligand capable of binding to human TNF, the ligand being characterized in that when it binds to TNF the cytotoxicity and tumour regression activities of the TNF are unaffected; the induction of endothelial procoagulant and induction of tumour fibrin deposition activities of the TNF are inhibited and the tumour receptor binding activities of the TNF are unaffected, the ligand binding to TNF such that the epitope of the TNF defined by the topographic regions of residues 22-40 ($Ala_{22}$-$Glu_{23}$-$Gly_{24}$-$Gln_{25}$-$Leu_{26}$-$Gln_{27}$-$Trp_{28}$-$Leu_{29}$-$Asn_{30}$-$Arg_{31}$-$Arg_{32}$-$Ala_{33}$-$Asn_{34}$-$Ala_{35}$-$Leu_{36}$-$Leu_{37}$-$Ala_{38}$-$Asn_{39}$-$Gly_{40}$), 49-96 ($Val_{49}$-$Val_{50}$-$Pro_{51}$-$Ser_{52}$-$Glu_{53}$-$Gly_{54}$-$Leu_{55}$-$Tyr_{56}$-$Leu_{57}$-$Ile_{58}$-$Tyr_{59}$-$Ser_{60}$-$Gln_{61}$-$Val_{62}$-$Leu_{63}$-$Phe_{64}$-$Lys_{65}$-$Gly_{66}$-$Gln_{67}$-$Gly_{68}$-$Cys_{69}$-$Pro_{70}$-$Ser_{71}$-$Thr_{72}$-$His_{73}$-$Val_{74}$-$Leu_{75}$-$Leu_{76}$-$Thr_{77}$-$His_{78}$-$Thr_{79}$-$Ile_{80}$-$Ser_{81}$-$Arg_{82}$-$Ile_{83}$-$Ala_{84}$-$Val_{85}$-$Ser_{86}$-$Tyr_{87}$-$Gln_{88}$-$Thr_{89}$-$Lys_{90}$-$Val_{91}$-$Asn_{92}$-$Leu_{93}$-$Leu_{94}$-$Ser_{95}$-$Ala_{96}$), 110-127 ($Glu_{110}$-$Ala_{111}$-$Lys_{112}$-$Pro_{113}$-$Trp_{114}$-$Tyr_{115}$-$Glu_{116}$-$Pro_{117}$-$Ile_{118}$-$Tyr_{119}$-$Leu_{120}$-$Gly_{121}$-$Gly_{122}$-$Val_{123}$-$Phe_{124}$-$Gln_{125}$-$Leu_{126}$-$Glu_{127}$), and 136-153 ($Ile_{136}$-$Asn_{137}$-$Arg_{138}$-$Pro_{139}$-$Asp_{140}$-$Tyr_{141}$-$Leu_{142}$-$Asp_{143}$-$Phe_{144}$-$Ala_{145}$-$Glu_{146}$-$Ser_{147}$-$Gly_{148}$-$Gln_{149}$-$Val_{150}$-$Tyr_{151}$-$Phe_{152}$-$Gly_{153}$) is substantially prevented from binding to naturally occurring biologically active ligands.

In a seventeenth aspect the present invention consists in a ligand which binds to human TNF in the topographic regions of residues 22-40 ($Ala_{22}$-$Glu_{23}$-$Gly_{24}$-$Leu_{26}$-$Gln_{27}$-$Trp_{28}$-$Leu_{29}$-$Asn_{30}$-$Arg_{31}$-$Arg_{32}$-$Ala_{33}$-$Asn_{34}$-$Ala_{35}$-$Leu_{36}$-$Leu_{37}$-$Ala_{38}$-$Asn_{39}$-$Gly_{40}$), 49-97 ($Val_{49}$-$Val_{50}$-$Pro_{51}$-$Ser_{52}$-$Glu_{53}$-$Gly_{54}$-$Leu_{55}$-$Tyr_{56}$-$Leu_{57}$-$Ile_{58}$-$Tyr_{59}$-$Ser_{60}$-$Gln_{61}$-$Val_{62}$-$Leu_{63}$-$Phe_{64}$-$Lys_{65}$-$Gly_{66}$-$Gln_{67}$-$Gly_{68}$-$Cys_{69}$-$Pro_{70}$-$Ser_{71}$-$Thr_{72}$-$His_{73}$-$Val_{74}$-$Leu_{75}$-$Leu_{76}$-$Thr_{77}$-$His_{78}$-$Thr_{79}$-$Ile_{80}$-$Ser_{81}$-$Arg_{82}$-$Ile_{83}$-$Ala_{84}$-$Val_{85}$-$Ser_{86}$-$Tyr_{87}$-$Gln_{88}$-$Thr_{89}$-$Lys_{90}$-$Val_{91}$-$Asn_{92}$-$Leu_{93}$-$Leu_{94}$-$Ser_{95}$-$Ala_{96}$-$Ile_{97}$), 110-127 ($Glu_{110}$-$Ala_{111}$-$Lys_{112}$-$Pro_{113}$-$Trp_{114}$-$Tyr_{115}$-$Glu_{116}$-$Pro_{117}$-$Ile_{118}$-$Tyr_{119}$-$Leu_{120}$-$Gly_{121}$-$Gly_{122}$-$Val_{123}$-$Phe_{124}$-$Gln_{125}$-$Leu_{126}$-$Glu_{127}$), and 136-153 ($Ile_{136}$-$Asn_{137}$-$Arg_{138}$-$Pro_{139}$-$Asp_{140}$-$Tyr_{141}$-$Leu_{142}$-$Asp_{143}$-$Phe_{144}$-$Ala_{145}$-$Glu_{146}$-$Ser_{147}$-$Gly_{148}$-$Gln_{149}$-$Val_{150}$-$Tyr_{151}$-$Phe_{152}$-$Gly_{153}$). Such sequence regions are topographically represented in FIG. 27.

In a preferred embodiment of the seventeenth aspect of the present invention the ligand binds to human TNF in the topographic regions of residues 22-40 ($Ala_{22}$-$Glu_{23}$-$Gly_{24}$-$Gln_{25}$-$Leu_{26}$-$Gln_{27}$-$Trp_{28}$-$Leu_{29}$-$Asn_{30}$-$Arg_{31}$-$Arg_{32}$-$Ala_{33}$-$Asn_{34}$-$Ala_{35}$-$Leu_{36}$-$Leu_{37}$-$Ala_{38}$-$Asn_{39}$-$Gly_{40}$), 49-96 ($Val_{49}$-$Val_{50}$-$Pro_{51}$-$Ser_{52}$-$Glu_{53}$-$Gly_{54}$-$Leu_{55}$-$Tyr_{56}$-$Leu_{57}$-$Ile_{58}$-$Tyr_{59}$-$Ser_{60}$-$Gln_{61}$-$Val_{62}$-$Leu_{63}$-$Phe_{64}$-$Lys_{65}$-$Gly_{66}$-$Gln_{67}$-$Gly_{68}$-$Cys_{69}$-$Pro_{70}$-$Ser_{71}$-$Thr_{72}$-$His_{73}$-$Val_{74}$-$Leu_{75}$-$Leu_{76}$-$Thr_{77}$-$His_{78}$-$Thr_{79}$-$Ile_{80}$-$Ser_{81}$-$Arg_{82}$-$Ile_{83}$-$Ala_{84}$-$Val_{85}$-$Ser_{86}$-$Tyr_{87}$-$Gln_{88}$-$Thr_{89}$-$Lys_{90}$-$Val_{91}$-$Asn_{92}$-$Leu_{93}$-$Leu_{94}$-$Ser_{95}$-$Ala_{96}$), 110-127 ($Glu_{110}$-$Ala_{111}$-$Lys_{112}$-$Pro_{113}$-$Trp_{114}$-$Tyr_{115}$-$Glu_{116}$-$Pro_{117}$-$Tyr_{119}$-$Leu_{120}$-$Gly_{121}$-$Gly_{122}$-$Val_{123}$-$Phe_{124}$-$Gln_{125}$-$Leu_{126}$-$Glu_{127}$), and 136-153 ($Ile_{136}$-$Asn_{137}$-$Arg_{138}$-$Pro_{139}$-$Asp_{140}$-$Tyr_{141}$-$Leu_{142}$-$Asp_{143}$-$Phe_{144}$-$Ala_{145}$-$Glu_{146}$-$Ser_{147}$-$Gly_{148}$-$Gln_{149}$-$Val_{150}$-$Tyr_{151}$-$Phe_{152}$-$Gly_{153}$). These regions being proximate in the 3D structure of TNF alpha.

In a preferred embodiment of the fifteenth, sixteenth and seventeenth aspects of the present invention the ligand is the monoclonal antibody designated MAb 42. A sample of the hybridoma. cell line producing MAb 42 was deposited with The European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom on 3 Aug. 1989 and was accorded Accession No. 89080304, under the terms and conditions of the Budapest Treaty for the Deposit of Microorganisms for Patent purposes.

In an eighteenth aspect the present invention consists in a composition comprising TNF in combination with the ligand of the fifteenth, sixteenth or seventeenth aspects of the present invention, characterised in that the ligand is bound to the TNF.

In a nineteenth aspect the present invention consists in a method of treating tumours inhibited by the action of TNF comprising administering the ligand of the fifteenth, sixteenth or seventeenth aspects of the present invention or the composition of the eighteenth aspect of the present invention.

In a twentieth aspect the present invention consists in a ligand capable of binding to human TNF, the ligand being characterised in that when it binds to TNF the tumour fibrin deposition activity of the TNF is enhanced; the induction of endothelial procoagulant activity of the TNF is unaffected and the cytotoxicity, tumour regression and receptor binding activities of the TNF are inhibited.

In a twenty-first aspect the present invention consists in a ligand capable of binding to human TNF, the ligand being characterized in that when it binds to TNF the tumour fibrin deposition activity of the TNF is enhanced; the induction of endothelial procoagulant activity of the TNF is unaffected and the cytotoxicity, tumour regression and tumour receptor binding activities of the TNF are inhibited, the ligand binding to TNF such that the epitope of the TNF defined by the topographic regions of residues 12-22 ($Pro_{12}$-$Val_{13}$-$Ala_{41}$-$His_{15}$-$Val_{16}$-$Val_{17}$-$Ala_{18}$-$Asn_{19}$-$Pro_{20}$-$Gln_{21}$-$Ala_{22}$), 36-45 ($Leu_{36}$-$Leu_{37}$-$Ala_{38}$-$Asn_{39}$-$Gly_{40}$-$Val_{41}$-$Glu_{42}$-$Leu_{43}$-$Arg_{44}$-$Asp_{45}$), 96-105 ($Ala_{96}$-$Ile_{97}$-$Lys_{98}$-$Ser_{99}$-$Pro_{100}$-$Cys_{101}$-$Gln_{102}$-$Arg_{103}$-$Glu_{104}$-$Thr_{105}$) and 132-157 ($Leu_{132}$-$Ser_{133}$-$Ala_{134}$-$Glu_{135}$-$Ile_{136}$-$Asn_{137}$-$Arg_{138}$-$Pro_{139}$-$Asp_{140}$-$Tyr_{141}$-$Leu_{142}$-$Asp_{143}$-$Phe_{144}$-$Ala_{145}$-$Glu_{146}$-$Ser_{147}$-$Gly_{148}$-$Gln_{149}$-$Val_{150}$-$Tyr_{151}$-$Phe_{152}$-$Gly_{153}$-$Ile_{154}$-$Ile_{155}$-$Ala_{156}$-$Leu_{157}$) is substantially prevented from binding to naturally occurring biologically active ligands.

In a twenty-second aspect the present invention consists in a ligand which binds to human TNF in the topographic regions of residues 12-22 ($Pro_{12}$-$Val_{13}$-$Ala_{14}$-$His_{15}$-$Val_{16}$-$Val_{17}$-$Ala_{18}$-$Asn_{19}$-$Pro_{20}$-$Gln_{21}$-$Ala_{22}$), 36-45 ($Leu_{36}$-$Leu_{37}$-$Ala_{38}$-$Asn_{39}$-$Gly_{40}$-$Val_{41}$-$Glu_{42}$-$Leu_{43}$-$Arg_{44}$-$Asp_{45}$) 96-105 ($Ala_{96}$-$Ile_{97}$-$Lys_{98}$-$Ser_{99}$-$Pro_{100}$-$Cys_{101}$-$Gln_{102}$-$Arg_{103}$-$Glu_{104}$-$Thr_{105}$) and 132-157 ($Leu_{132}$-$Ser_{133}$-$Ala_{134}$-$Glu_{135}$-$Ile_{136}$-$Asn_{137}$-$Arg_{138}$-$Pro_{139}$-$Asp_{140}$-$Tyr_{141}$-$Leu_{142}$-$Asp_{143}$-$Phe_{144}$-$Ala_{145}$-$Glu_{146}$-$Ser_{147}$-$Gly_{148}$-$Gln_{149}$-$Val_{150}$-$Tyr_{151}$-$Phe_{152}$-$Gly_{153}$-$Ile_{154}$-$Ile_{155}$-$Ala_{156}$-$Leu_{157}$). These regions are proximate in the 3D structure of TND and are topographically represented in FIG. 28.

In a preferred embodiment of the twentieth, twenty-first and twenty-second aspects of the present invention the ligand is the monoclonal antibody designated MAb 25. A sample of the hybridoma cell line producing MAb 25 was deposited with the European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom on 14 Dec. 1989 and was accorded Accession No. 89121401, under the terms and conditions of the Budapest Treaty for the Deposit of Microoruanisms for Patent purposes.

In a twenty-third aspect the present invention consists in a ligand capable of binding to human TNF, the ligand being characterised in that when it binds to TNF the tumour fibrin deposition activity of the TNF is enhanced and the cytotoxicity, tumour regression, induction of endothelial procoagulant and receptor binding activities of the TNF are inhibited.

In a twenty-fourth aspect the present invention consists in a ligand capable of binding to human TNF, the ligand being characterized in that when it binds to TNF the tumour fibrin deposition activity of the TNF is enhanced and the cytotoxicity, tumour regression, induction of endothelial procoagulant and tumour receptor binding activities of the TNF are inhibited, the ligand binding to the TNF such that the epitope of the TNF defined by the topographic regions of residues 1-20 ($Val_1$-$Arg_2$-$Ser_3$-$Ser_4$-$Ser_5$-$Arg_6$-$Thr_7$-$Pro_8$-$Ser_9$-$Asp_{10}$-$Lys_{11}$-$Pro_{12}$-$Val_{13}$-$Ala_{14}$-$His_{15}$-$Val_{16}$-$Val_{17}$-$Ala_{18}$-$Asn_{19}$-$Pro_{20}$) and 76-90 ($Leu_{76}$-$Thr_{77}$-$His_{78}$-$Thr_{79}$-$Ile_{80}$-$Ser_{81}$-$Arg_{82}$-$Ile_{83}$-$Ala_{84}$-$Val_{85}$-$Ser_{86}$-$Tyr_{87}$-$Gln_{88}$-$Thr_{89}$-$Lys_{90}$) is substantially prevented from binding to naturally occurring biologically active ligands.

In a twenty-fifth aspect the present invention consists in a ligand which binds to human TNF in the topographic regions of residues 1-20 and 76-90. These regions proximate in the 3D structure of TNF and are topographically represented in FIG. 29.

In a preferred embodiment of the twenty-fifth aspect of the present invention the ligand binds to TNF in the topographic regions of residues 1-18 ($Val_1$-$Arg_2$-$Ser_3$-$Ser_4$-$Ser_5$-$Arg_6$-$Thr_7$-$Pro_8$-$Ser_9$-$Asp_{10}$-$Lys_{11}$-$Pro_{12}$-$Val_{13}$-$Ala_{14}$-$His_{15}$-$Val_{16}$-$Val_{17}$-$Ala_{18}$) and 76-90 ($Leu_{76}$-$Thr_{77}$-$His_{78}$-$Thr_{79}$-$Ile_{80}$-$Ser_{81}$-$Arg_{82}$-$Ile_{83}$-$Ala_{84}$-$Val_{85}$-$Ser_{86}$-$Tyr_{87}$-$Gln_{88}$-$Thr_{89}$-$Lys_{90}$).

In a preferred embodiment of the twenty-third, twenty-fourth and twenty-fifth aspects of the present invention the ligand is the monoclonal antibody designated MAb 21. A sample of the hybridoma cell line producing MAb 21 was deposited with the European Collection of Animal Cell Cultures (ECACC), Vaccine Research and Production Laboratory, Public Health Laboratory Service Centre for Applied Microbiology and Research, Porton Down, Salisbury, Wiltshire SP4 OJG, United Kingdom on 25 Jan. 1990 and was accorded Accession No. 90012432, under the terms and conditions of the Budapest Treaty for the Deposit of Microorganisms for Patent purposes.

In a twenty-sixth aspect the present invention consists in a ligand capable of binding to human TNF, the ligand being characterised in that when it binds to TNF the fibrin deposition activity of the TNF is unaffected and the cytotoxicity, tumour regression, induction of endothelial procoagulant and tumour receptor binding activities of the TNF are inhibited.

In a twenty-seventh aspect the present invention consists in a ligand capable of binding to human TNF, the ligand being characterized in that when it binds to TNF the tumour fibring deposition activity of the TNF is unaffected and the cytotoxicity, tumour regression, induction of endothelial procoagulant and receptor binding activities of the TNF are inhibited, the ligand bindng to the TNF such that the epitope of the TNF defined by the topographic regions of residues 22-40 ($Ala_{22}$-$Glu_{23}$-$Gly_{24}$-$Gln_{25}$-$Leu_{26}$-$Gln_{27}$-$Trp_{28}$-$Leu_{29}$-$Asn_{30}$-$Arg_{31}$-$Arg_{32}$-$Ala_{33}$-$Asn_{34}$-$Ala_{35}$-$Leu_{36}$-$Leu_{37}$-$Ala_{38}$-$Asn_{39}$-$Gly_{40}$), 69-97 ($Cyc_{69}$-$Pro_{70}$-$Ser_{71}$-$Thr_{72}$-$His_{73}$-$Val_{74}$-$Leu_{75}$-$Leu_{76}$-$Thr_{77}$-$His_{78}$-$Thr_{79}$-$Ile_{80}$-$Ser_{81}$-$Arg_{82}$-$Ile_{83}$-$Ala$-$_{84}$-$Val_{85}$-$Ser_{86}$-$Tyr_{87}$-$Gln_{88}$-$Thr_{89}$-$Lys_{90}$-$Val_{91}$-$Asn_{92}$-$Leu_{93}$-$Leu_{94}$-$Ser_{95}$-$Ala_{96}$-$Ile_{97}$), 105-128 ($Thr_{105}$-$Pro_{106}$-$Glu_{107}$-$Gly_{108}$-$Ala_{109}$-$Glu_{110}$-$Ala_{111}$-$Lys_{112}$-$Pro_{113}$-$Trp_{114}$-$Tyr_{115}$-$Glu_{116}$-$Pro_{117}$-$Ile_{118}$-$Tyr_{119}$-$Leu_{120}$-$Gly_{121}$-$Gly_{122}$-$Val_{123}$-$Phe_{124}$-$Gln_{125}$-$Leu_{126}$-$Glu_{127}$-$Lys_{128}$) and 135-155 ($Glu_{135}$-$Ile_{136}$-$Asn_{137}$-$Arg_{138}$-$Pro_{139}$-$Asp_{140}$-$Tyr_{141}$-$Leu_{142}$-$Asp_{143}$-$Phe_{144}$-$Ala_{145}$-$Glu_{146}$-$Ser_{147}$-$Gly_{148}$-$Gln_{149}$-$Val_{150}$-$Tyr_{151}$-$Phe_{152}$-$Gly_{153}$-$Ile_{154}$-$Ile_{155}$) is substantially prevented from binding to naturally occurring biologically active ligands.

In a twenty-eighth aspect the present invention consists in a ligand which binds to human TNF in the topographic regions of residues 22-40, 69-97, 105-128 and 135-155. These regions are proximate in the 3D structure of TNF and are topographically represented in FIG. 30.

In a preferred embodiment of the twenty-sixth, twenty-seventh and twenty-eighth aspects of the present invention the ligand is the monoclonal antibody designated MAb 53. A sample of the hybridoma cell line producing MAb 53 was deposited with the European Collection of Animal Cell cultures (ECACC), Vaccine Research and Production Laboratory, Public Health Laboratory Service, Centre for Applied Microbiology and Research, Porton Down, Salisbury, Wiltshire SP4 OJG, United Kingdom on 25 Jan. 1990 and was accorded Accession No. 90012433, under the terms and conditions of the Budapest Treaty for the Deposit of Microorganisms for Patent purposes.

In a twenty-ninth aspect the present invention consists in a ligand capable of binding to human TNF, the ligand being characterised in that when it binds to the TNF tumour fibrin deposition, induction of endothelial procoagulant, cytotoxicity, tumour regression and receptor binding activities of the TNF are unaffected.

In a thirtieth aspect the present invention consists in a ligand capable of binding to human TNF, the ligand being characterised in that when it binds to TNF the tumour fibrin deposition, induction of endothelial procoagulant, cytotoxicity, tumour regression and receptor binding activities of the TNF are uneffected, the ligand binding to TNF such that the epitope of the TNF defined by the topographic regions of residues 22-31 and 146-157 is substantially prevented from binding to naturally occurring biologically active ligands.

In a thirty-first aspect the present invention consists in a ligand which binds to human TNF in the topographic regions of residues 22-31 and 146-157. These regions are proximate in the 3D structure of TNF and are typographically represented in FIG. 31.

In a preferred embodiment of the twenty-ninth, thirtieth and thirty-first-aspects of the present invention the ligand is the monoclonal antibody designated MAb 37. A sample of the hybridoma cell line producing MAb 37 was deposited with the European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom on 3 Aug. 1989 and was accorded Accession No. 89080303, under the terms and conditions of the Budapest Treaty for the Deposit of Microorganisms for Patent purposes.

In a thirty-second aspect the present invention consists in a ligand capable of binding to human TNF, the ligand being characterised in that when it binds to TNF the induction of endothelial procoagulant activity of the TNF is unaffected and the cytotoxicity tumour regression, tumour fibrin deposition, and receptor binding activities of the TNF are inhibited.

In a thirty-third aspect the present invention consists in a ligand capable of binding to human TNF, the ligand being characterised in that when it binds to TNF the induction of endothelial procoagulant activity of the TNF is unaffected and the cytotoxicity, tumour regressions tumour fibrin deposition and receptor binding activities of the TNF are inhibited, the ligand binding to the TNF such that the epitope of the TNF defined by the topographic regions of residues 22-40 and 49-98 is substantially prevented from binding to naturally occurring biologically active ligands.

In a thirty-fourth aspect the present invention consists in a ligand which binds to human TNF in at least one of the regions selected from the group consisting of the topographic region of residues 22-40, the topographic region of residues 49-98 and the topographic region of residues 69-97.

In a preferred embodiment of the thirty-fourth aspect of the present invention the ligand binds to human TNF in the topographical region of residues 49-98. This region is topographically represented in FIG. 32.

In a further preferred embodiment of the thirty-fourth aspect of the present invention the ligand binds to human TNF in the topographic regions of residues 22-40 and 70-87. These regions are proximate in the 3D structure of TNF and are topographically represented in FIG. 33.

In a preferred embodiment of the thirty-second, thirty-third and thirty-fourth aspects of the present invention the ligand is monoclonal antibody MAb 11 or MAb 12.

In a thirty-fifth aspect the present invention consists in a ligand capable of binding to human TNF, the ligand being characterised in that when it binds to TNF the induction of endothelial procoagulant activity of the TNF is inhibited.

In a thirty-sixth aspect the present invention consists in a ligand capable of binding to human TNF, the ligand being characterised in that when it binds to TNF the induction of endothelial procoagulant activity of the TNF is inhibited, the ligand binding to TNF such that the epitope of the TNF defined by the topographical region of residues 108-128 ($Gly_{108}$-$Ala_{109}$-$Glu_{110}$-$Ala_{111}$-$Lys_{112}$-$Pro_{113}$-$Trp_{114}$-$Tyr_{115}$-$Glu_{116}$-$Pro_{117}$-$Ile_{118}$-$Tyr_{119}$-$Leu_{120}$-$Gly_{121}$-$Gly_{122}$-$Val_{123}$-$Phe_{124}$-$Gln_{125}$-$Leu_{126}$-$Glu_{127}$-$Lys_{128}$) is prevented from binding to naturally occurring biologically active ligands.

In a thirty-seventh aspect the present invention consists in a ligand which binds to human TNF in the topographical region of residues 108-128 ($Gly_{108}$-$Ala_{109}$-$Glu_{110}$-$Ala_{111}$-$Lys_{112}$-$Pro_{113}$-$Trp_{114}$-$Tyr_{115}$-$Glu_{116}$-$Pro_{117}$-$Ile_{118}$-$Tyr_{119}$-$Leu_{120}$-$Gly_{121}$-$Gly_{122}$-$Val_{123}$-$Phe_{124}$-$Gln_{125}$-$Leu_{126}$-$Glu_{127}Lys_{128}$).

In a preferred embodiment of the thirty-fifth, thirty-sixth and thirty-seventh aspects of the present invention the ligand is selected from the group consisting of monoclonal antibodies designated MAb 1, MAb 32, MAb 42, MAb 47, MAb 53 and MAb 54.

The biological activities of TNF referred to herein by the terms "Tumour Regression", "Induction of Endothelial Procoagulant", "Induction of Tumour Fibrin Deposition", "Cytotoxicity" and "Receptor Binding" are to be determined by the methods described below.

The term "single domain antibodies" as used herein is used to denote those antibody fragments such as described in Ward et al (Nature, Vol. 341, 1989, 544-546) as suggested by these authors.

In order that the nature of the present invention may be more clearly understood, preferred forms thereof will now be described with reference to the following example and accompanying figures in which:

BRIEF DESCRIPTION OF THE DRAWINGS

FIGS. 21a, 21b and 21c show MAb 32 reactivity with overlapping peptides of 10 AA length.

FIG. 35 shows the effect of VHP3-VλA2 on anti-tumour activity of TNF.

DESCRIPTION OF THE PREFERRED EMBODIMENTS

Animals and Tumour Cell Lines

Figure 1:
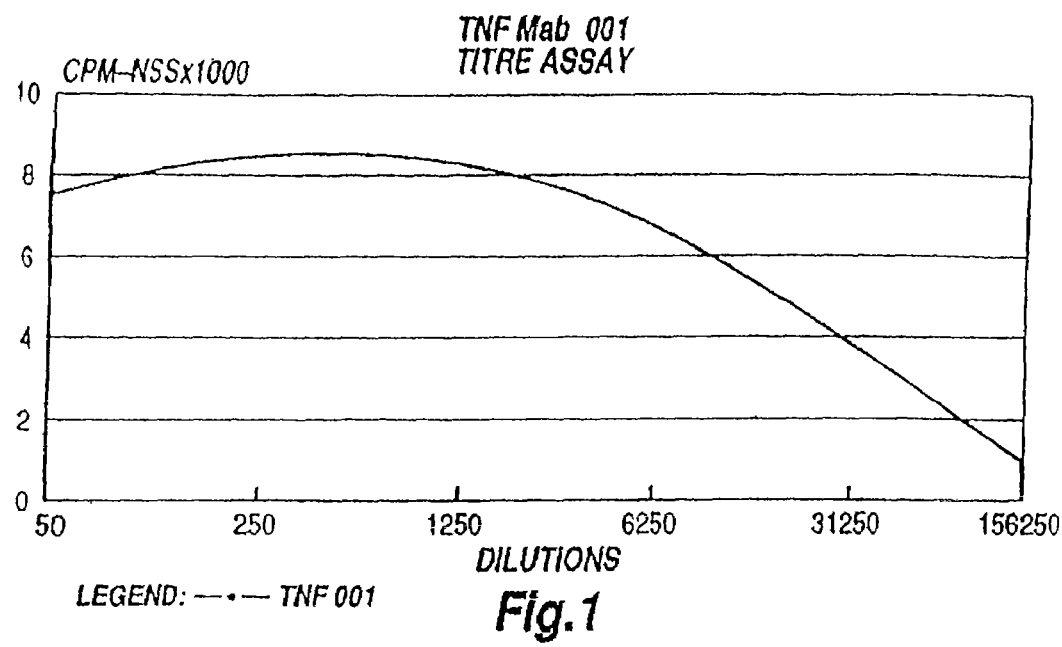
FIG. 1 shows the results of a titration assay with MAb 1 against TNF.

In all experiments BALB/C female mice aged 10-12 weeks obtained from the CSIRO animal facility were used. Meth A solid tumour and Meth A ascites tumour cell lines were obtained from the laboratory of Dr. Lloyd J. Old (Sloan Kettering Cancer Centre) and the WEHI-164 fibrosarcoma line was obtained from Dr. Geeta Chauhdri (John Curtin School of Medical Research, Australian National University).

Fusions and Production of Hybridomas

Mice were immunised with 10 ug human recombinant TNF intra-peritoneally in Freund's complete adjuvant. One month later 10 ug TNF in Freund's incomplete adjuvant was administered. Six weeks later and four days prior to fusion selected mice were boosted with 10 ug TNF in PBS. Spleen cells from immune mice were fused with the myeloma Sp2/0 according to the procedure of Rathjen and Underwood (1986, Mol. Immunol. 23, 441). Cell lines found to secrete anti-TNF antibodies by radioimmunoasaay were subcloned by limiting dilution on a feeder layer of mouse peritoneal macrophages. Antibody subclasses were determined by ELISA (Misotest, Commonwealth Serum Laboratories).

Radioimmunoassay

TNF was iodinated using lactoperoxidase according to standard procedures. Culture supernatants from hybridomas (50 ul) were incubated with 125I TNF (20,000 cpm in 50 ul) overnight at 4° C. before the addition of 100 ul Sac-Cel (donkey anti-mouse/rat immunoglobulins coated cellulose, Wellcome Diagnostics) and incubated for a further 20 minutes at room temperature (20° C.). Following this incubation 1 ml of PBS was added and the tubes centrifuged at 2,500 rpm for 5 minutes. The supernatant was decanted and the pellet counted for bound radioactivity.

Antibody-Antibody Competition Assays

The comparative specificities of the monoclonal antibodies were determined in competition assays using either immobilized antigen (LACT) or antibody (PACT) (Aston and Ivanyi, 1985, Pharmac. Therapeut. 27, 403).

Flexible microtitre trays were coated with monoclonal antibody (sodium sulphate precipitated globulins from mouse ascites fluid, 100 micrograms per ml in sodium bicarbonate buffer, 0.5M, pH 9.6) overnight at 4° C. prior to blocking non-specific binding sites with 1% bovine serum albumin in PBS (BSA/PBS). The binding of 125I TNF to immobilised antibody was determined in the presence of varying concentrations of a second anti-TNF monoclonal antibody. Antibody and TNF were added simultaneously and incubated for 24 hours prior to washing with PBS (4 times) and counting wells for bound radioactivity. 100% binding was determined in the absence of heterologous monoclonal antibody while 100% competition was determined in the presence of excess homologous monoclonal antibody. All dilutions were prepared in BSA/PBS.

LACT

The binding of protein A purified, radiolabelled monoclonal antibodies to TNF coated microtitre wells was determined in the presence of varying concentrations of a second monoclonal antibody. Microtitre plates were coated with TNF (50 micrograms per ml) as described above. Quantities of competing antibodies (50 microliters) were pre-incubated on plates for 4 hour at 4° C. prior to addition of 125I monoclonal antibody (30,000 cpm) for a further 24 hours. Binding of counts to wells was determined after four washes with PBS. 100% binding was determined in the absence of competing antibody while 100% competition was determined in the presence of excess unlabelled monoclonal antibody.

WEHI-164 Cytotoxicity Assay

Bioassay of recombinant TNF activity was performed according to Espevik and Nissen-Meyer (1986, J. Immunol. Methods 95, 99). The effect of the monoclonal antibody on TNF activity was determined by the addition of the monoclonal antibody to cell cultures at ABT90.

Tumour Regression Experiments

Modulation of TNF-induced tumour regression activity by monoclonal antibodies was assessed in three tumour models: the subcutaneous tumours WEHI-164 and Meth A sarcoma and the ascitic Meth A tumour. Subcutaneous tumours were induced by the injection of approximately $5 \times 10^5$ cells. This produced tumours of between 10-15 mm approximately 14 days later. Mice were injected intra-peritoneally with human recombinant TNF (10 micrograms) plus monoclonal antibody (200 microliters ascites globulin) for four consecutive days. Control groups received injections of PBS alone or TNF plus monoclonal antibody against bovine growth hormone. At the commencement of each experiment tumour size was measured with calipers in the case of solid tumours or tumour-bearing animals weighed in the case of ascites mice. These measurements were taken daily throughout the course of the experiment.

Radio-Receptor Assays

WEHI-164 cells grown to confluency were scrape harvested and washed once with 1% BSA in Hank's balanced salt solution (HBSS, Gibco). 100 ul of unlabelled TNF (1-10, 000 ng/tube) or monoclonal antibody (10 fold dilutions commencing 1 in 10 to 1 in 100,000 of ascetic globulin) was added to 50 ul 125I TNF (50,000 cmp). WEHI cells were then added (200 microliters containing $2 \times 10^6$ cells). This mixture was incubated in a shaking water bath at 37° C. for 3 hours. At the completion of this incubation 1 ml of HBSS was added and the cells spun at 16,000 rpm for 30 seconds. The supernatant was discarded and bound 125I TNF in the cell pellet counted. All dilutions were prepared in HBSS containing 1% BSA.

Procoagulant Induction by TNF on Endothelial Cells

Bovine aortic endothelial cells (passage 10) were grown in RPMI-1640 containing 10% foetal calf serum (FCS), penicillin, streptomycin, and 2-mercaptoethanol at 37° C. in 5% $CO_2$. For induction of procoagulant activity by TNF the cells were trypsinised and plated into 24-well Costar trays according to the protocol of Bevilacqua et al., 1986 (PNAS 83, 4533). TNF (0-500 units/culture) and monoclonal antibody (1 in 250 dilution of ascitic globulin) was added after washing of the confluent cell monolayer with HBSS. After 4 hours the cells were scrape harvested, frozen and sonicated. Total cellular procoagulant activity was determined by the recalcification time of normal donor platelet-poor plasma performed at 37° C. 100 microliters of citrated platelet-poor plasma was added to 100 ul of cell lysate and 100 ul of calcium chloride (30 mM) and the time taken for clot formation recorded. In some experiments tumour cell culture supernatant was added to endothelial cells treated with TNF and/or monoclonal antibody (final concentration of 1 in 2).

Incorporation of 125I Fibrinogen into Tumours of Mice Treated with TNF and Monoclonal Antibody In order to examine the effect of TNF and monoclonal antibodies on fibrin formation in vivo, BALB/c mice were injected subcutaneously with WEHI-164 cell ($10^5$ cells/animal). After 7-14 days, when tumours reached a size of approximately 1 cm in diameter, animals were injected intra-peritoneally with TNF (10 ug/animal) and 125I human fibrinogen (7.5 ug/animal, 122 uCi/mg Amersham) either alone or in the presence of monoclonal antibody to human TNF (200 ul/animal ascitic globulin). Monoclonal antibody against bovine growth hormone was used as control monoclonal antibody. Two hours after TNF infusion incorporation of 125I fibrinogen into mouse tissue was determined by removing a piece of tissue, weighing it and counting the sample in a gamma counter.

In all 13 monoclonal antibodies reacting with human TNF were isolated. These monoclonal antibodies were designated MAb 1, MAb 11, MAb 12, MAb 20, MAb 21, MAb 25, MAb 31, MAb 32, MAb 37, MAb 42, MAb 47, MAb 53 and MAb 54. The effect of these monoclonal antibodies on the bioactivity of human TNF is set out in Table 2.

As can be seen from Table 2, whilst some monoclonal antibodies inhibit both anti-tumour activity and activation of coagulation by human TNF (MAb 1, 47 and 54) not all antibodies which inhibit the anti-tumour activity inhibit activation of coagulation either in vitro or in vivo (MAb 11, 12, 25 and 53). Indeed MAb 21 which inhibited tumour regression enhanced the activation of coagulation in vivo.

TABLE 2

EFFECT OF MONOCLONAL ANTIBODIES ON TNF BIOACTIVITY

| TNF BIOACTIVITY | MONOCLONAL ANTIBODY | | | | | | | | | | | | |
|---|---|---|---|---|---|---|---|---|---|---|---|---|---|
| | 1 | 11 | 12 | 20 | 21 | 25 | 31 | 32 | 37 | 42 | 47 | 53 | 54 |
| Cytotoxicity | − | − | − | 0 | − | − | 0 | 0 | 0 | 0 | − | − | − |
| Tumour Regression | − | − | − | 0 | − | − | 0 | + | 0 | 0 | − | − | − |
| Induction of Procoagulant (Endothelial | − | 0 | 0 | − | − | 0 | 0 | − | 0 | − | − | − | − |
| Fibrin Deposition (tumour) | − | − | − | + | + | + | + | + | 0 | − | − | 0 | − |
| Receptor Binding (WEHI - 164) | − | − | − | 0 | − | − | 0 | +/0* | 0 | 0 | − | − | − |

+ Enhancement
0 No effect
− Inhibition
*Depending on MAb concentration in the case of WEHI-164 tumour cells and tumour type (see FIGS. 3, 13-17).

MAbs 1, 47 and 54, which have been shown in competition binding studies to share an epitope on TNF, can be seen to have highly desirable characteristics in treatment of toxic shock and other conditions of bacterial, viral and parasitic infection where TNF levels are high requiring complete neutralisation of TNF. Other monoclonal antibodies such as MAb 32 are more appropriate as agents for coadministration with TNF during cancer therapy since they do not inhibit tumour regression but do inhibit activation of coagulation. This form of therapy is particularly indicated in conjunction with cytotoxic drugs used in cancer therapy which may potentiate activation of coagulation by TNF (e.g. vinblastin, acyclovir, IFN alpha, IL-2, actinomycin D, AZT, radiotherapy, adriamycin, mytomycin C, cytosine arabinoside, dounorubicin, cisplatin, vincristine, 5-flurouracil, bleomycin, (Watanabe N et al 1988 Immunopharmacol. Immunotoxicol. 10 117-127) or in diseases where at certain stages TNF levels are low (e.g. AIDS) and where individuals may have AIDS associated cancer e.g. Kaposi sarcoma, non-Hodgkins lymphoma and squamous cell carcinoma.

Monoclonal antibody MAb 1 has been found to have the following characteristics:

1. Binds human recombinant TNF alpha, but not human lymphotoxin (TNF beta) or human interferon. Similarly MAb 1 does not cross-react with recombinant murine TNF (FIG. 1).

Figure 2:
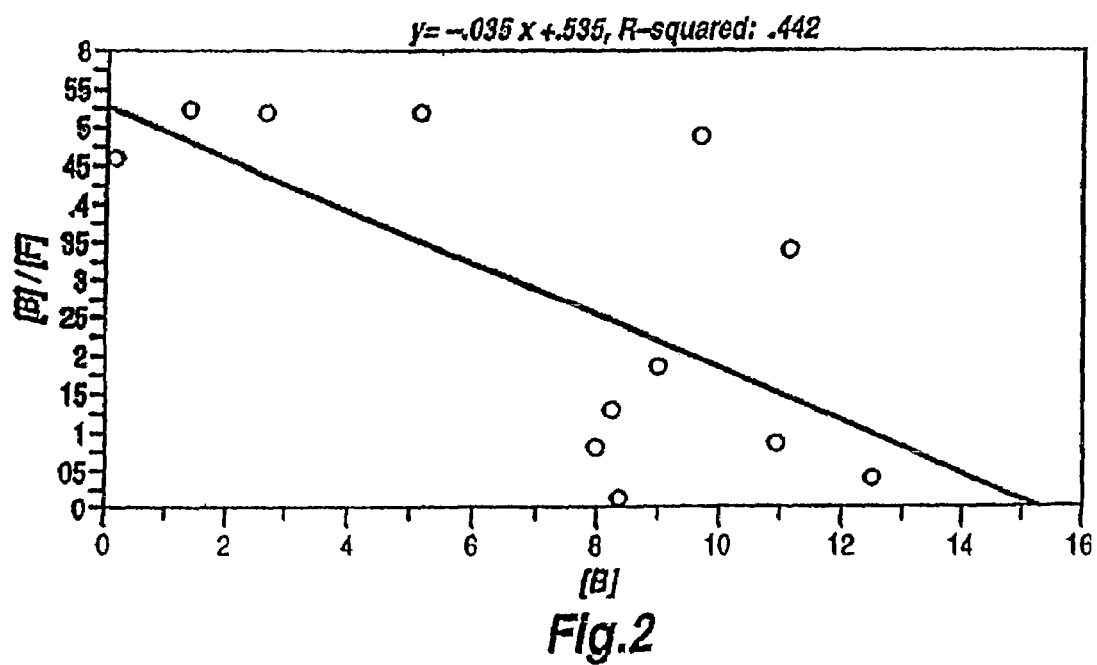
FIG. 2 shows TNF MAb 1 scatchard plot and affinity determination.

2. MAb 1 is of the immunoglobulin type IgG1, K with an apparent affinity of $4.4 \times 10^{-9}$ moles/liter (FIG. 2).

Figure 3:
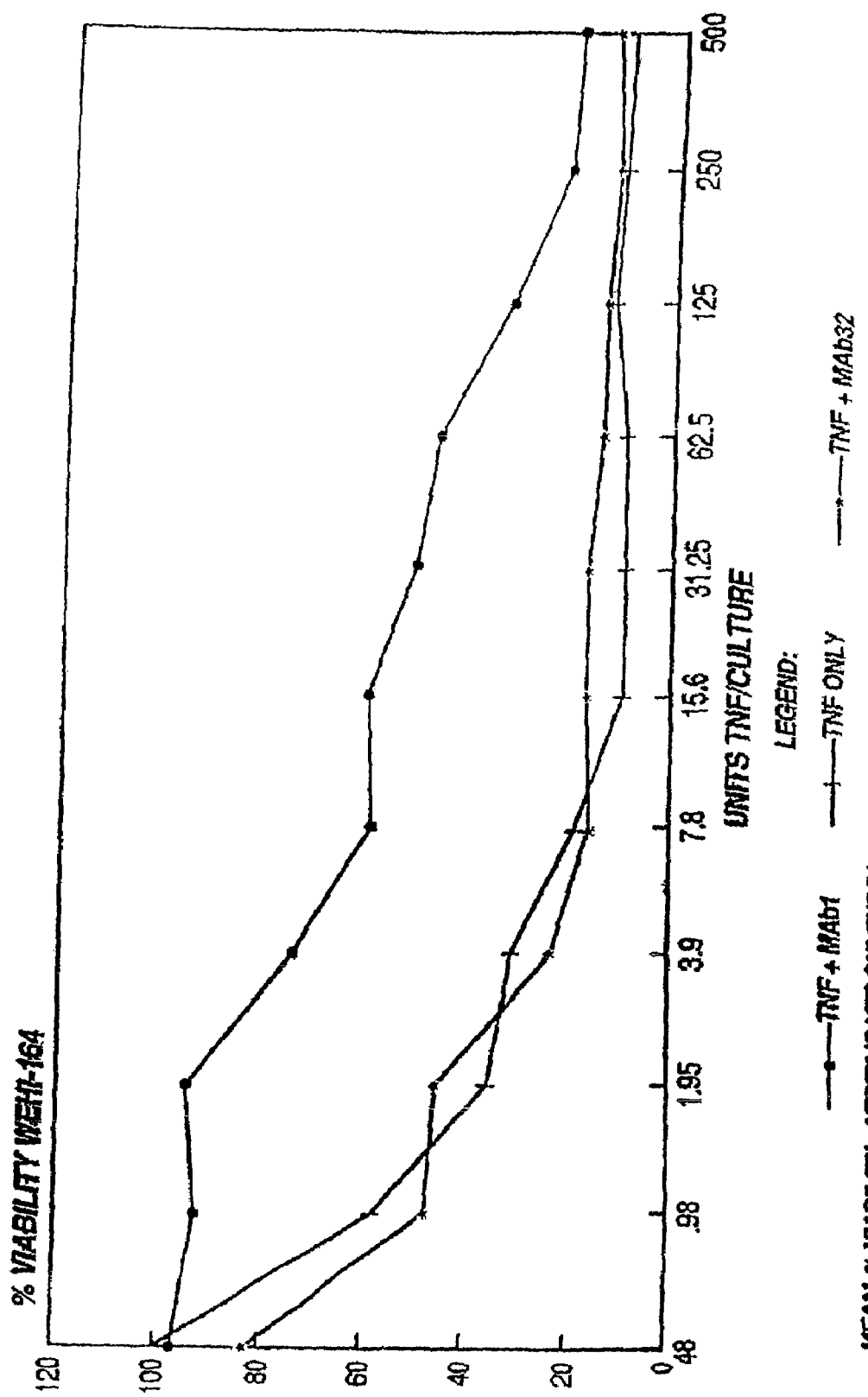
FIG. 3 shows the effect of anti-TNF monoclonal antibodies 1 and 32 on TNF cytotoxicity in WEHI-164 cells.

3. MAb neutralises the cytotoxic effect of recombinant human TNF on WEHI-164 mouse fibrosarcoma cells in culture. One microgram of MAb 1 neutralizes approximately 156.25 units of TNF in vitro (FIG. 3).

Figure 4:
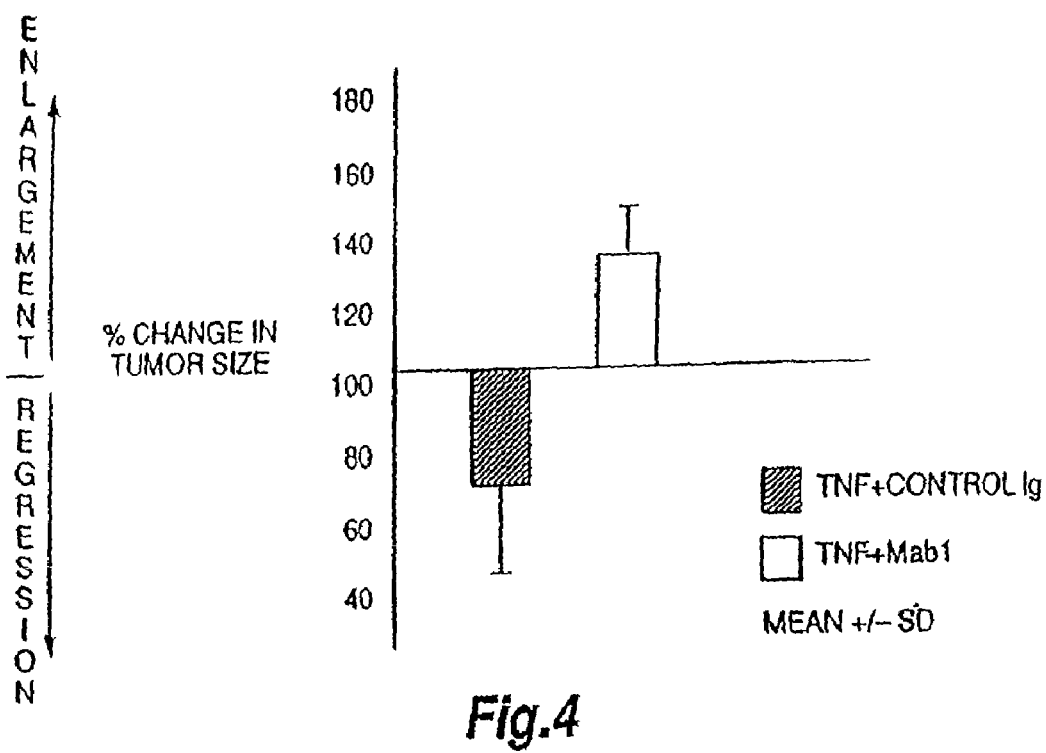
FIG. 4 shows the effect of MAb 1 on TNF-induced regression of a Meth A solid tumour.
Figure 5:
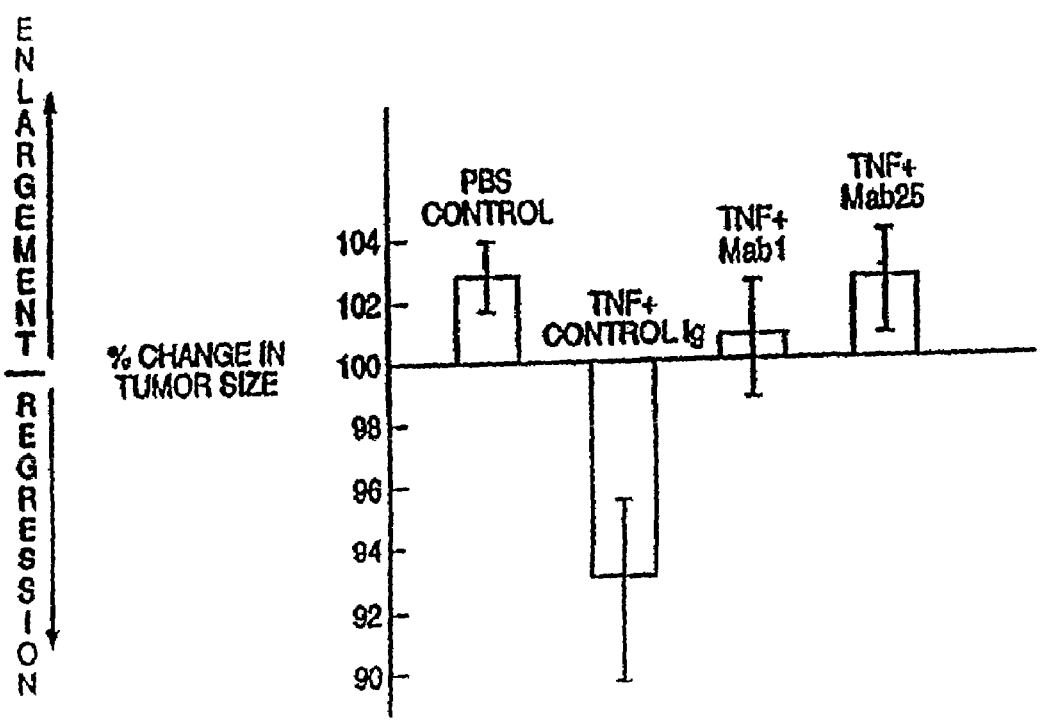
FIG. 5 shows the effect of MAbs 1 and 25 on TNF-induced Meth A Ascites tumour regression.
Figure 9:
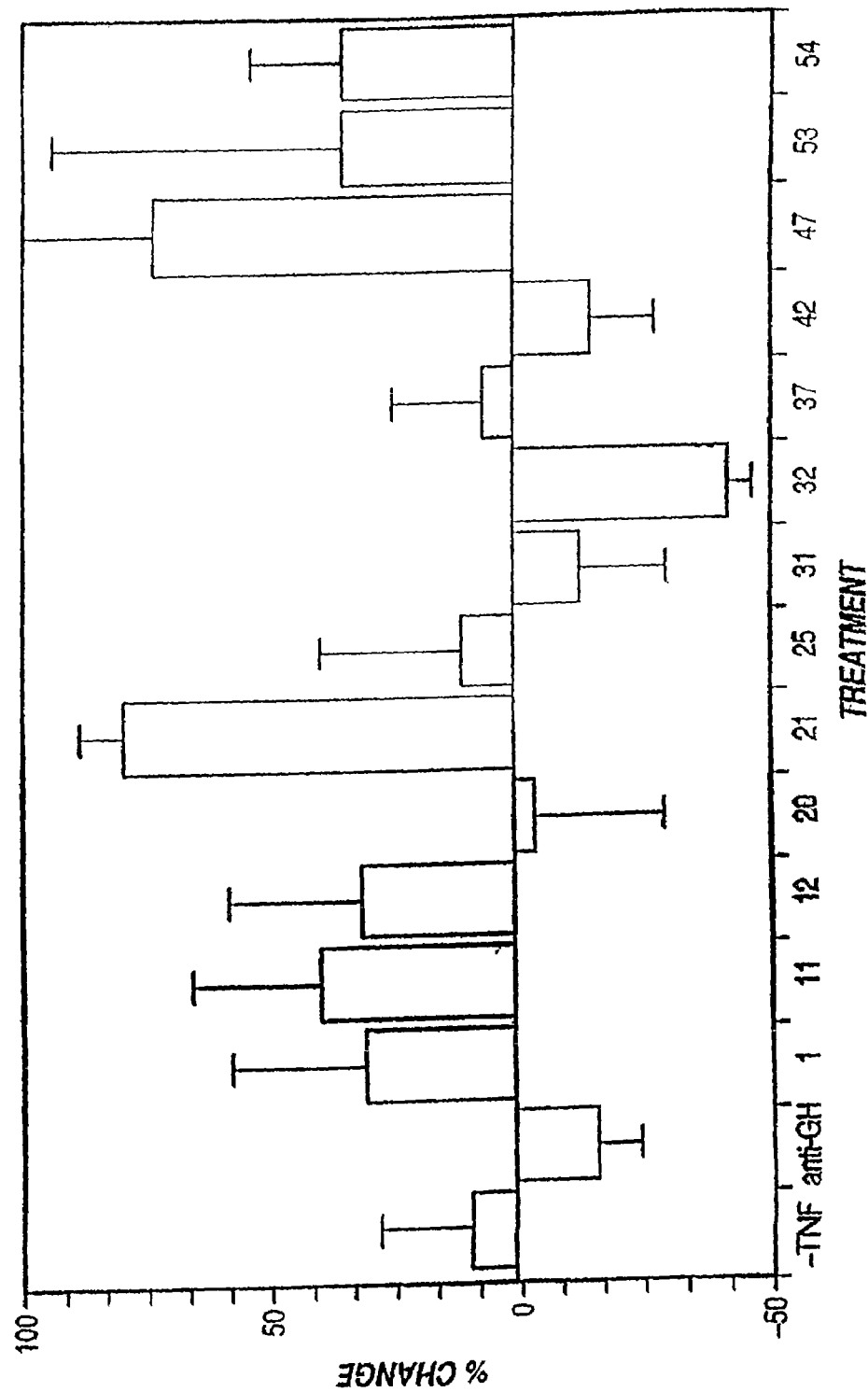
FIG. 9 shows the effect of anti-TNF MAbs on TNF-induced regression of WEHI-164 tumours.
Figure 10A:
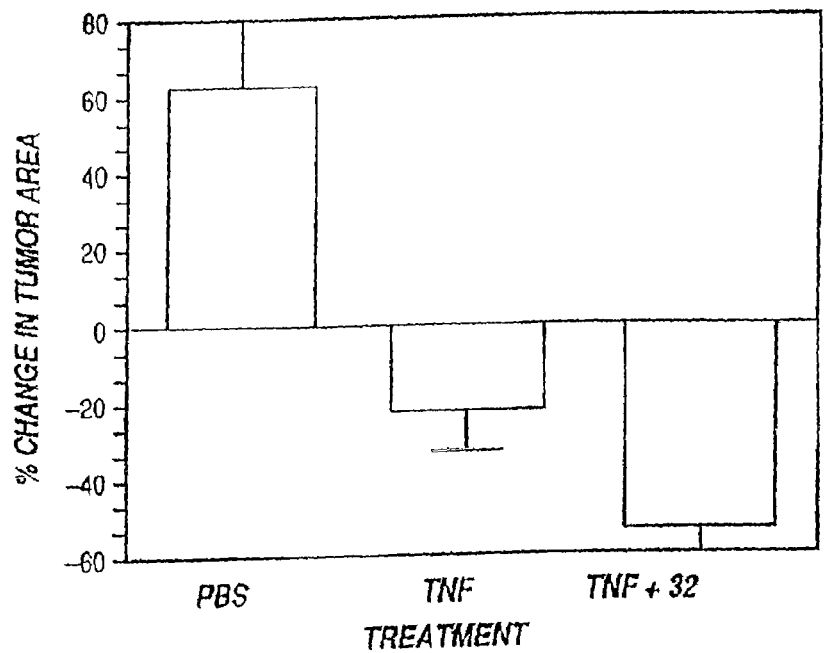
FIGS. 10a and 10b show the enhancement of TNF regression activity by MAb 32 in two experiments.
Figure 10B:
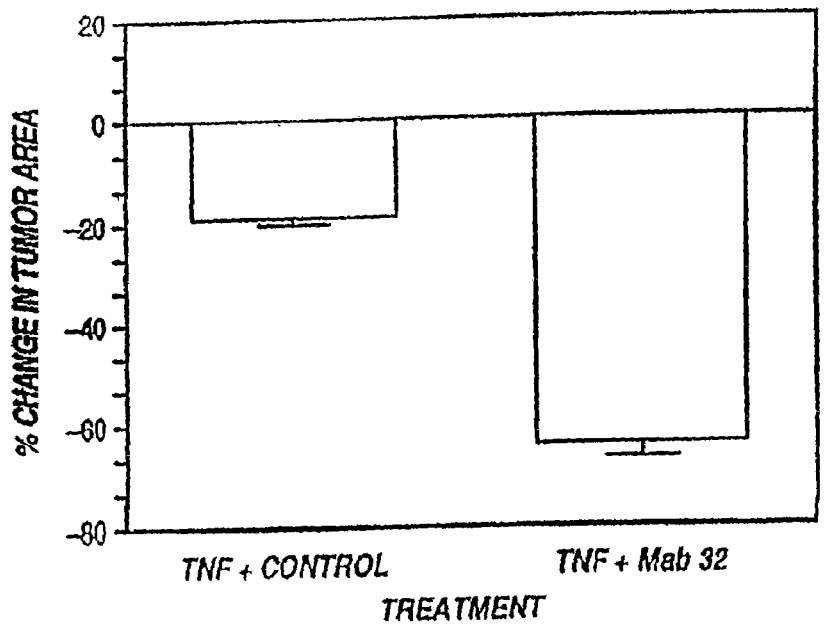
Figure 11A:
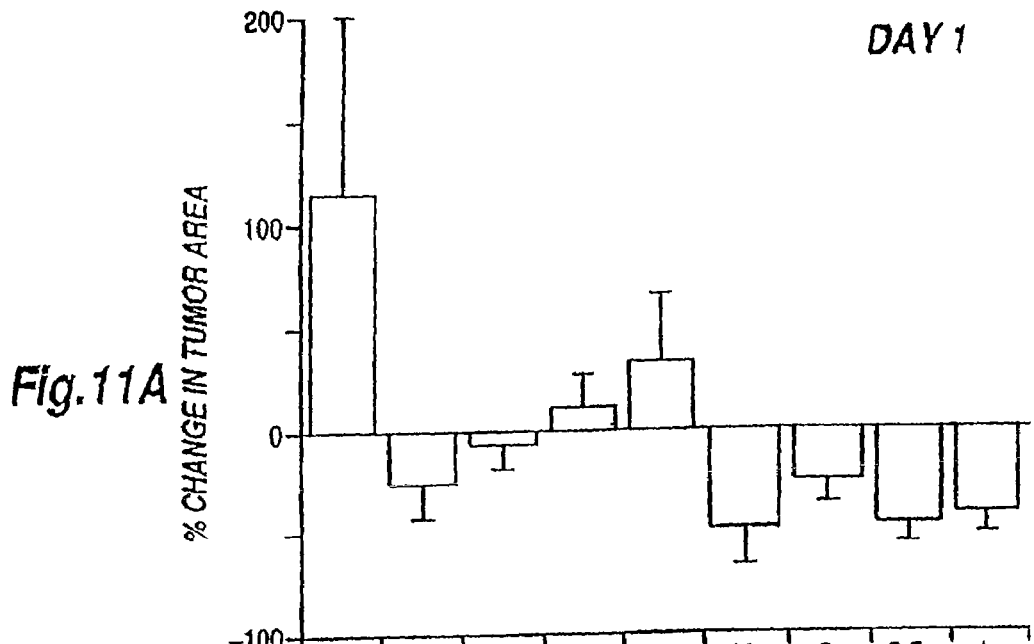
FIGS. 11a and 11b show the enhancement of TNF-induced tumour regression by MAb 32—dose response at day 1 and day 2.
Figure 11B:
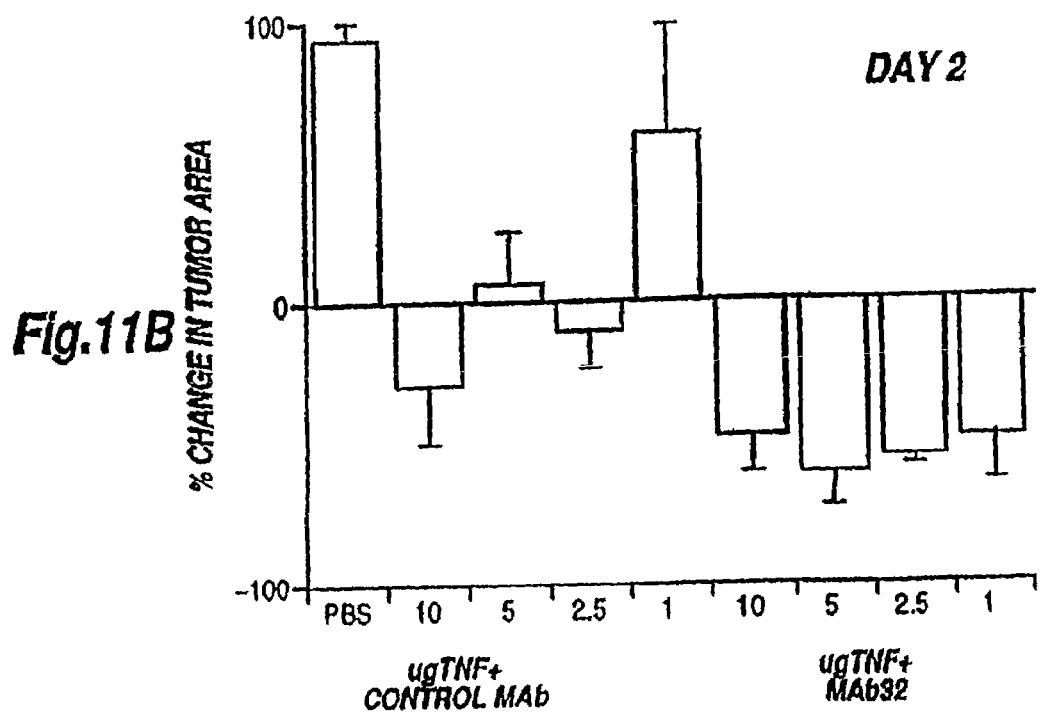

4. MAb 1 neutralises the tumour regression activity of TNF in the following mouse tumour models in vivo; WEHI-164 subcutaneous solid tumour, the Meth A subcutaneous solid tumour and the Meth A ascites tumour (FIGS. 4, 5 and 9).

5. MAb1 prevents cerebral damage caused by human TNF in mice infected with malarial parasites.

6. In radioreceptor assays MAb 1 prevents binding of TNF to receptors on WEHI-164 cells (Table 3).

Figure 6:
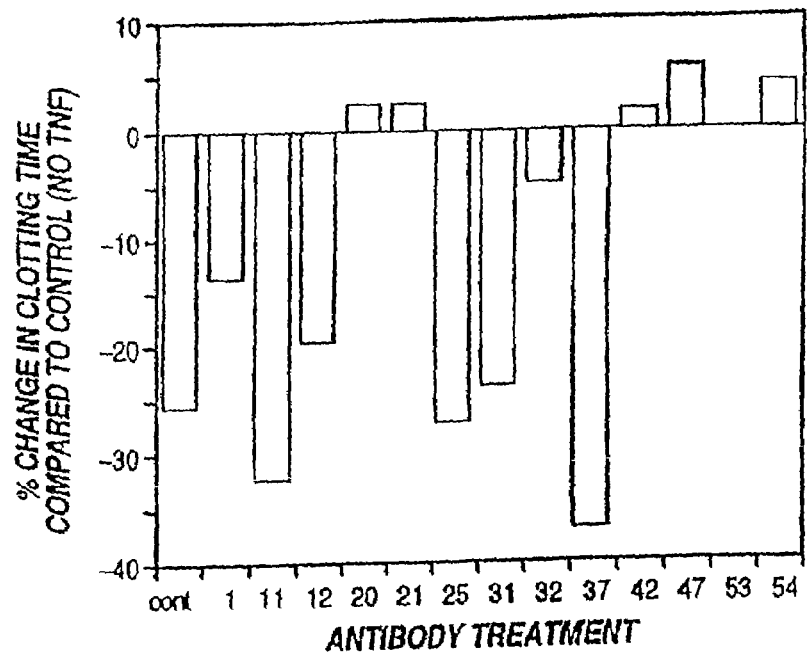
FIG. 6 shows the effect of anti-TNF MAbs on induction of endothelial cell procoagulant activity by TNF.

7. MAb 1 inhibits the induction of procoagulant activity (tissue factor) on cultured bovine aortic endothelial cells (FIG. 6).

8. MAb 1 reduces the uptake of 125I fibrinogen into tumours of mice treated with TNF FIGS. 7a-c).

9. MAb 1 competes for binding of 125I TNF and thus shares an overlapping epitope with the following monoclonal antibodies: 21, 25, 32, 47, 54 and 37.

Figure 8:
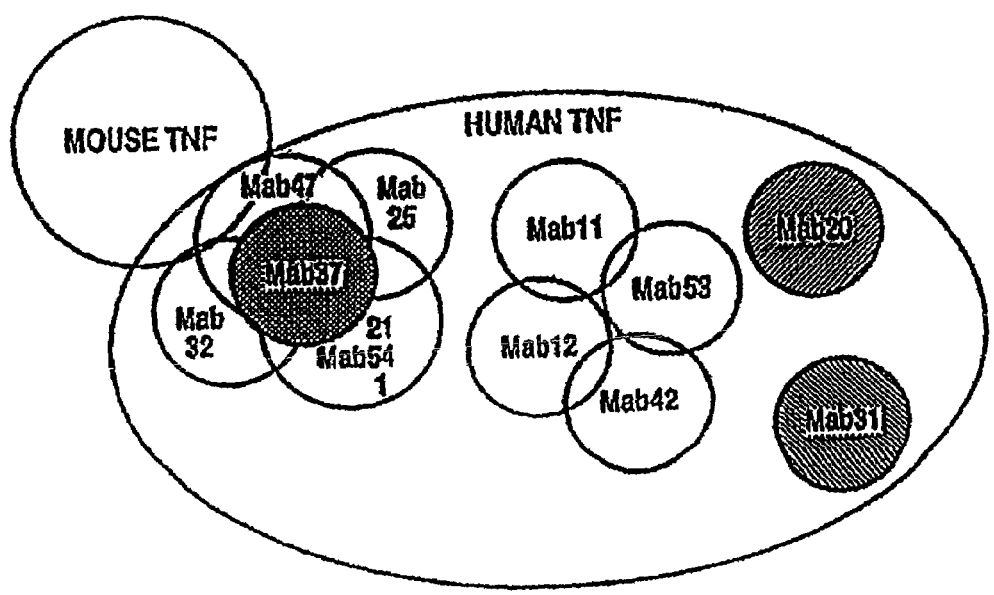
FIG. 8 is a schematic representation of epitopes on TNF.

10. MAb 1 does not compete for binding of 125I TNF with the following monoclonal antibodies: 11, 12, 42, 53, 31 and 20 (FIG. 8).

TABLE 3

RADIORECEPTOR ASSAY:
INHIBITION OF TNF BINDING TO WEHI-164 CELLS BY MAb 1

| TREATMENT | | % SPECIFIC BINDING |
|---|---|---|
| MAb 1 | 1/10 | 0 |
| | 1/100 | 21 |
| | 1/1,000 | 49 |
| | 1/10,000 | 73 |
| | 1/100,000 | 105 |
| cold TNF (ng/tube) | | |
| | 10,000 | 0 |
| | 5,000 | 0 |
| | 1,000 | 0 |

TABLE 3-continued

RADIORECEPTOR ASSAY:
INHIBITION OF TNF BINDING TO WEHI-164 CELLS BY MAb 1

| TREATMENT | % SPECIFIC BINDING |
|---|---|
| 500 | 10 |
| 100 | 11 |
| 10 | 64 |
| 1 | 108 |
| 0 | 100 |

MAb 32 is an IgG2b,K antibody with an affinity for human TNF alpha of $8.77 \times 10^{-9}$ moles-liter as determined by Scatchard analysis. This monoclonal antibody does not react with either human TNF beta (lymphotoxin) or mouse TNF alpha.

As shown in FIG. 3 MAb 32 does not inhibit TNF cytotoxicity in vitro as determined in the WEHI-164 assay.

Monoclonal antibody 32 variably enhances TNF-induced tumour regression activity against WEHI-164 fibrosarcoma tumours implanted subcutaneously into BALB/c mice at a TNF dose of 10 μg/day (see FIGS. 10a-b and 11a-b). This feature is not common to all monoclonal antibodies directed against TNF (FIG. 9) but resides within the binding site specificity of MAb 32 (FIG. 8) which may allow greater receptor mediated uptake of TNF into tumour cells (see Table 4).

TABLE 4

BINDING OF TNF TO RECEPTORS ON WEHI-164 CELLS
IN THE PRESENCE OF MAb 32

| | % BINDING$^{125}$ I-TNF | |
|---|---|---|
| MAB DILUTION | CONTROL MAB | MAB 32 |
| 1/10 | 36 | 141 |
| 1/100 | 74 | 88 |
| 1/1000 | 101 | 83 |
| 1/10,000 | 92 | 82 |
| 1/100,000 | 97 | 93 |

Figure 18:
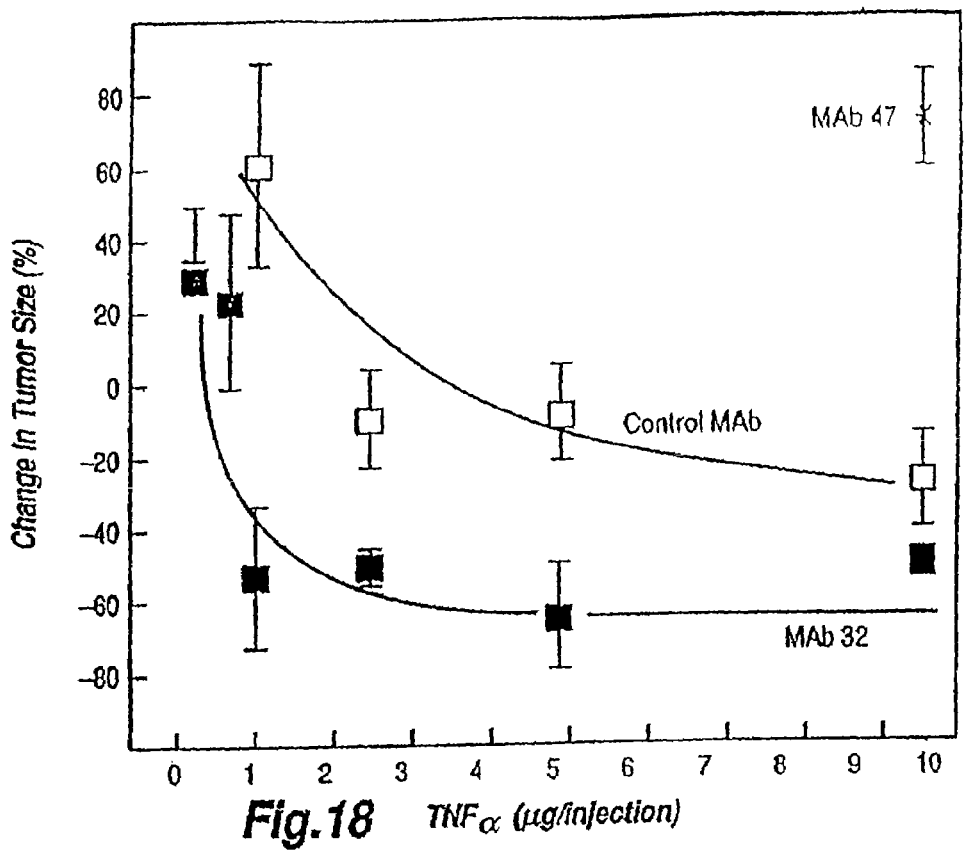
FIG. 18 shows the effect on TNF-mediated tumour regression in vivo by MAb 32 ( ) control MAb (□) and MAb 47 (*)
Figure 19:
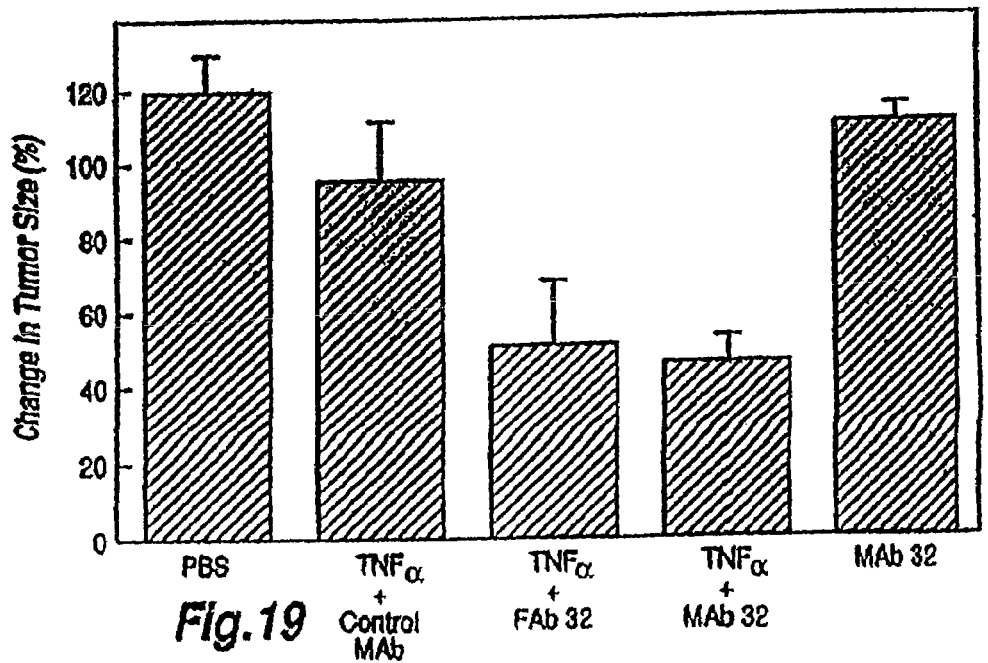
FIG. 19 shows the effect on TNF-mediated tumour regression in vivo by control MAb, MAb 32 and univalent FAb' fragments of MAb 32.

Enhancement of TNF activity by MAb 32 at lower doses of TNF is such that at least tenfold less TNF is required to achieve the same degree of tumour regression (see FIGS. 11 and 18). The results for day 1, 2.5 ug and 1 ug TNF and day 2, 5 ug, 2.5 ug and 1 ug are statistically significant in a t-test at p<0.01 level. This level of enhancement also increases the survival rate of recipients since the lower dose of TNF used is not toxic. FIG. 19 shows that univalent Fab fragments of MAb 32 also cause enhancement of TNF-induced tumour regression in the same manner as whole MAb 32 (see below).

MAb 32 inhibits the expression of clotting factors on endothelial cells normally induced by incubation of the cultured cells with TNF (see FIG. 6). This response may be mediated by a previously unidentified TNF receptor which is distinct to the receptor found on other cells.

Figure 7A:
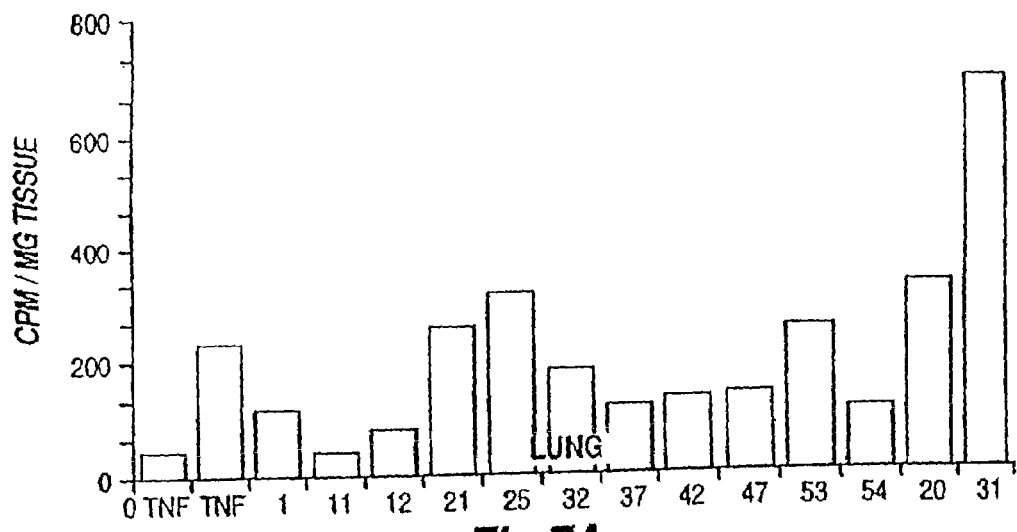
FIGS. 7a, 7b and 7c show incorporation of labeled fibrinogen into tumours of tumour-bearing mice and the effect of anti-TNF MAbs.
Figure 7B:
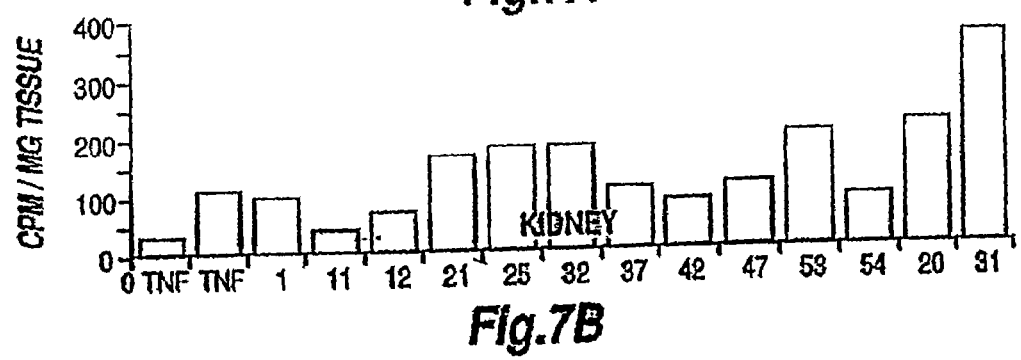
Figure 7C:
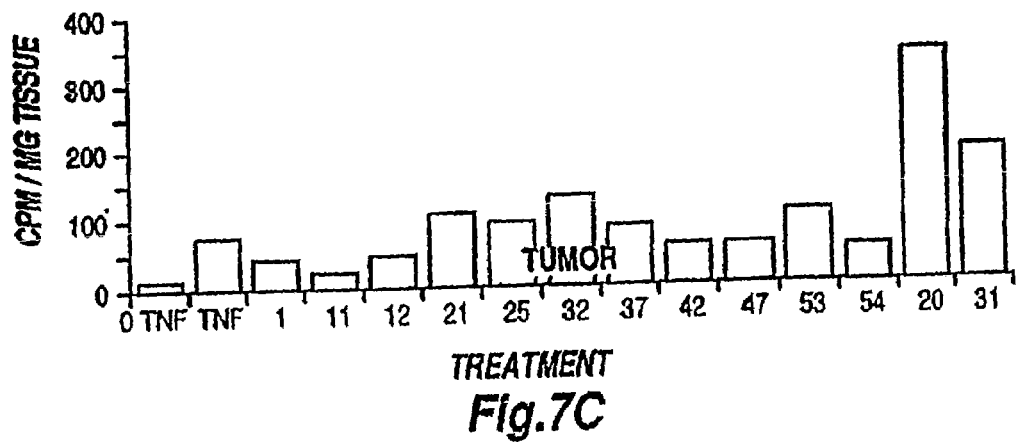

Conversely, MAb 32 enhances the in vivo activation of coagulation within the tumour bed as shown by the incorporation of radiolabelled fibrinogen (FIGS. 7a-c). This may be due to activation of monocytes/macrophage pro coagulant and may provide further insight into the mechanism of TNF-induced tumour regression.

The results obtained with MAb 32 are shown in comparison to other anti-TNF MAbs in Table 2.

The ability of MAb 32 and MAb 47 to inhibit the binding of TNF to endothelial cells was also assessed. Bovine aortic endothelial (BAE) cells (passage 11) were plated in 24-well culture dishes (Corning) which had been pre-coated with gelatin (0.2%) and grown to confluence in McCoys 5A (modified) medium supplemented with 20% foetal calf serum. For the radio-receptor assay all dilutions (of cold TNF and MAbs) were made in this medium. The BAE cells were incubated for one hour in the presence of either cold TNF (0 to 100 ng) or MAb (ascites globulins diluted 1/100 to 1/1000, 000) and iodinated TNF (50,000 cpm). At the end of this time the medium was withdrawn and the cells washed before being lysed with 1M sodium hydroxide. The cell lysate was then counted for bound radioactive TNF. Specific binding of labelled TNF to the cells was then determined.

Figure 12:
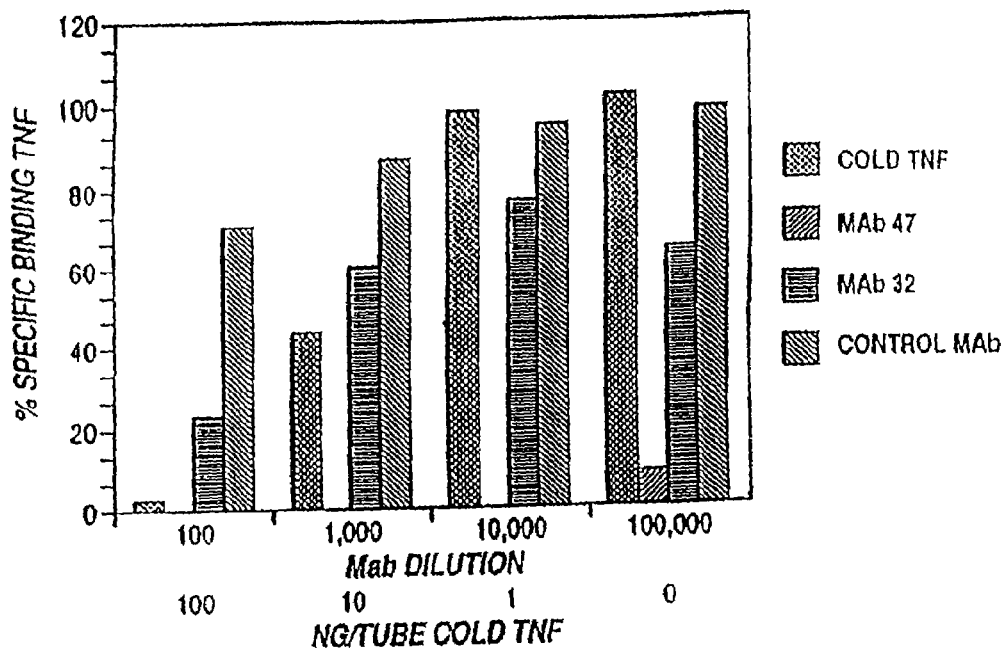
FIG. 12 shows binding of radio labelled TNF to receptors on bovine aortic endothelial cells.
Figure 13:
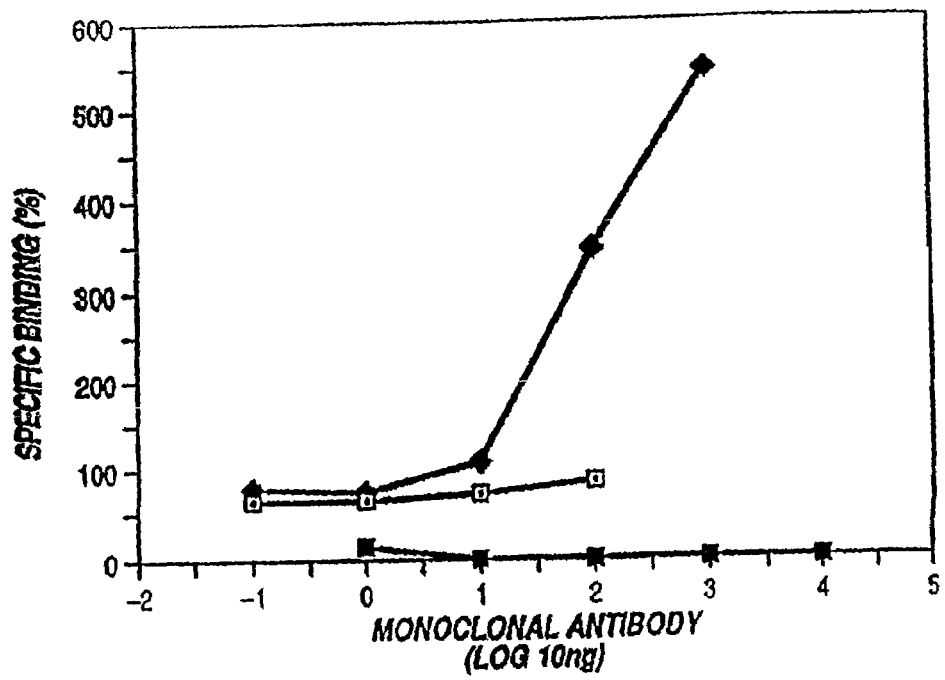
FIG. 13 shows receptor binding studies of TNF complexed with MAb 32 (◆), control antibody (□) and MAb 47 (■) on melanoma cell line MM418E.
Figure 14:
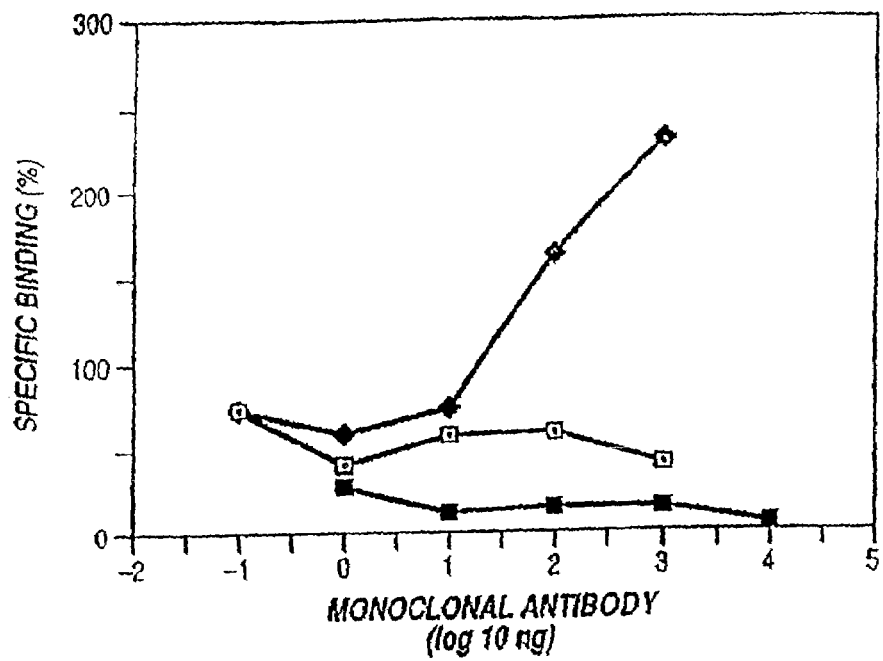
FIG. 14 shows receptor binding studies of TNF complexed with MAb 32 (◆), control antibody (□) and MAb 47 (■) on melanoma cell line IGR3.
Figure 15:
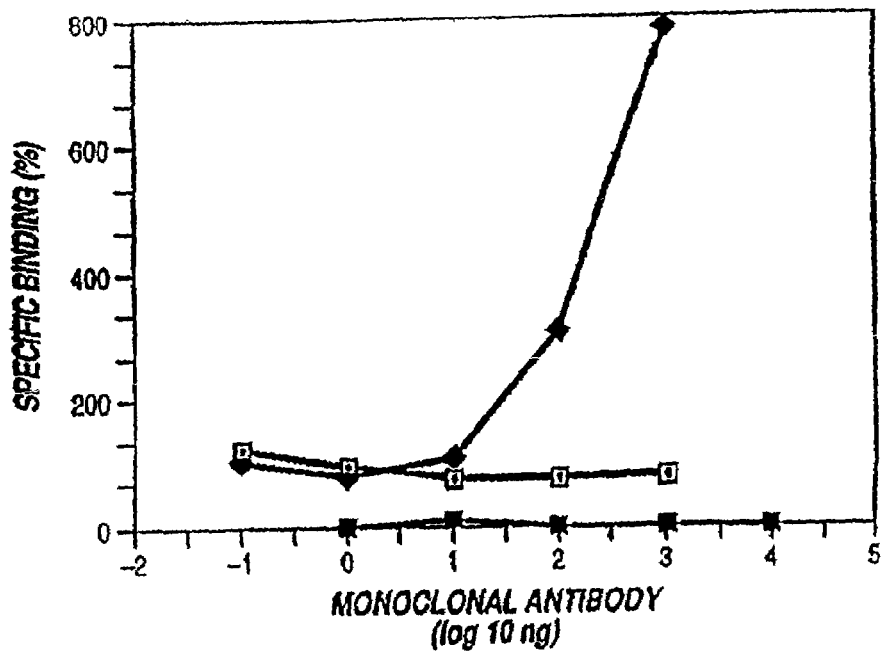
FIG. 15 shows receptor binding studies of TNF complexed with MAb 32 (◆), control antibody (□) and MAb 47 (■) on bladder carcinoma cell line S637.

The results obtained in this assay with MAb 32, MAb 47 and a control MAb are set out in FIG. 12.

The results obtained in the clotting assay using BAE cells cultured in the presence of TNF and anti-TNF MAb correlate with the results obtained in the BAE radioreceptor assay i.e. MAbs which inhibit the induction of clotting factors on the surface of endothelial cells (as shown by the increase in clotting time compared to TNF alone) also inhibit the binding of TNF to its receptor. This is exemplified by MAbs 32 and 47.

MAb 32, which does not inhibit TNF binding to WEHI-164 cells, does inhibit binding of TNF to endothelial cells. This result provides support for the hypothesis that distinct functional sites exist on the TNF molecule and that these sites interact with distinct receptor subpopulations on different cell types. Thus ligands which bind to defined regions of TNF are able to modify the biological effects of TNF by limiting its binding to particular receptor subtypes.

As shown in FIG. 12 MAb 47 is a particularly potent inhibitor of TNF interaction with endothelial cells, the percentage specific binding at a dilution of 1/100 to 1/10,000 being effectively zero.

Receptor Binding Studies of Human TNF Complexed with MAb 32 on Human Carcinoma Cell Lines In Vitro MAb 32 has been shown to enhance the anti-tumour activity of human TNF. The mechanisms behind the enhancement may include restriction of TNF binding to particular (tumour) receptor subtypes but not others (endothelial) with subsequent decrease in TNF toxicity to non-tumour cells. This mechanism does not require enhanced uptake of TNF by tumour cells in vitro assays. In addition, MAb 32 also potentiates the binding of human TNF directly to TNF receptors on certain human carcinoma cell lines.

Materials and Methods

The following human carcinoma cell lines have been assayed for enhanced receptor-mediated uptake of TNF in the presence of MAb 32; B10, CaCo, HT 29, SKC01 (all colon carcinomas), S637 (Bladder carcinoma), MM418E (melanoma), IGR3 (melanoma) MCF 7 (breast carcinoma). The cells were propagated in either RPMI-1640 (MM418E) DMEM (CaCo and IGR 3) or Iscoves modified DMEM (B10, HT 29, SK01, S637, MCF 7) supplemented with 10% foetal calf serum, penicillin/streptomycin and L-glutamine. Receptor assays were performed as previously described for endothelial cells except that the incubation time with iodinated TNF was extended to 3 hours for all but the 810 cells for which the radiolabel was incubated for 1 hour.

Results

Figure 16:
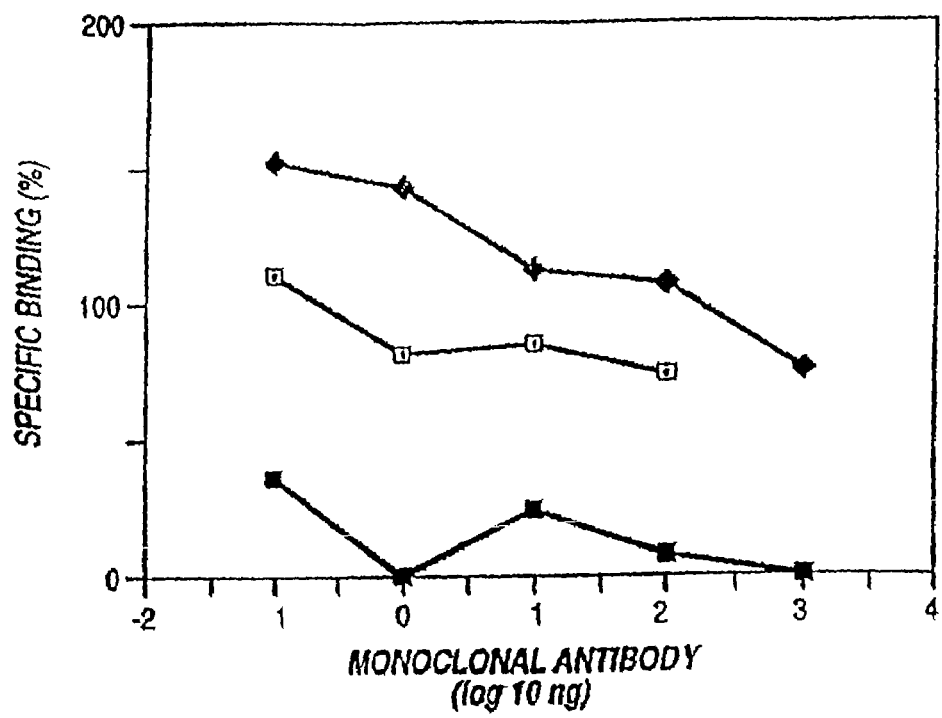
FIG. 16 shows receptor binding studies of TNF complexed with MAb 32 (◆), control antibody (□) and MAb 47 (■) on breast carcinoma cell line MCF7.
Figure 17:
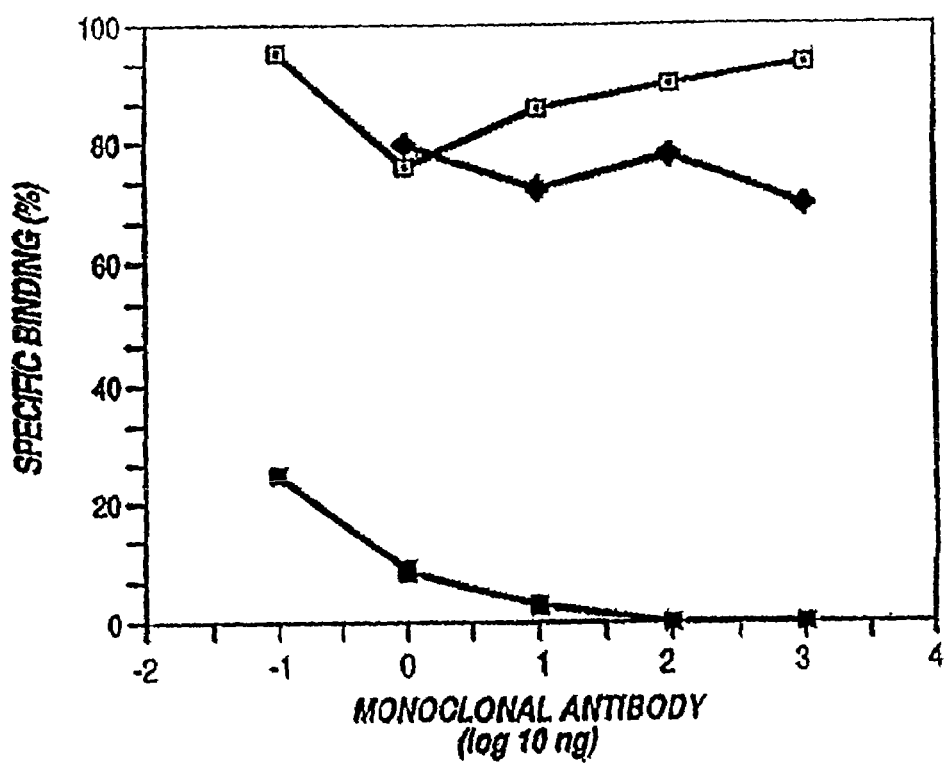
FIG. 17 shows receptor binding studies of TNF completed with MAb 32 (◆), control antibody (□) and MAb 47 (■) on colon carcinoma cell line B10.

Enhanced TNF uptake was observed in the presence of MAb32 by the melanoma cell lines tested MM418E and IGR 3 (FIGS. 13 and 14), the bladder carcinoma S637 (FIG. 15), and the breast carcinoma MCF 7 (FIG. 16). MAb 32 did not affect TNF-receptor interaction in any of the other cell lines as shown by B 10 (FIG. 17) MAb 47, which has been to shown to inhibit TNF binding to WEHI-164 cells and endothelial cells, and which also inhibits TNF-mediated tumour regression was found to markedly inhibit TNF binding to all the cell lines tested (FIGS. 13-17).

Conclusions

Receptor binding analyses have indicated a second mechanism whereby MAb 32 may potentiate the anti-tumour activity of TNF. This second pathway for enhancement of TNF results from increased uptake of TNF by tumour all receptors in the presence of MAb 32.

Enhancement of TNF-Mediated Tumour Regression In Vivo by MAb 32 or Univalent FAB' Fragments of MAb 32

Figure 22:
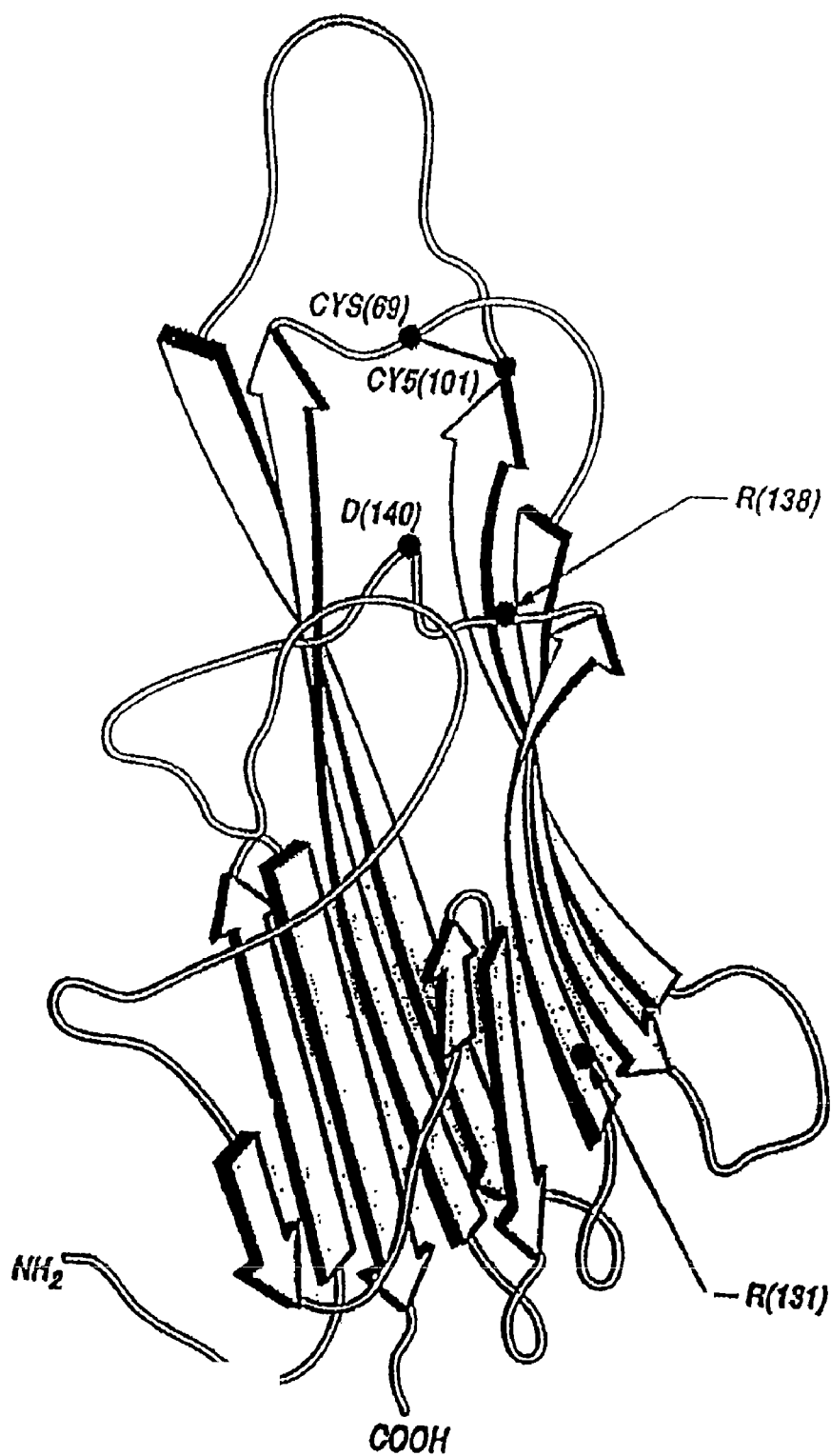
FIG. 22 shows a schematic three dimensional representation of the TNF molecule.
Figure 23:
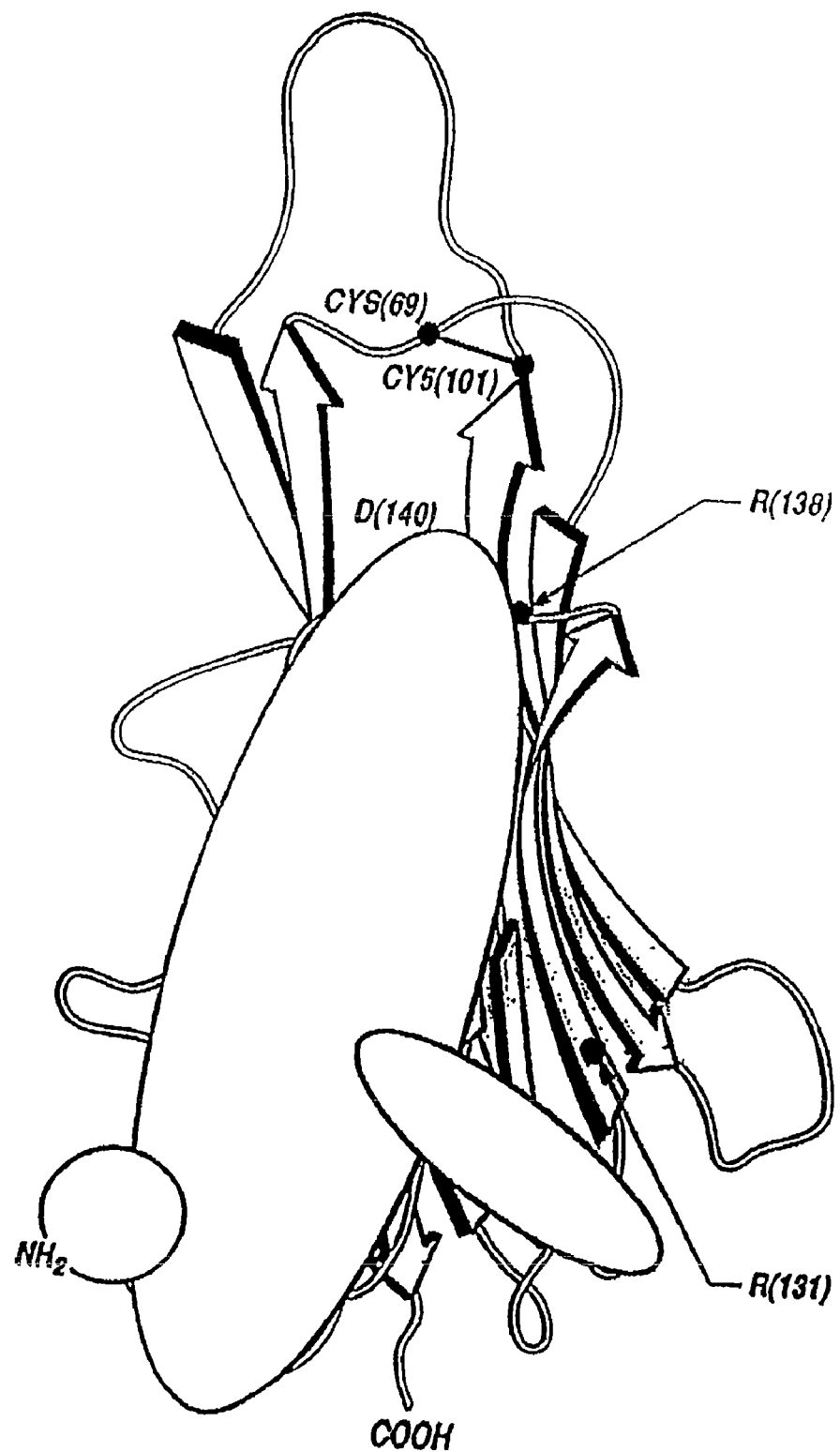
FIG. 23 shows topographically the region of residues 1-20, 56-77, 108-127 and 138-149.
Figure 24:
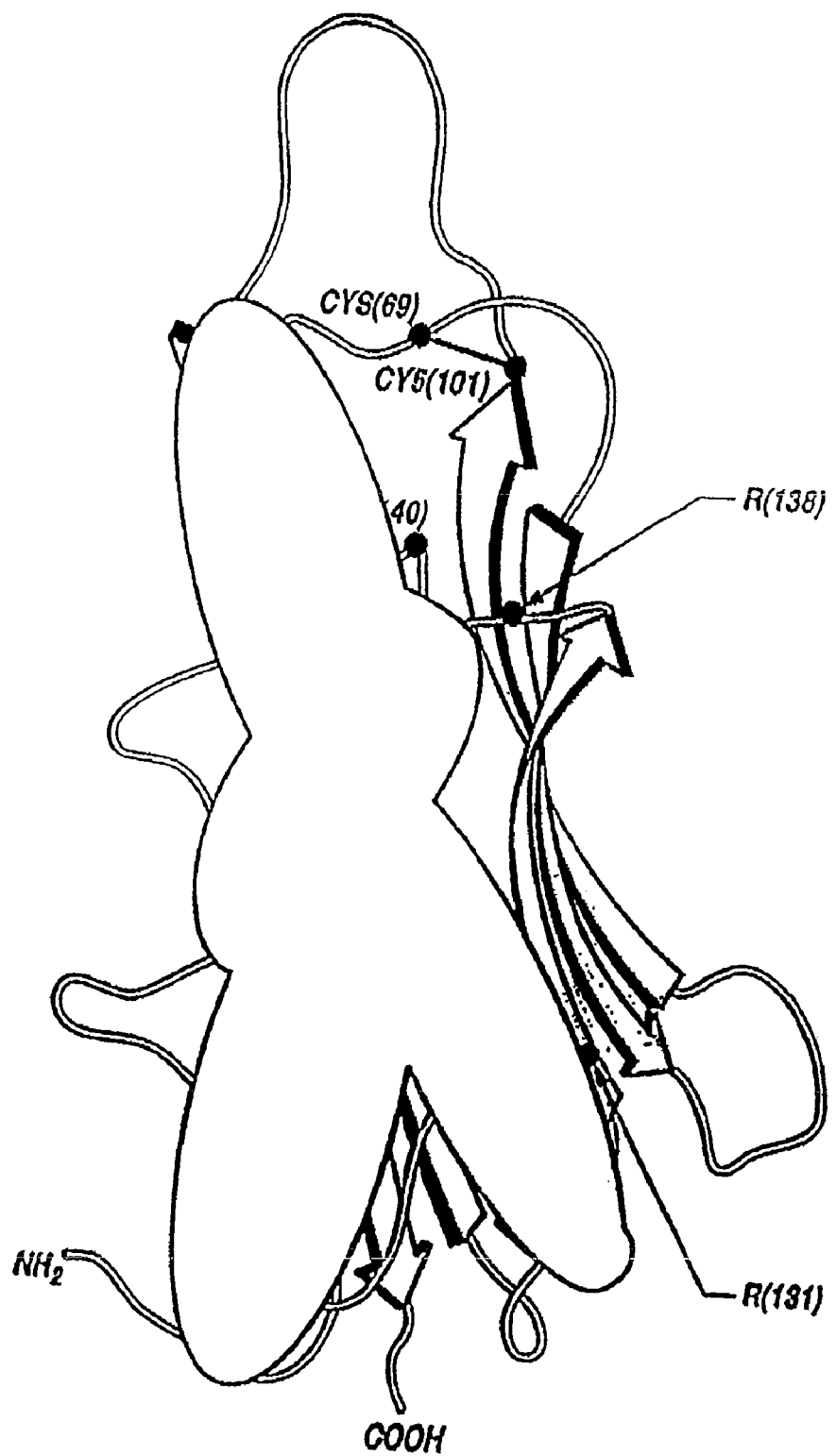
FIG. 24 shows topographically the region of residues 1-18 and 108-128.
Figure 25:
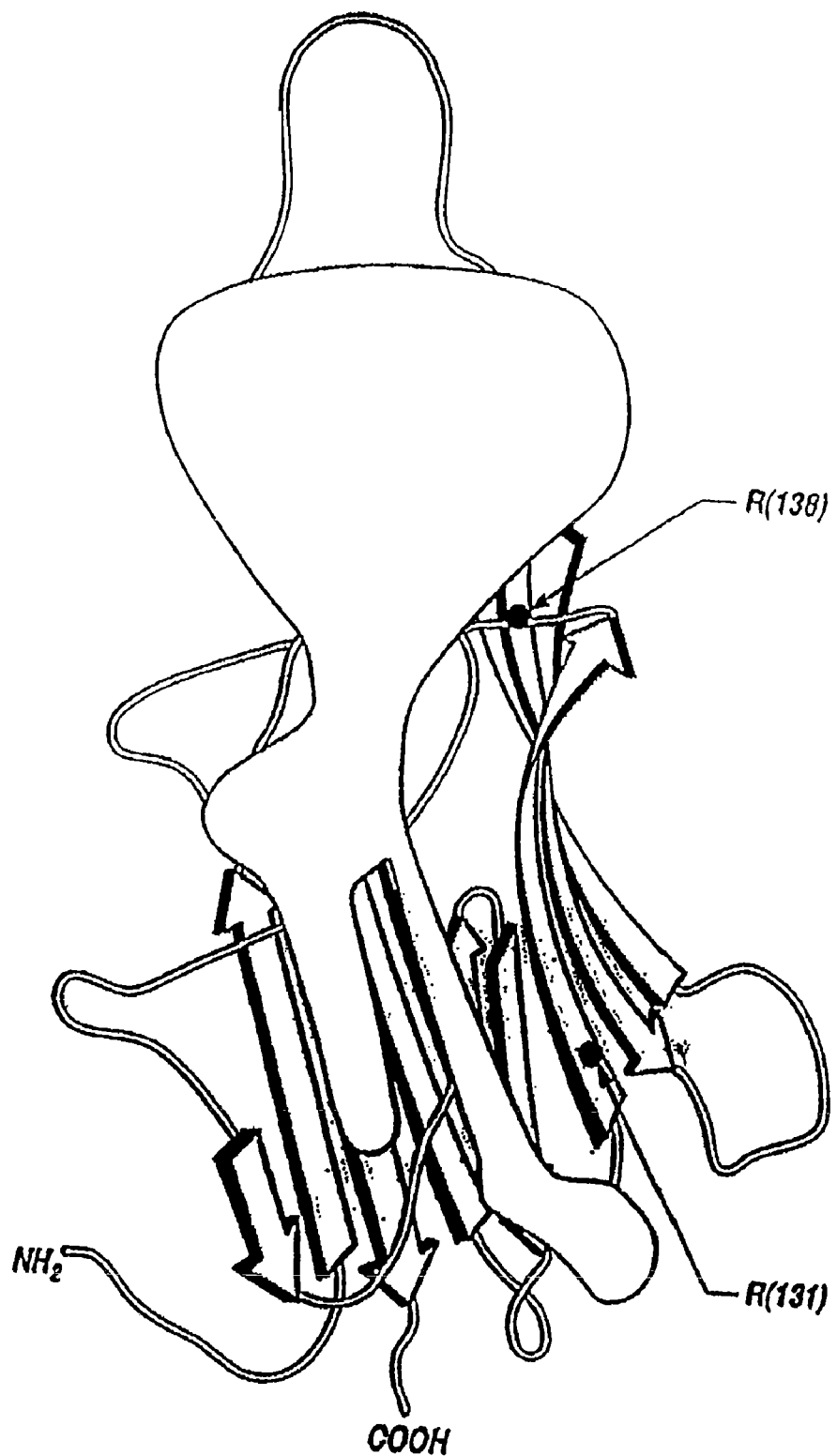
FIG. 25 shows topographically the region of residues 56-79, 110-127 and 136-155.
Figure 26:
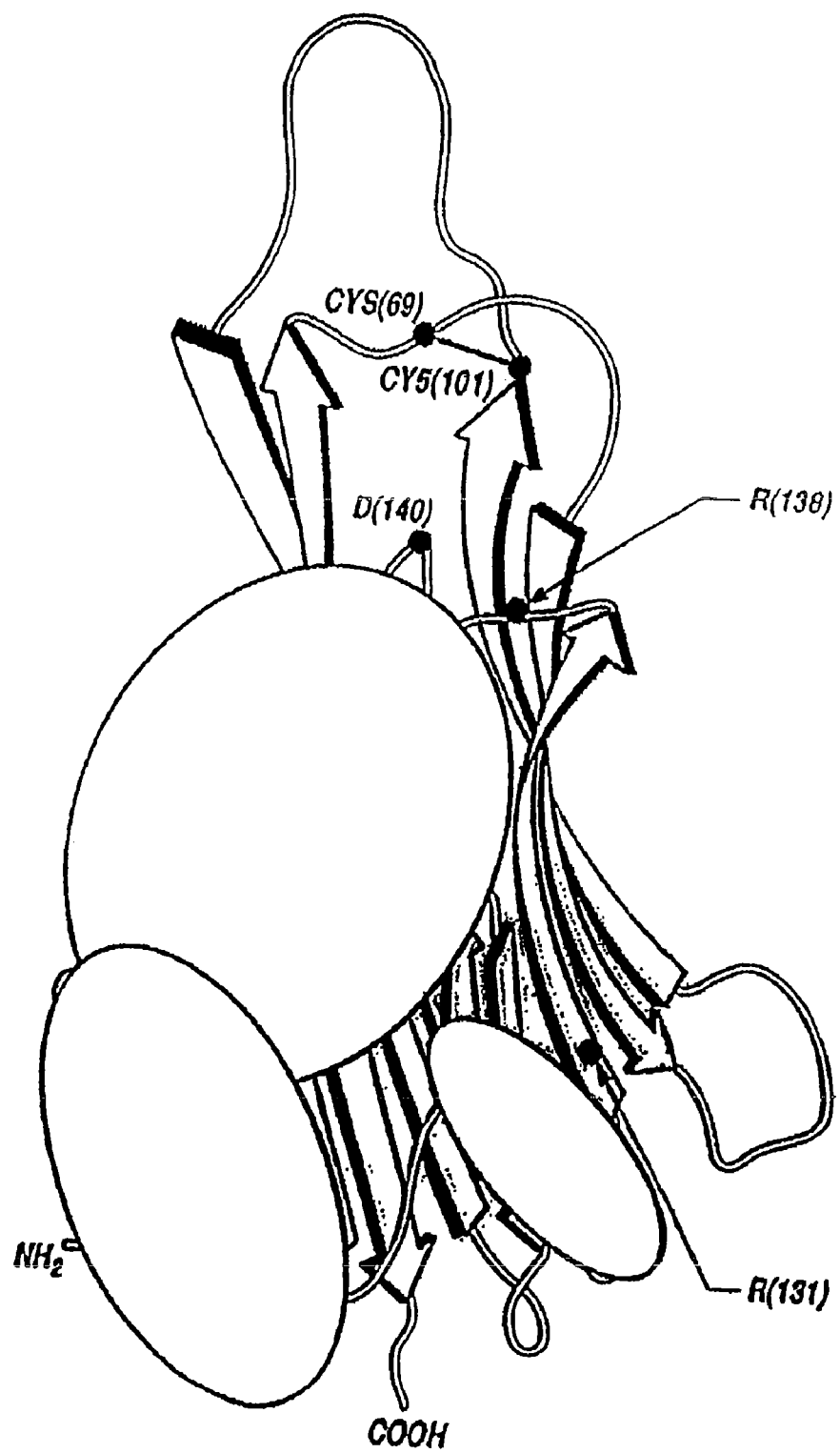
FIG. 26 shows topographically the region of residues 1-26, 117-128 and 141-153.
Figure 27:
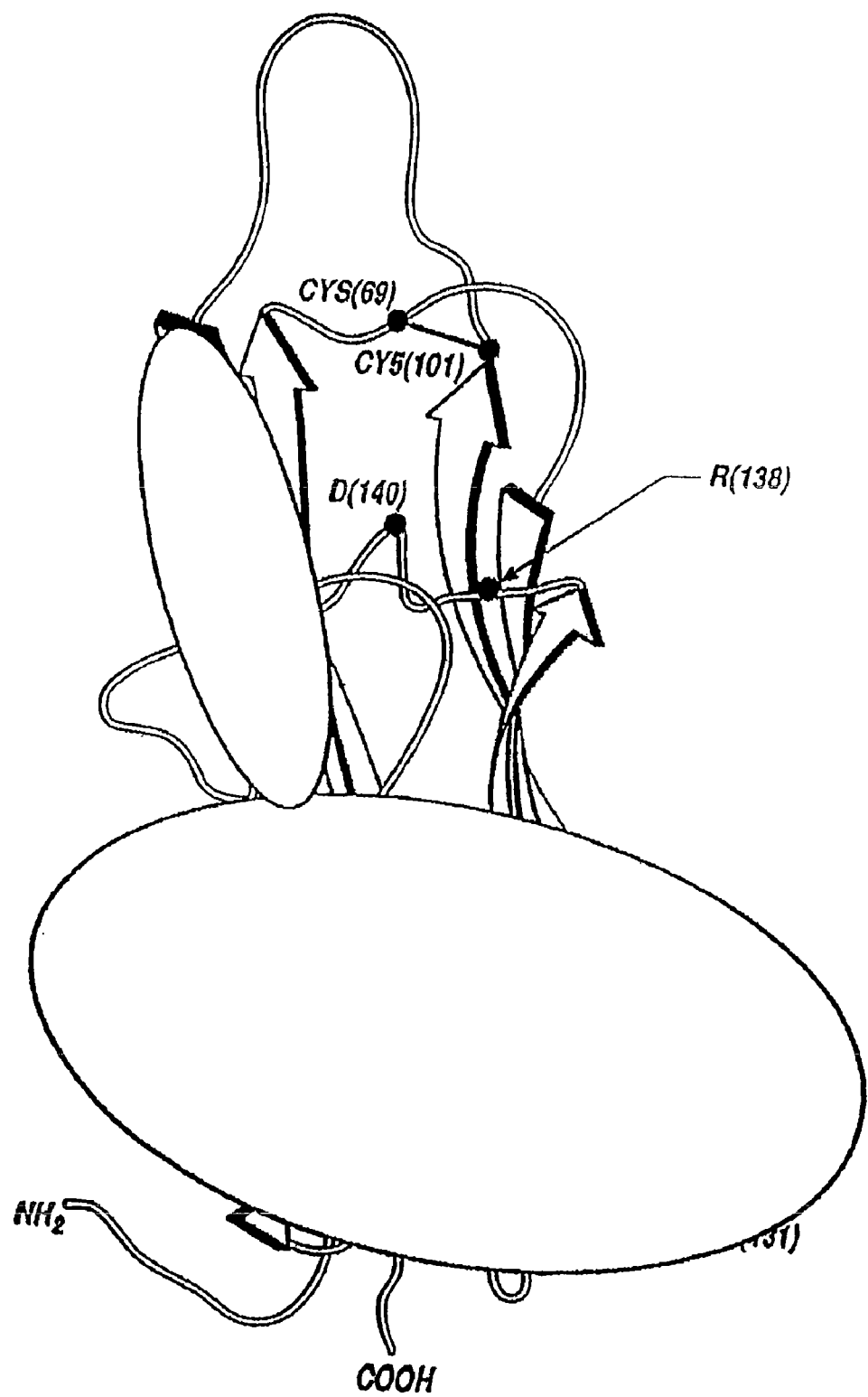
FIG. 27 shows topographically the region of residues 22-40, 49-97, 110-127 and 136-153.
Figure 28:
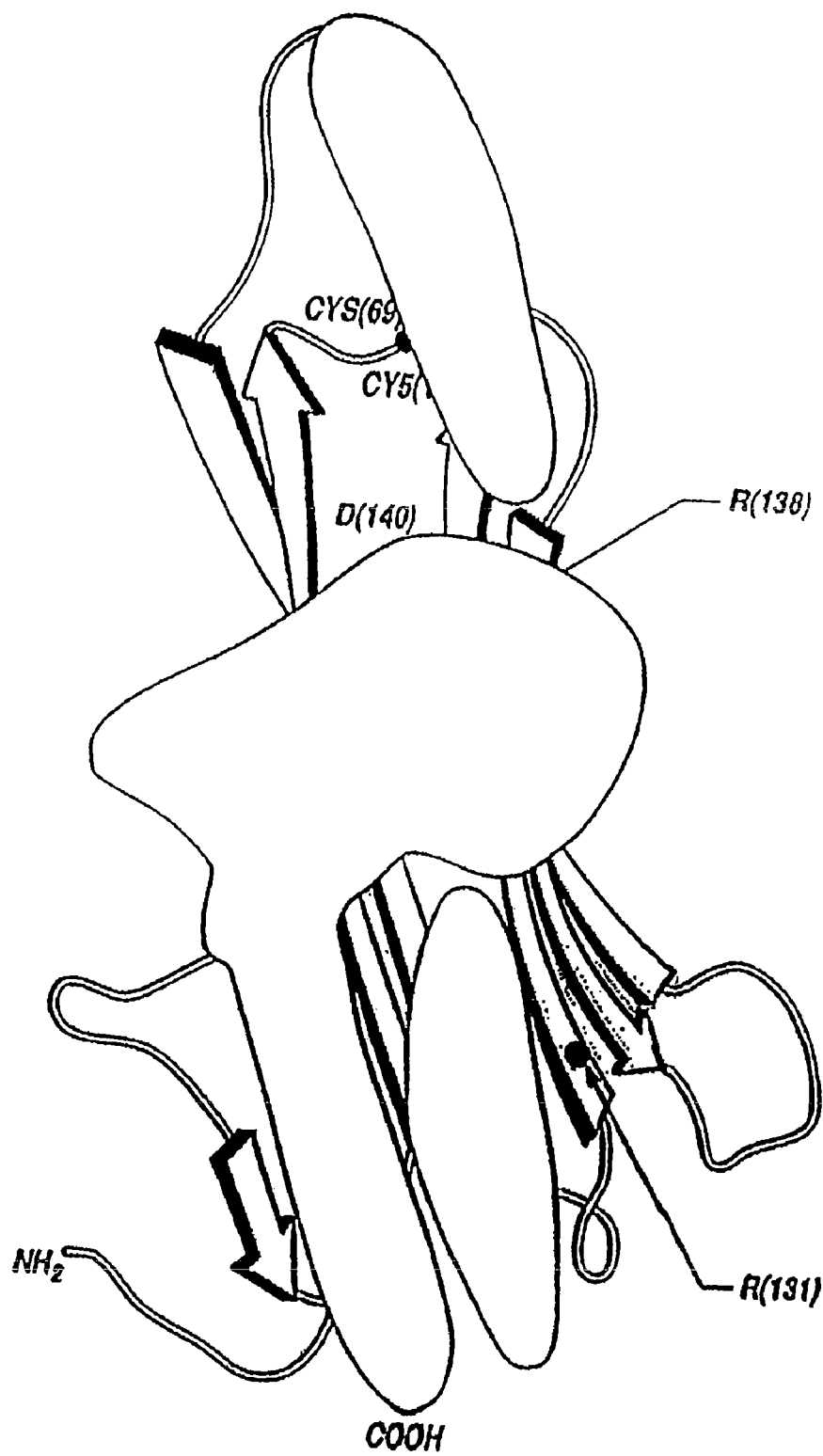
FIG. 28 shows topographically the region of residues 12-22, 36-45, 96-105 and 132-157.
Figure 29:
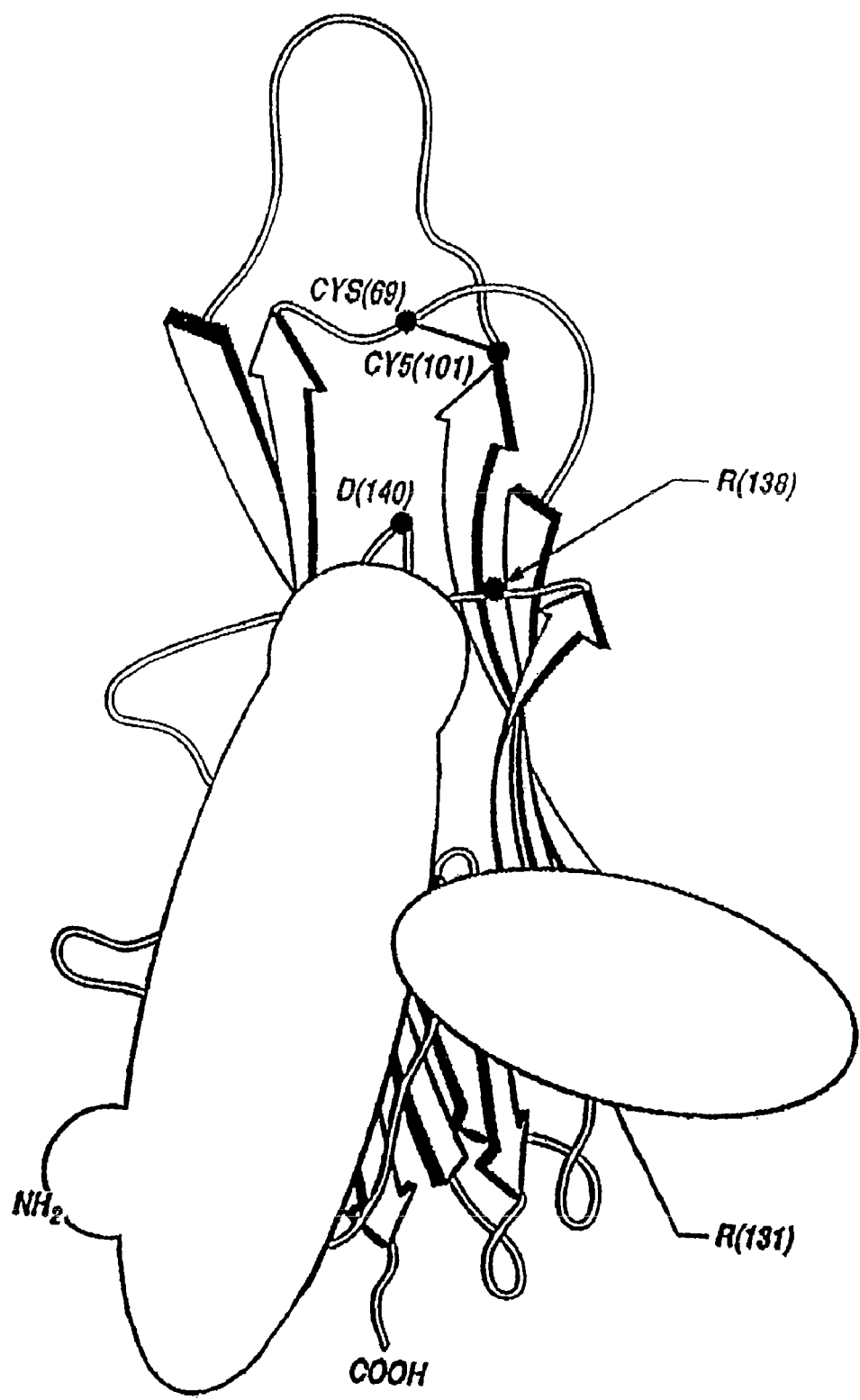
FIG. 29 shows topographically the region of residues 1-20 and 76-90.
Figure 30:
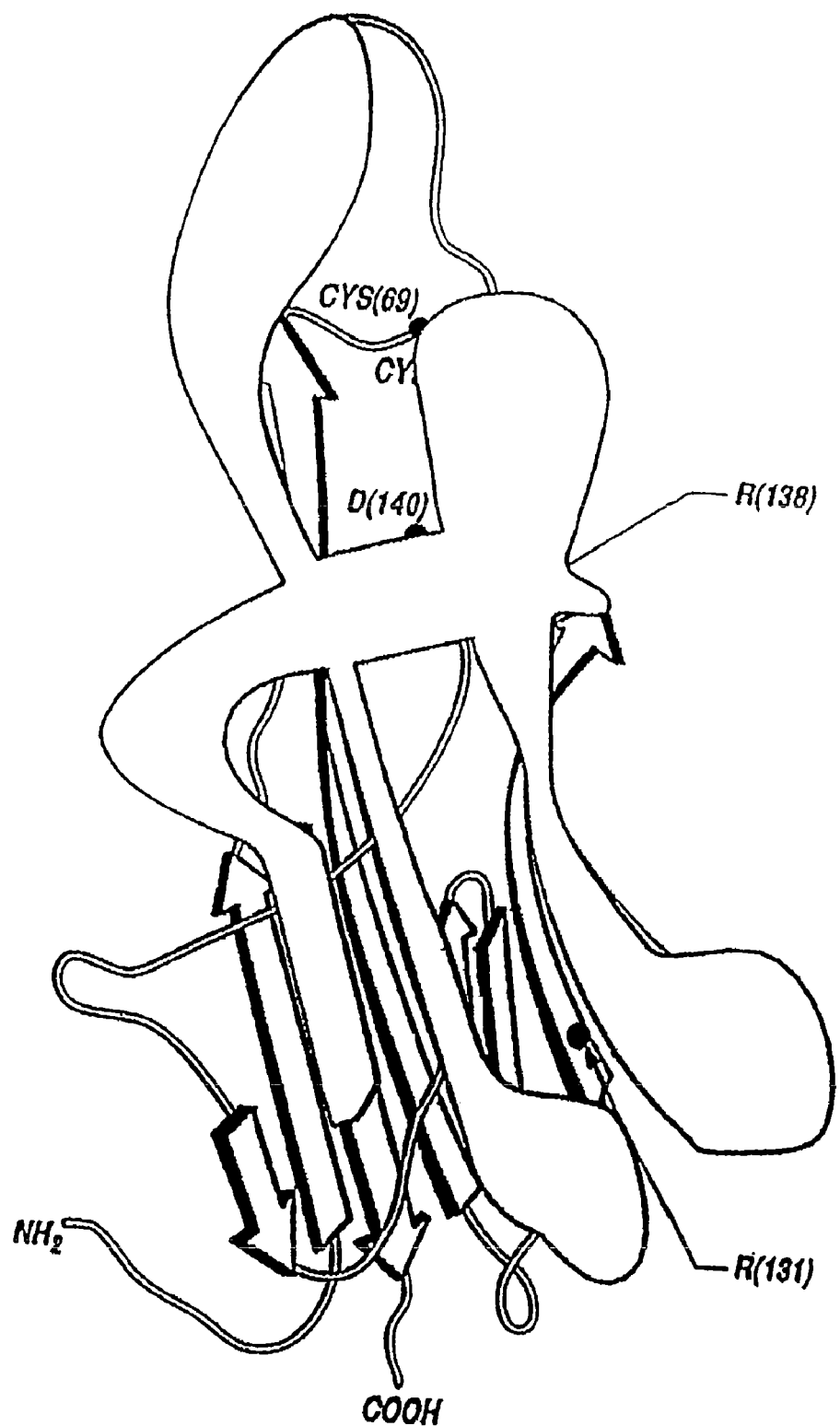
FIG. 30 shows topographically the region of residues 22-40, 69-97, 105-128 and 135-155.
Figure 31:
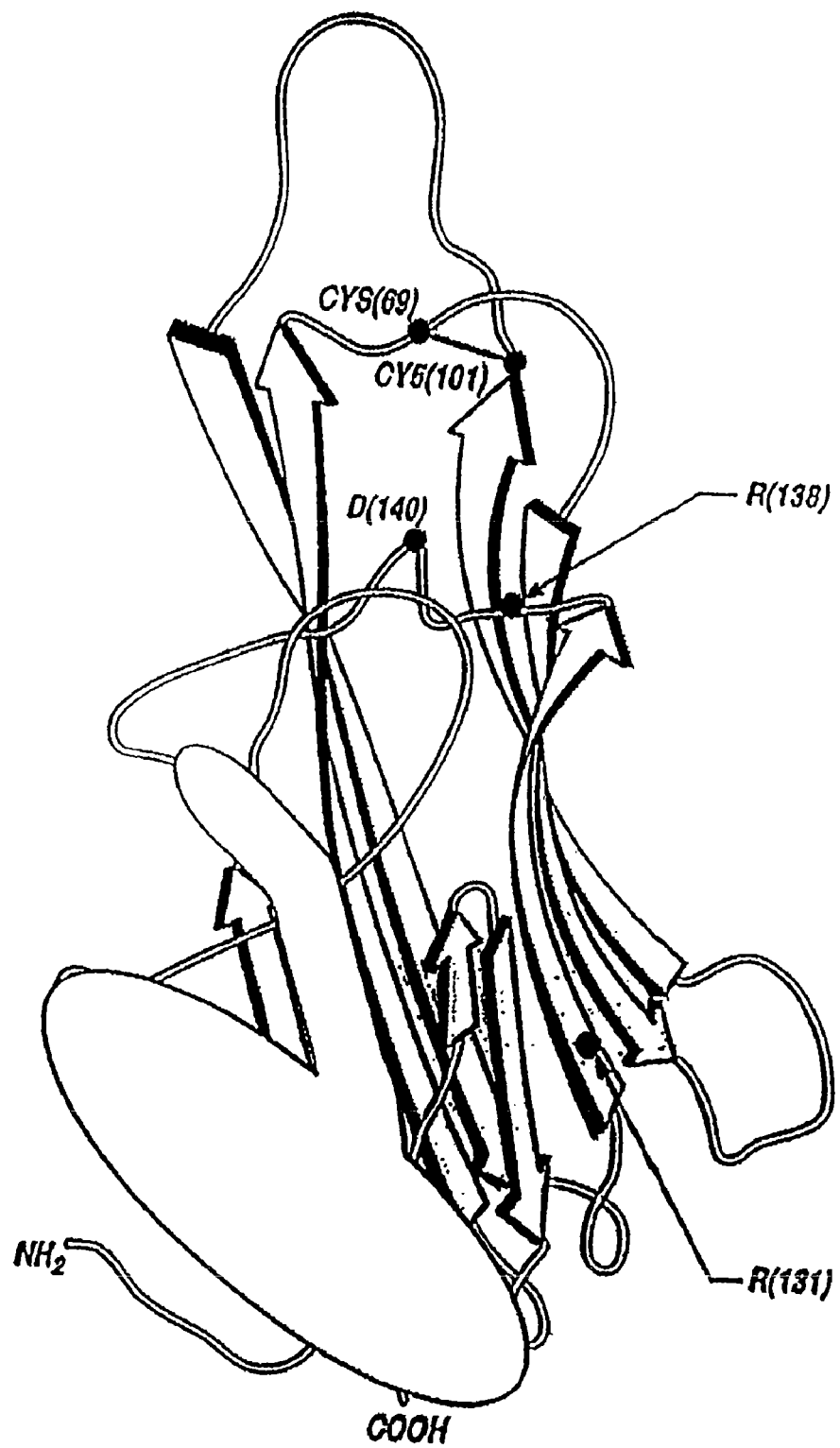
FIG. 31 shows topographically the region of residues 22-31 and 146-157.
Figure 32:
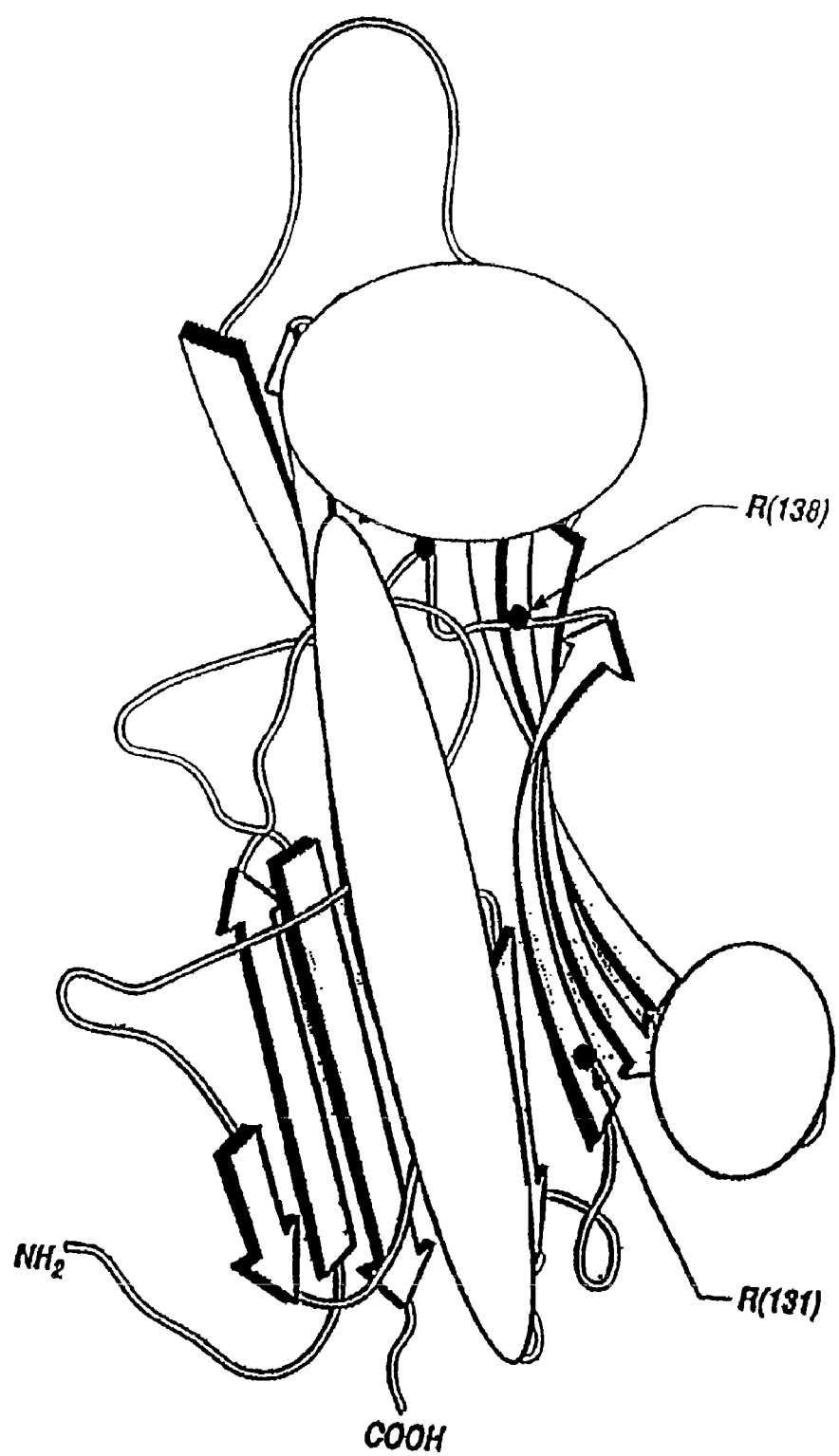
FIG. 32 shows topographically the region of residues 49-98.
Figure 33:
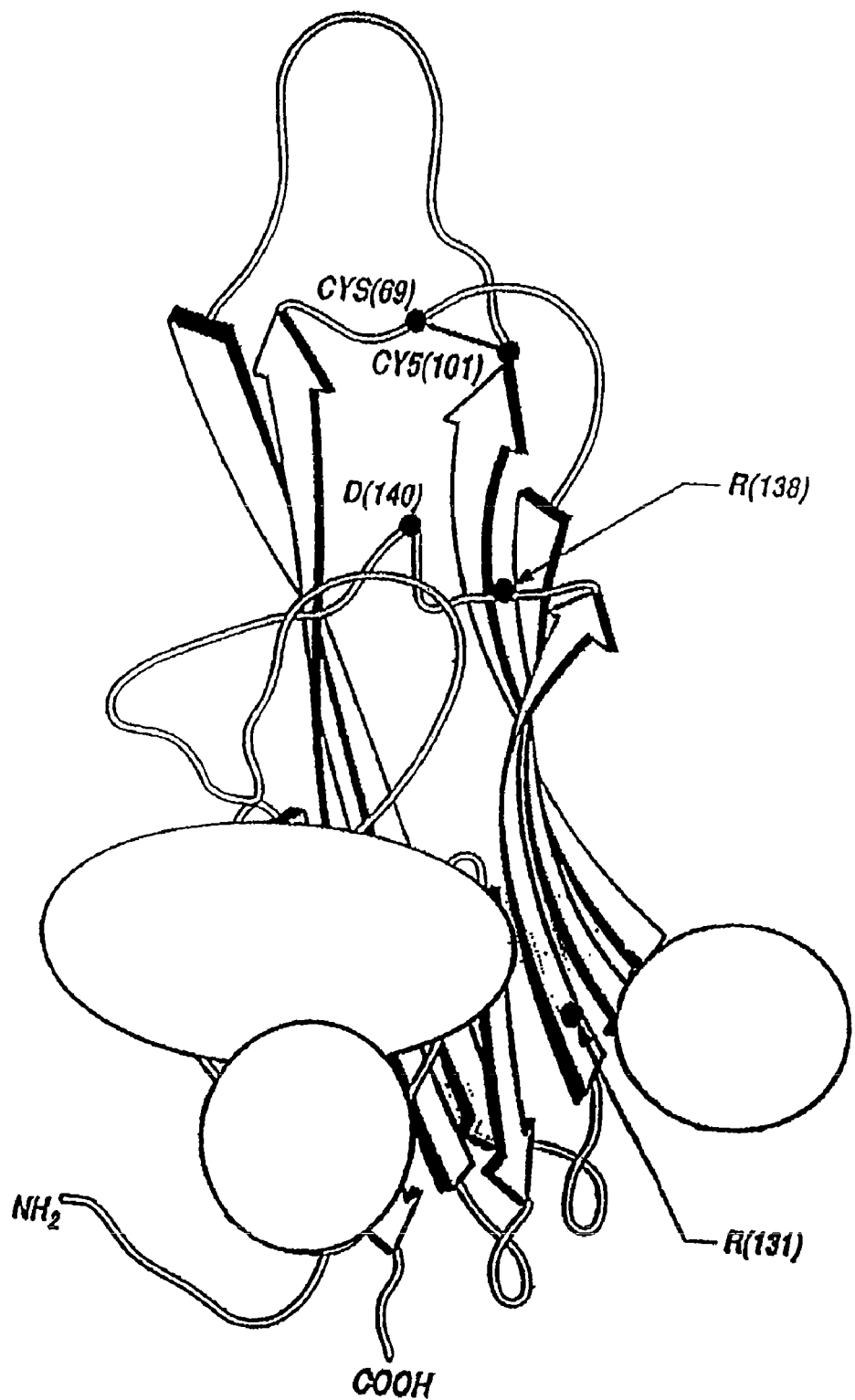
FIG. 33 shows topographically the region of residues 22-40 and 70-87.

Tumour regression studies were carried out as described above in mice carrying WEHI-164 subcutaneous tumours (N=5 animals/group). Tumor size was determined daily during the course of the experiment. The results obtained using MAb 32 are set out in FIG. 22 and show the mean +/−SD % change in tumour area at the completion of treatment (day 2) (■ MAb 32: ▓control MAb: *MAb 47). Differences observed between control MAb-TNF and MAb 32-TNF treated groups are statistically significant in a T-test at the p=<0.01 level.

The results using the univalent FAb' fragments of MAb 32 are shown in FIG. 19. Tumour size was determined daily during the course of the experiment. The results show the mean SD % change in tumour area at the completion of treatment (day 2). Differences between the control MAb-10F and MAb 32-TNF treated groups are statistically significant in a T-test at the P=<0.01 level.

TNF Induced Tumour Regression: Effect of Anti-Peptide 301 SERA

Figure 20:
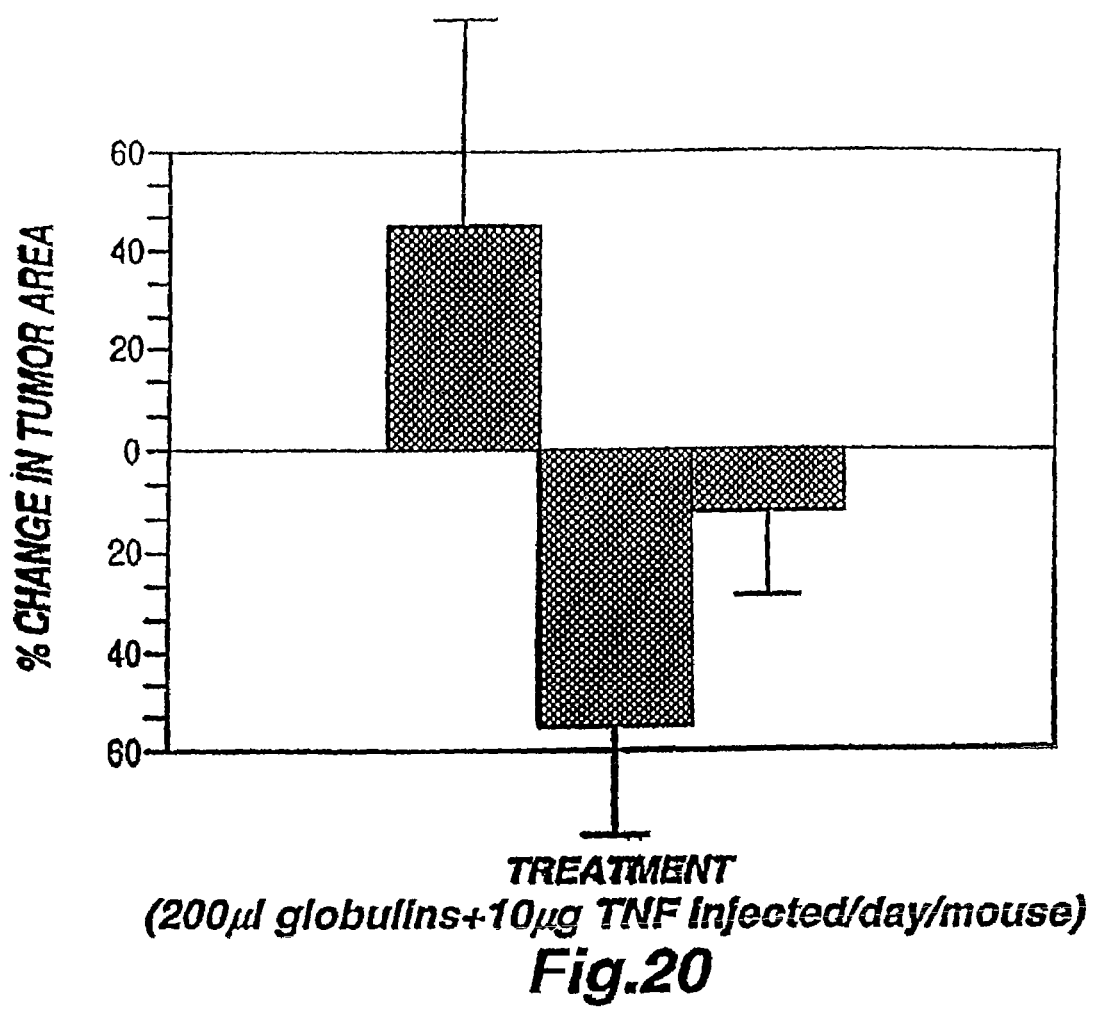
FIG. 20 shows the effect on TNF induced tumour regression by control MAb (■), MAb 32 ( ) and peptide 301 antiserum ( )

FIG. 20 shows the percent change in tumour area in tumour-bearing mice treated for three days with TNF plus control MAb (antibody against bovine growth hormone), TNF plus MAb 32 or TNF plus antiserum (globulin fraction), against peptide 301. In an unpaired T-test the control group is significantly different from both of the test groups (MAb 32, antiserum 301) while the MAb 32 and peptide antiserum 301 groups are not significantly different from each other. (control vs MAb 32, p<0.002; control vs antipeptide 301, p<0.025). Thus antisera raised using a peptide which comprises part of the MAb 32 specificity, also causes TNF enhancement of tumour regression.

As shown in FIG. 8 competition binding studies have shown that the thirteen monoclonal antibodies can be subdivided into two main groups, namely MAbs 1, 21, 47, 54, 37, 32 and 25 and MAbs 11, 12, 53 and 42. Experiments were then conducted to identify the regions on human TNF recognised by these monoclonal antibodies.

Identification of Regions on Human TNF Recognized by Monoclonal Antibodies

Methods

1. Overlapping peptides of 7 and 10 amino acid residues long were synthesized on polypropylene pins according to the method of Geysen et al., 1984, PNAS 81, 3998-4002. The overlap was of 6 and 9 residues respectively and collectively the peptide covered the entire TNF amino acid sequence. The peptides were tested for reactivity with the MAbs by ELISA. MAb5 which had TNF reactivity absorbed from them by prior incubation with whole TNF were also tested for reactivity with the peptides and acted as a negative control.

2. Longer peptides of TNF were synthesized as described below. These peptides were used to raise antisera in sheep using the following protocol. Merino sheep were primed with TNF peptide conjugated to ovalbumin and emulsified in Freunds Complete adjuvant and boosted at 4 weekly intervals with peptide-ovalbumin and sera assayed for the presence of anti-TNF antibody by radioimmunoassay. Of the peptides shown only peptides 275, 301, 305, 306 and 307 elicited sera reacting with whole TNF. The positive sera were then used in competitive binding assays (PACT assays) with the MAbs.

The following peptides were synthesised and are described using the conventional three letter code for each amino acid with the TNF sequence region indicated in brackets.

Peptide 275
H-Ala-Lys-Pro-Trp-Tyr-Glu-Pro-Ile-Tyr-Leu-OH
(111-120)

Peptide 301
H-Val-Arg-Ser-Ser-Ser-Arg-Thr-Pro-Ser-Asp-Lys-Pro-
Val-Ala-His-Val-Val-Ala-OH (1-18)

Peptide 302
H-Leu-Arg-Asp-Asn-Gln-Leu-Val-Val-Pro-Ser-Glu-Gly-
Leu-Tyr-Leu-Ile-OH (43-58)

Peptide 304
H-Leu-Phe-Lys-Gly-Gln-Gly-Cys-Pro-Ser-Thr-His-Val-
Leu-Leu-Thr-His-Thr-Ile-Ser-Arg-Ile-OH (63-83)

Peptide 305
H-Leu-Ser-Ala-Glu-Ile-Asn-Arg-Pro-Asp-Tyr-Leu-Asp-
Phe-Ala-Glu-Ser-Gly-Gln-Val-OH (132-150)

Peptide 306
H-Val-Ala-His-Val-Val-Ala-Asn-Pro-Gln-Ala-Glu-Gly-
Gln-Leu-OH (13-26)

Peptide 307
H-Ala-Glu-Gly-Gln-Leu-Gln-Trp-Leu-Asn-Arg-Arg-Ala-
Asn-Ala-Leu-Leu-Ala-Asn-Gly-OH (22-40)

Peptide 308
H-Gly-Leu-Tyr-Leu-Ile-Tyr-Ser-Gln-Val-Leu-Phe-Lys-
Gly-Gln-Gly-OH (54-68)

Peptide 309
H-His-Val-Leu-Leu-Thr-His-Thr-Ile-Ser-Arg-Ile-Ala-
Val-Ser-Tyr-Gln-Thr-Lys-Val-Asn-Leu-Leu-COOH (73-94)

Peptide 323
H-Thr-Ile-Ser-Arg-Ile-Ala-Val-Ser-Tyr-Gln-Thr-
COOH (79-89)

Peptide 309
H-His-Val-Leu-Leu-Thr-His-Thr-Ile-Ser-Arg-Ile-Ala-Val-Ser-Tyr-Gln-Thr-Lys-Val-Asn-Leu-Leu-COOH (73-94).
Peptide 323
H-Thr-Ile-Ser-Arg-Ile-Ala-Val-Ser-Tyr-Gln-Thr-COOH (79-89).

These peptides were synthesised using the following general protocol.

All peptide were synthesised using the Fmoc-polyamide method of solid phase peptide synthesis (Atherton et al, 1978, J. Chem. Soc. Chem. Commun., 13, 537-539). The solid resin used was PepSyn KA which is a polydimethylacrylamide gel on Kieselguhr support with 4-hydroxymethylphenoxy-acetic acid as the functionalised linker (Atherton et al., 1975, J. Am. Chem. Soc. 97, 6584-6585).

The carboxy terminal amino acid was attached to the solid support by a DCC/DMAP-mediated symmetrical-anhydride esterification.

All Fmoc-groups were removed by piperidine/DMF wash and peptide bonds were formed either via pentafluorophenyl active esters or directly by BOP/NMM/HOBt (Castro's reagent) (Fournier et al, 1989, Int. J. Peptide Protein Res., 33, 133-139) except for certain amino acids as specified in Table 5.

Side chain protection chosen for the amino acids was removed concomittantly during cleavage with the exception of Acm on cysteine which was left on after synthesis.

TABLE 5

| Amino Acid | Protecting Group | Coupling Method |
|---|---|---|
| Arg | Mtr or Pmc | Either |
| Asp | OBut | Either |
| Cys | Acm (permanent) | Either |
| Glu | OBut | Either |
| His | Boc | OPfp only |
| Lys | Boc | Either |
| Ser | But | BOP only |
| Thr | But | BOP only |
| Tyr | But | Either |
| Trp | none | Either |
| Asn | none | OPfp only |
| Gln | none | OPfp only |

Cleavage and Purification

Peptide 301, 302, 305 are cleaved from the resin with 95% TFA and 5% thioanisole (1.5 h) and purified on reverse phase C4 column, (Buffer A-0.1% aqueous TFA, Buffer B 80% CAN 20% A).

Peptide 303, 304 are cleaved from the resin with 95% TFA and 5% water (5-6 h) and purified an reverse phase C4 column. (Buffers as above).

Peptide 306, 308 are cleaved from the resin with 95% TFA and 5% water (1.5 h) and purified on reverse phase C4 column. (Buffers as above).

Peptide 309 Peptide was cleaved from the resin with 95% TFA and 5% thioanisole and purified on reverse phase C4, column. (Buffers as above).

Peptide 307 Peptide was cleaved from the resin with a mixture of 93% TFA, 3.1% Anisole, 2.97% Ethylmethylsulfide and 0.95% Ethanedithiol (3 h) and purified on reverse phase C4 column. (Buffers as above).

Results

Typical results of MAb ELISA using the 7 and 10 mers are shown in FIGS. 21a-c. Together with the results of PACT assays using the sheep anti-peptide sera (shown in Table 6) the following regions of TNF contain the binding sites of the anti-TNF MAbs.

MAb 1: residues 1-18, 58-65, 115-125, 138-149
MAb 11: residues 49-98
MAb 12: residues 22-40, 70-87
MAb 21: residues 1-18, 76-90
MAb 25: residues 12-22, 36-45, 96-105, 132-157
MAb 32: residues 1-26, 117-128, 141-153
MAb 37: residues 22-31, 146-157
MAb 42: residues 22-40, 49-96, 110-127, 136-153
MAb 47: residues 1-18, 106-128
MAb 53: residues 22-40, 69-97, 105-128, 135-155
MAb 54: residues 56-79, 110-127, 136-155

TABLE 6

COMPETITIVE BINDING OF TNF BY ANTI-TNF MONOCLONES IN THE PRESENCE OF ANTI PEPTIDE SERA

| MAB/PEPTIDE SERA | 275 | 301 | 305 | 306 | 307 |
|---|---|---|---|---|---|
| 1 | − | + | − | − | − |
| 11 | − | +/− | − | − | − |

TABLE 6-continued

COMPETITIVE BINDING OF TNF BY ANTI-TNF MONOCLONES
IN THE PRESENCE OF ANTI PEPTIDE SERA

| MAB/PEPTIDE SERA | 275 | 301 | 305 | 306 | 307 |
|---|---|---|---|---|---|
| 12 | − | + | − | − | ++ |
| 21 | − | ++ | − | − | − |
| 25 | − | + | − | − | − |
| 32 | − | ++++ | + | + | − |
| 37 | − | + | +/− | − | + |
| 47 | − | + | − | − | − |
| 53 | − | + | − | − | + |
| 54 | − | + | − | − | − |
| 42 | − | + | + | − | + |

Note 1:
− indicates no competition,
+ indicates slight competition at high concentration of anti-peptide antisera (1/50),
++++ indicates strong competition by anti-peptide sera equal to that of the homologous MAb.
Note 2:
Only peptide which elicited sera recognising whole TNF were used in this assay.

Note 1: − indicates no competition, + indicates slight competition at high concentration of anti-peptide antisera (1/50), ++++ indicates strong competition by anti-peptide sera equal to that of the homologous MAb.

As will be understood by persons skilled in this field the ligands of the present invention can be used in assays of biological fluids for detecting the presence of and quantifying the concentration of TNF in a sample. One means by which this may be achieved is by using the ligands of the present invention in conventional ELISAs. Set out below is an example of such an assay.

TNF ELISA REAGENTS

CARBONATE COATING BUFFER, pH 9.6

| | | |
|---|---|---|
| $Na_2CO_3$ | 1.6 g | Add 800 mL $dH_2O$, pH to 9.6 |
| $NaHCO_3$ | 2.9 g | then make to 1 L with $dH_2O$ |

BLOCKING BUFFER

| | | |
|---|---|---|
| BSA | 1 g | Add BSA to PBS and allow |
| PBS | 100 mL | to dissolve fully before using. Store at 4° C. |

WASH BUFFER (0.05% TWEEN/PBS)

| | | |
|---|---|---|
| TWEEN 20 | 0.5 g | Add TWEEN to PBS and mix |
| PBS | 1 L | thoroughly before use |

CITRATE BUFFER

| | | |
|---|---|---|
| Citric Acid. $1H_2O$ | 2.1 g in 50 mL $dH_2O$ | Add solutions together and adjust pH to 4.0-4.2 |
| TriSodium Citrate $2H_2O$ | 1.47 g in .50 mL $dH_2O$ | |

NB:
All incubations can be carried out at 4° C. overnight OR at room temperature for 2 hrs OR at 37° C. for 1 hr.

Method
Coat ELISA plates with equal proportions of MAb1, MAb32 and MAb54 to human TNF in carbonate coating buffer. The total immunoglobulin concentration should be 20 µg/mL and 100 µL is added to each well. Cover plates and incubate.
Wash plates 3× with PBS/TWEEN.
Incubate plates with 250 µL/well blocking buffer
Wash plates 3× with PBS/TWEEN.
Add 100 µL sample or TNF standards, diluted in blocking buffer where required, to plates, then cover and incubate.
Wash plates 3× with PBS/TWEEN.
Add 100 µL biotinylated antibody mix (equal proportions of biotinylated monoclonal antibodies 11 & 42 to human TNF) at a final concentration of 100 µg/mL in blocking buffer to each well, cover and incubate.
Wash plates 3× with PBS/TWEEN.
Add 100 µL/well streptavidin-peroxidase (Amersham product no. RPN 1231) at 1/2,000 in blocking buffer, then cover and incubate.
Wash plates 3× with PBS/TWEEN.
Add 100 µL/well biotinylated anti-stretpavidin monoclonal antibody (Jackson Immunoresearch) at 1/40,000 in blocking buffer, cover and incubate.
Wash plates 3× with PBS/TWEEN.
Add 100 µL/well streptavidin-peroxidase at 1/2,000 in blocking buffer, cover and incubate.
Wash plates 3× with PBS/TWEEN.
Add 100 µL/well peroxidase substrate (ABTS) at 1 mg/mL in citrate buffer containing 0.3 µL/ml $H_2O_2$ and leave to incubate at room temperature for up to 1 hour.
NB: Substrate solution should be prepared immediately prior to use.
Read absorbance at 405nm, and compare sample readings with TNF standard curve to determine TNF levels.

BIOTINYLATION OF IgG

| | | |
|---|---|---|
| 50 mM BICARBONATE BUFFER, pH 8.5 | | |
| $Na_2CO_3$ | 1.6 g | In 1 L $dH2O$, adjust pH |
| $NaHCO_3$ | 2.9 g | with HCl |
| 0.1 PHOSPHATE BUFFER, pH 7.0 | | |

Figure 34:
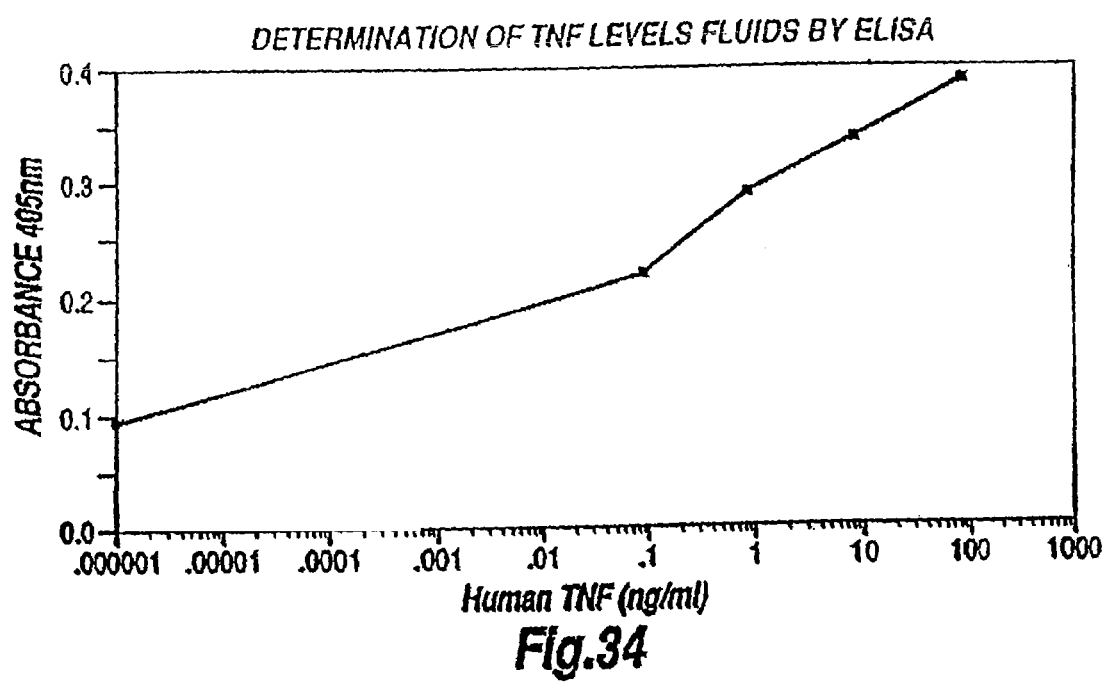
FIG. 34 shows results of an ELISA using samples containing varying levels of TNF.

Method
Prepare immunoglobulins by purifying on a protein A column, then freeze-drying.
Reconstitute the immunoglobulins with 50 mM bicarbonate buffer to a concentration of 20 mg/mL in a clean glass test tube.
Add 0.4 mg biotin per 20 mg Ig directly to the tube.
Place the test tube on ice and incubate for 2 hours.
Remove the unreacted biotin by centrifuging at 1000 g for 15-30 minutes in a Centricon-30 microconcentrator. Dilute the sample in 0.1M phosphate buffer and repeat the centrifugration twice.
Make the sample up to the original volume with phosphate buffer, add 0.1% $NaN_3$ and store at 4° C. until used.
The results obtained in such an assay using samples containing known amounts of TNF is shown in FIG. 34.

As mentioned above the specific mouse monoclonal antibodies disclosed in this application can be humanised if required. A number of methods of obtaining humanized antibodies are set out in PCT/GB92/01755 (WO93/06213). A humanised version of MAb32 designated VHP3-VλA2 was produced by the method disclosed in PCT/GB92/01755. Briefly, this antibody was produced as follows:

1. Cloning and Display of the V Genes of MAb 32 on Phage
Cloning and Display of the V-genes of MAb32:
The genes of the mouse MAb32 antibody (IgG2b, Kappa) were rescued by PCR essentially as described (Clackson et al, 1991, "PCR: A Practical Approach" eds. M. J. McPherson et al., IRL Press, Oxford, pp 187-214) using the primers VH1BACk and VH1FOR2 for the VH gene and Vk2BACK and VK4FOR for the VL gene and the polymerase chain reaction (PCR, R. K. Saiki et al., 1985, Science 230, p1350). The mouse VH and Vk genes were assembled for expression as scFv fragments by PCR assembly (Clackson et al., supra) amplified with VH1BACKSfi and VFFOR4NOT and ligated into phagemid pHEN1 (H. R. Hoogenboom et al., 1991 Nucl. Acids. Res. 19 pp4133-4137) as a SfiI-NotI cut restriction fragment, and electroporated into *E. coli* HB2151 cells. Of 96 clones analysed by ELISA (see below), 9 secreted TNF-binding soluble scFv fragments. Sequencing revealed in all clones a mouse VH of family IIB and a mouse Vk of family VI (E. A. Kabat et al., 1991 Sequences of Proteins of Immunological Interest, US Public Health Services). Nucleotide mutations which were probably introduced by the PCR were detected by comparing the 9 sequences, and a clone with consensus sequence and binding activity (scFv-MAb32) chosen for further cloning experiments.

Recloning of the MAb32 V-genes for soluble expression:

The murine V-genes were recloned for soluble expression of heavy (Fd, VHCH1) or light chain, by linking the mouse V-genes to the human CH1 (of the mu-isotype) or human Ck gene respectively by splice overlap extension. The mouse Vk gene was amplified from scFv-MAb32 DNA with oligonucleotides MOJK1FORNX (binds in joining region of V-gene and MVKBASFI (binds in 5' region and adds SfiI restriction site); the human Ck was obtained by PCR from a mouse-human chimaeric light chain gene (of NQ10.12.5, described in Hoogenboom et al., 1991 supra), with oligonucleotides MOVK-HUCK-BACK (binds in 5' of human Ck and is partially complementary with mouse Jk 1 region) and HUCKNOT16NOMYC (sits in 3' end of human Ck, retains the terminal cysteine, and tags on a NotI restriction site) as in Clackson et al., 1991 using a two fragment assembly. For linkage of the DNA fragments, the two PCR fragments were mixed and amplified with MVKBASFI and HUCKNOT16NOMYC. The chimaeric VkCk gene was subsequently cloned as a SfiI-NotI fragment in pUC19 derivative containing the pelB signal peptide sequence and appropriate cloning sites for soluble expression of the light chain (pUC19-pe1B-myc). Similarly, the mouse VH gene (amplified from scFv-MAb32 with LMB3 and VH1FOR-2) was combined by splicing by overlap extension PCR with the human u-CH1 domain (amplified from human IgM-derived cDNA (Marks et al., 1991, supra; WO 92/01047) with Mo-VH-Ku-CH1 and HCM1FONO, and cloned as SfiI-NotI fragment into a pUC19-pe1B-myc for soluble expression of a tagged chain.

Display of the MAb32 Antibody on Phage:

The chimaeric light chain was displayed on phage fd by reamplification of the mouse/human chimaeric chain with HUCKCYSNOT and MVKBAAPA and cloning into fd-tet-DOG1 as an ApaLI-NotI fragment. Cells harbouring a plasmid with the heavy Fd chain gene were grown in 2×TY containing AMP-GLU (1%) to logarithmic phase (OD600 of 0.5) and infected with a 20-fold excess of light-chain displaying phage. After 45 min at 37° C. without shaking and 45 min at 37° C. with shaking in the 2×TY, ampicillin (100 µg/ml). Glucose 1% medium, a sample was diluted into 50-fold volume of prewarmed (37° C.) 2× TY, ampicillin (100 µg/ml) and tetracyclin (15 µg/ml), grown for 1 hr at 37° C. and then overnight at 30° C. (shaking). Phage particles collected from the supernatant of such culture displayed TNF-binding Fab fragments anchored through the light chain on their surface.

Similarly, the reversed configuration was made. The heavy chain VHCH1 fragment was cloned into fd-tet-DOG1 (after amplification of the Fd chain gene from the mouse/human chimeric construct with VH1BACKAPA and HCM1FONO), and phage used to infect cells capable of producing soluble light chain. Phage particles collected from the supernatant of such culture displayed TNF-binding Fab fragments anchored through the heavy chain VHCH1 fragment on their surface.

Properties of MAb 32 Fragments Displayed on Phage:

The V-genes of the murine antibody MAb32 were cloned by amplifying the hybridoma V-genes, cloning the VH and Vk genes as scFv fragments in phagemid pHEN1 as above. Antibody scFv fragments which bind to TNF were identified by ELISA. The mouse VH gene was recloned in pUC19-pe1B-myc for soluble expression as a mouse VH linked to human mu-CH1, while the light chain was recloned with the human Ck domain in vector fd-tet-DOG1 as a fusion with g3p. When cells harbouring the heavy chain construct were infected with the fd-phage carrying the light chain, phage particles emerged which carried light chain-g3p associated with the fd heavy chain. Indeed, binding to TNF and the 301 peptide was retained, as judged by ELISA with phage displaying the mouse-human chimaeric Fab fragment. In the phage ELISA, the background signal of phage carrying the light chain only was a lightly higher than wild-type fd-tet-DOG1 phage, but always lower than the signal obtained with Fab-displaying phage. Similarly, TNF binding phage was made with the heavy chain VHCH1 fragment anchored on phage, and the light chain provided as a soluble fragment. Hence, MAb32 is functional in the dual combinatorial format in both display orientations.

2. Chain Shuffling by Epitope Imprinted Selection (EIS) Construction of One Chain-Libraries:

Kappa, lambda light chain and Mu-specific cDNA was made from the mRNA prepared from the peripheral blood lymphocytes from two healthy donors essentially as in Marks et al., 1991, supra. The first-strand cDNA synthesis was performed with oligonucleotides HCM1FO, HUCLCYS and HUCKCYS for Mu-specific, lambda and kappa libraries respectively. The VH-CH 1 repertoire was amplified from this cDNA with oligonucleotides HCM1FO and six family specific VHBACK primers (as in Marks et al., 1991, supra), reamplified with a NotI-tagged forward primer (HCM1FONO) and ApaLI tagged VHBACK primers (6 primers HuVH1BAAPA to HuVH6BAAPA). Similarly, the light chain repertoires were amplified with HUCLCYS or HUCKCYS forward primers and HUVλ1BACK to HuVλ6BACK or HuVk1BACK to HuVk6BACK back primers described in Marks et al., 1991, supra and PCT/GB91/01134 (WO 92/01047). In each case described in this section the lambda and kappa chain variable repertoires were amplified separately. The amplified repertoires were reamplified with ApaLI and NotI tagged versions of these oligonucleotides (13 back primers HuVλ1BAAPA to Huλ6BAAPA or HuVk1BAAPA to HuVkBAAPA and two forward primers HuCLCYSNOT and HuCKCYSNOT, respectively). All three repertoires were cloned into vector fd-tet-DOG1 as ApaLI-NotI fragments, and electroporated into *E. coli* MC1061 cells, to obtain libraries of $1.0 \times 10^7$ clones for VλCA, $1.4 \times 10^6$ clones for VkCk, and $5 \times 10^6$ clones for IgM-derived VHCH1. The presence of insert was checked and the frequency of inserts in the library found to be higher than 95% in all three cases.

Selecting a Human VL Using the Mouse VH Domain as Docking Chain

In a first chain shuffling experiment, the mouse VH (linked to the human CH1 domain), expressed from pUC19-pe1B-myc, was paired as Fab fragment with a library of $10^7$ different human VλCλ domains. Phage displaying the antibody fragments were subjected to rounds of panning on TNF-coated tubes. By following the titre of the eluted phage, the extent of selection was monitored. After 4 rounds (with a 100-fold increase in the titre of eluted phage), 24 out of 28 individual clones were found to be binding to TNF in an ELISA with phage expressing Fab fragments (all with the mouse VH-human CH1). Phage only displaying the selected human VλCλ domains gave a background similar to phage displaying only the chimaeric mouse Vk-human Ck. Sixteen clones taken after the first round of selection were found to be negative.

Only three different BstN1 fingerprints were found amongst the 24 binders, with one pattern dominating (21/24). Light chains VλA2, VλC4 and VλD1 were found with frequencies of 21/24, 2/24 and 1/24 respectively. Sequencing revealed that all three light chains are derived from the same germline gene, a human Vλ1-1-1. Clone VλC4 has 1, clone VλD1 has 2 and clone VλA2 7 amino-acid residue differences from the germline. However, clone VλA2 uses a framework-1 region which more closely resembled the germline sequence of a related Vλ1, humv1117, and therefore may be the result of a cross-over. The germline character of the clones was also noted in the CDR3 sequence, with minimal variation in sequence and no length variation between the three clones. Apparently, only a very limited number of genes with very similar sequences fix the stringent requirements (being compatible with the mouse VH and forming an antigen-binding pair).

Selecting a Human VH Using the Selected Human VL Domains as Docking Chains

Three selected Vλ genes were recloned in pUC19-pe1B-myc for soluble expression VλCλ chains. E. coli cells harbouring the three light chain plasmids were mixed, infected with a phage library of human VHCH1 genes, expressed from the fd-tet-DOC1 library described earlier and the library subjected to rounds of panning on TNF-coated Immuno tubes. Clones were picked after 5 rounds, when the titre of eluted phage increased 100-fold. Fifteen out of 20 clones analysed by BstNI fingerprint of the DNA insert used one of two patterns (with approximately the same frequency). The 15 clones when combining their heavy chain VHCH1 fragments with the VλA2 light chain gave stronger phase ELISA signals than when combined with the VλC4 or VλD1 light chain. Background signals obtained with phage displaying the heavy chain VHCH1 fragment only were similar to the signal of the murine VH-human CH 1.

Sequencing revealed that the two patterns could be assigned to three unique human VH sequences (clones VHP1/2/3, with clone VHP1 having a BstNI fingerprint which is nearly identical to that of clone VHP2). Like the selected light chain genes, the selected heavy chain genes are derived from the same germline VH gene (germline DP-51 from the VH3 family, Tomlinson et al., J. Mol. Biol. 227, pp776-798 1992), with minimal residue differences. The selected human V-genes were aligned to their closest germline homologue; identical residues in the selected genes are represented by hyphens. Framework 4 of the $V_H$ genes was truncated at 4th residue. Clone VHP1 was most likely a cross-over between DP-51 and a related germline, DP-47. All three selected VH-genes had relatively short CDR3 loops (8, 9 and 10 residues), but shared little homology in this sequence.

Specificity of Binding of the Selected V-gene Pairs:

A specificity ELISA with MAb32 and soluble ScFv fragments on a number of antigens showed that MAb32, its ScFv-derivative and three of the humanised TNF-binders (as ScFv-fragments) bind specifically to TNF. No significant binding was obtained to ELISA plates coated with keyhole limpet haemocyanin, ovalbumin, cytochrome c. bovine serum albumin, human thyroglobulin, or 2-phenyloxazol-5-one-BSA or to plastic only. Fully humanized clones were obtained which bound to both peptide 301 and TNF.

In addition, to show that the human scFv fragments compete with the original antibody for binding to TNF, the binding of the scFv constructs in a competition ELISA with the Fab fragment derived by proteolytic cleavage of MAb32 was analysed. Single chain Fv fragments were incubated on a TNF-coated surface with increasing amounts of the Fab fragment and the amount of bound scFv detected in ELISA. Each of the scFv fragments competed with the FabMAb32 for binding to TNF, including both the original scFv-MAb32 and the humanised scFv fragments.

Thus the fine specificity of MAb32 for peptide 301 of TNF was retained through the humanisation process.

Affinity of Binding of the Selected V Gene Pairs:

MAb32 and purified, monomeric forms of the recombinant mouse scFv-MAb32 and the human scFv antibodies VHP1-VλA2. VHP2-VλA2 and VHP3-VλA2, were subjected to competition ELISA for the determination of the relative affinity for TNF. Antibodies were incubated on a TNF-coated surface in the presence of increasing amounts of soluble TNF. All the clones showed a roughly similar decrease in the ELISA signal over the same range of increasing TNF concentrations (with an IC50 in the 10 nM to 100 nM range).

MAb32 and VHP3VλA2 fragments were also analysed for binding properties using the Pharmacia BIAcore. TNF was indirectly immobilised on the surface and the binding of antibody monitored. On the TNF surface, the Fab fragment from MAb32 by proteolytic cleavage and the scFv MAb32 showed very similar fast off rates (approximately $10^{-2}s^{-1}$). The human VHP3-VλA2 antibody has an off rate in the same range as the original scFv-MAb32. On rates for antibody protein interactions were in the range seen for the interaction between other proteins and their receptors, and cover a 100 fold range between $10^4$ and $10^6$ $M^{-1}S^{-1}$ (Mason D. W. and Williams A. F., 1986, Kinetics of Antibody Reactions and the Analysis Of Cell Surface Antigens, Blackwell, Oxford; Pecht, I., 1992 in Sela, M. (ed), Dynamic Aspects of Antibody Function, Academic Press Inc., New York, Vol. 6 pp 1-68). Assuming the on rates of the antibody TNF interactions are typical of antibody protein interactions, the off rate derived by the BIACore analysis is consistent with the affinity indicated by the competition ELISA (Kd≅$10^{-7}$ to $10^{-8}$M).

Thus, these determinations are consistent with scFvMAb32 and the humanised scFv clone VHP3-VλA2 having a similar affinity and thus with the retention of affinity, as well as specificity, through epitope imprinted selection.

Conclusion

We have shown that a mouse antibody can be rebuilt into a human antibody with the same specificity by the process of epitope imprinted selection (EIS).

A library of human light chains were shuffled with a mouse VH domain, binding combinations selected and then used in a second shuffle as "docking domains" for a library of human VH genes. Completely human antibodies were isolated from such "genuine" human library. The antibodies were shown to bind retain binding specificity. Alternatively, the mouse VL was used as docking chain for selecting human VH partners. Such VH domains can be used to find human VL genes, or alternatively, can be combined with human VL domains selected with the mouse VH domain. Indeed, binding activity was obtained by combining two independently selected V-genes, pointing towards potential additivity of the EIS procedure.

The EIS approach may serve to humanise antibodies more rapidly than by CDR-grafting (Riechmann et al., 1988, supra), as this method requires very often a detailed knowledge of the 3-D structure of the antibody. However, the EIS method can be extended to for example antibody repertoires obtained by phage selection from immunised rodents. Following immunisation with antigen, a repertoire of V-genes with high affinity and specificity may be selected and then used in an epitope imprinted selection (see example 4) to generate a range of human antibodies of high affinity and enriched for the desired specificity.

Enhancement of TNF-Induced Tumour Regression by Antibody VHP3-VλA2, The Human Equivalent of MAb 32

BALB/c mice were inoculated with WEHI-164 tumour cells as described above. After development of subcutaneous tumours the mice were treated daily with TNF (1 or 10 µg) alone or in combination with purified P3A2 (50µ) by intraperitoneal injection. Tumour size was measured throughout the course of the treatment period.

Results are shown in FIG. 35.

VHP3-VλA2 enhanced the anti-tumour activity of TNF at both the 1 and 10 µg levels.

CONCLUSIONS

Mapping of the regions recognized by each of the MAbs has indicated that MAbs in group I (MAbs 1, 21, 47, 54, 37, 32 and 25) as shown on the schematic diagram bind TNF in the region of residues 1-18 with the exception of MAbs 37 and 54, while MAbs in group II of the schematic diagram (MAbs 11, 12, 53 and 42) bind TNF in the region of residues 70-96 which encompasses a so-called pallendromic loop on the TNF 3-D structure. MAbs which inhibit the induction of endothelial cell procoagulant activity (MAbs 1, 32, 42, 47, 54 and 53) all bind in the region of residues 108-128 which again contains a loop structure in the 3-D model and may indicate that this region interacts with TNF receptors which are found on endothelial cells but not tumour cells. MAb 32 which potentiates the in vivo tumour regression and anti-viral activity of TNF is the only antibody which binds all the loop regions associated with residues 1-26, 117-128 and 141-153 and hence binding of these regions is crucial for enhanced TNF bioactivity with concommittant reduction of toxicity for normal cells.

As is apparent from Table 2 MAb 1, 47 and 54 have the same effect on the bioactivity of TNF. From the results presented above it is noted that these three monoclonals bind to similar regions of the TNF molecule. Accordingly, it is believed that a ligand which binds to TNF in at least two regions selected from the group consisting predominately of the region of residues 1-20, the region of residues 56-77, the region of residues 108-128 and the region of residues 130-149 will effect the bioactivity of TNF in a manner similar to that of MAbs 1, 47 and 54. Similarly, it is believed that a ligand which binds to TNF predominately in the regions of residues 1-20 and 76-90 will have the same effect on the bioactivity of TNF as MAb 21. A ligand which binds to TNF predominately in the regions of residues 22-40 and 69-97 will have the same effect on bioactivity of TNF as MAb 12. A ligand which binds to TNF predominately in the regions of residues 1-30, 117-128, and 141-153 would be expected to have the same effect on the bioactivity of TNF as MAb 32 and a ligand which binds to TNF predominately in the regions of residues 22-40, 49-97, 110-127 and 136-153 would be expected to have the same effect on the bioactivity of TNF as MAb 42. A ligand which binds to TNF predominately in the regions of residues 22-31 and 146-157 would be expected to have the same effect on the bioactivity of TNF as MAb 37 and a ligand which binds to TNF predominately in the regions of residues 22-40, 69-97, 105-180 and 135-155 would be expected to have the same effect on the bioactivity of TNF as MAb 53.

The present inventors have quite clearly shown that the bioactivity of TNF can be altered by the binding of a ligand to the TNF, and that the effect on the bioactivity is a function of the specificity of the ligand. For example, the binding of MAb 32 to TNF in the regions of residues 1-26, 117-128 and 141-153 results in the induction of endothelial procoagulant activity of the TNF and binding of TNF to receptors on endothelial cells being inhibited; the induction of tumour fibrin deposition and tumour regression activities of the TNF being enhanced; the cytotoxicity being unaffected and the tumour receptor binding activities of the TNF being unaffected or enhanced. It is believed that this effect on the bioactivity of the TNF may be due to the prevention of the binding of the epitope of the TNF recognised by MAb 32 to naturally occurring biologically active ligands. Accordingly, it is believed that a similar effect to that produced by MAb 32 could also be produced by a ligand which binds to a region of TNF in a manner such that the epitope recognised by MAb32 is prevented from binding to naturally occurring biologically active ligands. This prevention of binding may be due to steric hindrance or other mechanisms.

Accordingly, it is intended that the prevention of the binding of epitopes recognised by the various monoclonal antibodies described herein to naturally occurring biologically active ligands is within the scope of the present invention.

What is claimed as new and desired to be protected by Letters Patent of the United States is:

1. A cell line producing an antibody or fragment thereof, wherein the antibody or fragment thereof specifically binds to mature human TNF-α, wherein when the antibody or fragment thereof binds mature human TNF-α, the induction of endothelial procoagulant activity is inhibited; and wherein the antibody or fragment thereof competitively inhibits sheep anti-sera raised against a TNF-α peptide for specific binding to mature human TNF-α, wherein the TNF-α peptide is a peptide consisting of residues Val$_1$-Arg$_2$-Ser$_3$-Ser$_4$-Ser$_5$-Arg$_6$-Thr$_7$-Pro$_8$-Ser$_9$-Asp$_{10}$-Lys$_{11}$-Pro$_{12}$-Val$_{13}$-Ala$_{14}$-His$_{15}$-Val$_{16}$-Val$_{17}$-Ala$_{18}$ (peptide 301) of mature human TNF;

wherein the antibody or fragment thereof competitively inhibits Mab 25 (ECACC Accession No. 89121401) for specific binding to mature human TNF-α; and wherein the cell line has been isolated.

2. The cell line according to claim 1, wherein the antibody is a monoclonal antibody.

3. The cell line according to claim 1, wherein the antibody or fragment thereof inhibits tumor receptor binding to TNF-α.

4. The cell line according to claim 1, wherein the antibody or fragment thereof has no effect on tumor receptor binding to TNF-α.

5. The cell line according to claim 3, wherein the antibody or fragment thereof inhibits cytotoxicity.

6. The cell line according to claim 1, wherein the antibody or fragment thereof inhibits cytotoxicity.

7. The cell line according to claim 6, wherein the antibody or fragment thereof inhibits tumor regression.

8. The cell line according to claim 5, wherein the antibody or fragment thereof inhibits tumor regression.

9. The cell line according to claim 3, wherein the antibody or fragment thereof inhibits tumor regression.

10. The cell line according to claim 1, wherein the antibody or fragment thereof inhibits tumor regression.

11. The cell line according to claim 1, wherein the antibody or fragment thereof has no effect on tumor regression.

12. The cell line according to claim 1, where comparative binding specificity between the antibody or fragment thereof and the sheep anti-sera is determined by antibody-anti-sera competition assays in the presence of mature human TNF-α.

13. The cell line according to claim 12, wherein in the antibody-anti-sera competition assays the antibody is immobilized.

14. The cell line according to claim 12, wherein in the antibody-anti-sera competition assays the TNF-α is immobilized.

15. The cell line according to claim 12, wherein the antibody or fragment thereof inhibits tumor receptor binding to TNF-α.

16. The cell line according to claim 12, wherein the antibody or fragment thereof has no effect on tumor receptor binding to TNF-α.

17. The cell line according to claim 12, wherein the antibody or fragment thereof inhibits cytotoxicity.

18. The cell line according to claim 1, wherein the antibody or fragment thereof has no effect on cytotoxicity.

19. The cell line according to claim 12, wherein the antibody or fragment thereof inhibits tumor regression.

20. The cell line according to claim 1, wherein the antibody or fragment thereof does not competitively inhibit sheep anti-sera raised against an additional TNF-α peptide for specific binding to mature human TNF-α,
wherein the additional TNF-α peptide is a peptide consisting of residues $Ala_{111}$-$Lys_{112}$-$Pro_{113}$-$Trp_{114}$-$Tyr_{115}$-$Glu_{116}$-$Pro_{117}$-$Ile_{118}$-$Tyr_{119}$-$Leu_{120}$ (peptide 275) of mature human TNF-α.

21. The cell line according to claim 1, wherein the antibody or fragment thereof does not competitively inhibit sheep anti-sera raised against an additional TNF-α peptide for specific binding to mature human TNF-α,
wherein the TNF-α peptide is a peptide consisting of residues $Leu_{132}$-$Ser_{133}$-$Ala_{134}$-$Glu_{135}$-$Ile_{136}$-$Asn_{137}$-$Arg_{138}$-$Pro_{139}$-$Asp_{140}$-$Tyr_{141}$-$Leu_{142}$-$Asp_{143}$-$Phe_{144}$-$Ala_{145}$-$Glu_{146}$-$Ser_{147}$-$Gly_{148}$-$Gln_{149}$-$Val_{150}$ (peptide 305) of mature human TNF-α.

22. The cell line according to claim 1, wherein the antibody or fragment thereof does not competitively inhibit sheep anti-sera raised against an additional TNF-α peptide for specific binding to mature human TNF-α,
wherein the additional TNF-α peptide is a peptide consisting of residues $Val_{13}$-$Ala_{14}$-$His_{15}$-$Val_{16}$-$Val_{17}$-$Ala_{18}$-$Asn_{19}$-$Pro_{20}$-$Gln_{21}$-$Ala_{22}$-$Glu_{23}$-$Gly_{24}$-$Gln_{25}$-$Leu_{26}$ (peptide 306) of mature human TNF-α.

23. The cell line according to claim 1, wherein the antibody or fragment thereof does not competitively inhibit sheep anti-sera raised against an additional TNF-α peptide for specific binding to mature human TNF-α,
wherein the additional TNF-α peptide is a peptide consisting of residues $Ala_{22}$-$Glu_{23}$-$Gly_{24}$-$Gln_{25}$-$Leu_{26}$-$Gln_{27}$-$Trp_{28}$-$Leu_{29}$-$Asn_{30}$-$Arg_{31}$-$Arg_{32}$-$Ala_{33}$-$Asn_{34}$-$Ala_{35}$-$Leu_{36}$-$Leu_{37}$-$Ala_{38}$-$Asn_{39}$-$Gly_{40}$ (peptide 307) of mature human TNF-α.

24. The cell line according to any one of claims 1-23, wherein the antibody is a humanized antibody.

25. A composition comprising a cell line producing an antibody or fragment thereof that specifically binds to mature human TNF-α,
wherein when the antibody or fragment thereof binds mature human TNF-α, the induction of endothelial procoagulant activity is inhibited; and
wherein the antibody or fragment thereof competitively inhibits sheep anti-sera raised against a TNF-α peptide for specific binding to mature human TNF-α,
wherein the TNF-α peptide is a peptide consisting of residues $Val_1$-$Arg_2$-$Ser_3$-$Ser_4$-$Ser_5$-$Arg_6$-$Thr_7$-$Pro_8$-$Ser_9$-$Asp_{10}$-$Lys_{11}$-$Pro_{12}$-$Val_{13}$-$Ala_{14}$-$His_{15}$-$Val_{16}$-$Val_{17}$-$Ala_{18}$ (peptide 301) of mature human TNF;
wherein the antibody or fragment thereof competitively inhibits Mab 25 (ECACC Accession No. 89121401) for specific binding to mature human TNF-α; and
wherein the cell line has been isolated.

26. A cell line producing an antibody or fragment thereof that specifically binds to mature human TNF-α,
wherein the antibody or fragment thereof competitively inhibits sheep anti-sera raised against a TNF-α peptide for specific binding to mature human TNF-α,
wherein the TNF-α peptide is a peptide consisting of residues $Val_1$-$Arg_2$-$Ser_3$-$Ser_4$-$Ser_5$-$Arg_6$-$Thr_7$-$Pro_8$-$Ser_9$-$Asp_{10}$-$Lys_{11}$-$Pro_{12}$-$Val_{13}$-$Ala_{14}$-$His_{15}$-$Val_{16}$-$Val_{17}$-$Ala_{18}$ (peptide 301) of mature human TNF-α;
wherein the antibody or fragment thereof competitively inhibits Mab 25 (ECACC Accession No. 89121401) for specific binding to mature human TNF-α; and
wherein when the antibody or fragment thereof binds mature human TNF-α the induction of endothelial procoagulant activity, cytotoxicity, tumor regression and tumor receptor binding to TNF-α are inhibited; and
wherein the cell line has been isolated.

27. The cell line according to claim 26,
where comparative binding specificity between the antibody or fragment thereof and the sheep anti-sera is determined by antibody-anti-sera competition assays in the presence of mature human TNF-α.

28. The cell line according to claim 26, wherein in the antibody-anti-sera competition assays the antibody is immobilized.

29. The cell line according to claim 26, wherein in the antibody-anti-sera competition assays the TNF-α is immobilized.

30. The cell line according to claim 26 wherein the antibody is a monoclonal antibody.

31. The cell line according to claim 26 wherein the antibody or fragment thereof does not competitively inhibit sheep anti-sera raised against an additional TNF-α peptide for specific binding to mature human TNF-α,
wherein the additional TNF-α peptide is a peptide consisting of residues $Ala_{22}$-$Glu_{23}$-$Gly_{24}$-$Gln_{25}$-$Leu_{26}$-$Gln_{27}$-$Trp_{28}$-$Leu_{29}$-$Asn_{30}$-$Arg_{31}$-$Arg_{32}$-$Ala_{33}$-$Asn_{34}$-$Ala_{35}$-$Leu_{36}$-$Leu_{37}$-$Ala_{38}$-$Asn_{39}$-$Gly_{40}$ (peptide 307) of mature human TNF-α.

32. The cell line according to claim 26 wherein the antibody or fragment thereof does not competitively inhibit sheep anti-sera raised against an additional TNF-α peptide for specific binding to mature human TNF-α,
wherein the additional TNF-α peptide is a peptide consisting of residues $Leu_{132}$-$Ser_{133}$-$Ala_{134}$-$Glu_{135}$-$Ile_{136}$-$Asn_{137}$-$Arg_{138}$-$Pro_{139}$-$Asp_{140}$-$Tyr_{141}$-$Leu_{142}$-$Asp_{143}$-$Phe_{144}$-$Ala_{145}$-$Glu_{146}$-$Ser_{147}$-$Gly_{148}$-$Gln_{149}$-$Val_{150}$ (peptide 305) of mature human TNF-α.

33. The cell line according to claim 26 wherein the antibody or fragment thereof does not competitively inhibit sheep anti-sera raised against an additional TNF-α peptide for specific binding to mature human TNF-α, wherein the additional TNF-α peptide is a peptide consisting of residues Val$_{13}$-Ala$_{14}$-His$_{15}$-Val$_{16}$-Val$_{17}$-Ala$_{18}$-Asn$_{19}$-Pro$_{20}$-Gln$_{21}$-Ala$_{22}$-Glu$_{23}$-Gly$_{24}$-Gln$_{25}$-Leu$_{26}$ (peptide 306) of mature human TNF-α.

34. The cell line according to claim 26 wherein the antibody or fragment thereof does not competitively inhibit sheep anti-sera raised against an additional TNF-α peptide for specific binding to mature human TNF-α,
wherein the additional TNF-α peptide is a peptide consisting of residues Ala$_{111}$-Lys$_{112}$-Pro$_{113}$-Trp$_{114}$-Tyr$_{115}$-Glu$_{116}$-Pro$_{117}$-Ile$_{118}$-Tyr$_{119}$-Leu$_{120}$ (peptide 275) of mature human TNF-α.

35. The cell line according to any one of claims 26-34, wherein the antibody is a humanized antibody.

36. A cell line producing an antibody or fragment thereof that specifically binds to mature human TNF-α,
wherein when the antibody or fragment thereof binds mature human TNF-α, the induction of endothelial procoagulant activity, cytotoxicity, tumor regression and tumor receptor binding to TNF-α are inhibited; and
wherein the antibody or fragment thereof competitively inhibits sheep anti-sera raised against a TNF-α peptide for specific binding to mature human TNF-α,
wherein the TNF-α peptide is a peptide consisting of residues Val$_1$-Arg$_2$-Ser$_3$-Ser$_4$-Ser$_5$-Arg$_6$-Thr$_7$-Pro$_8$-Ser$_9$-Asp$_{10}$-Lys$_{11}$-Pro$_{12}$-Val$_{13}$-Ala$_{14}$-His$_{15}$-Val$_{16}$-Val$_{17}$-Ala$_{18}$ (peptide 301) of mature human TNF-α; and
wherein the antibody or fragment thereof competitively inhibits sheep anti-sera raised against a second TNF-α peptide for specific binding to mature human TNF-α,
wherein the second TNF-α peptide is a peptide consisting of residues Ala$_{22}$-Glu$_{23}$-Gly$_{24}$-Gln$_{25}$-Leu$_{26}$-Gln$_{27}$-Trp$_{28}$-Leu$_{29}$-Asn$_{30}$-Arg$_{31}$-Arg$_{32}$-Ala$_{33}$-Asn$_{34}$-Ala$_{35}$-Leu$_{36}$-Leu$_{37}$-Ala$_{38}$-Asn$_{39}$-Gly$_{40}$ (peptide 307) of mature human TNF-α; and
wherein the cell line has been isolated.

37. The cell line according to claim 36,
where comparative binding specificity between the antibody or fragment thereof and the sheep anti-sera is determined by antibody-anti-sera competition assays in the presence of mature human TNF-α.

38. The cell line according to claim 36, wherein in the antibody-anti-sera competition assays the antibody is immobilized.

39. The cell line according to claim 36, wherein in the antibody-anti-sera competition assays the TNF-α is immobilized.

40. The cell line according to claim 36 wherein the antibody is a monoclonal antibody.

41. The cell line according to claim 36 wherein the antibody or fragment thereof does not competitively inhibit sheep anti-sera raised against an additional TNF-α peptide for specific binding to mature human TNF-α,
wherein the additional TNF-α peptide is a peptide consisting of residues Leu$_{132}$-Ser$_{133}$-Ala$_{134}$-Glu$_{135}$-Ile$_{136}$-Asn$_{137}$-Arg$_{138}$-Pro$_{139}$-Asp$_{140}$-Tyr$_{141}$-Leu$_{142}$-Asp$_{143}$-Phe$_{144}$-Ala$_{145}$-Glu$_{146}$-Ser$_{147}$-Gly$_{148}$-Gln$_{149}$-Val$_{150}$ (peptide 305) of mature human TNF-α.

42. The cell line according to claim 36 wherein the antibody or fragment thereof does not competitively inhibit sheep anti-sera raised against an additional TNF-α peptide for specific binding to mature human TNF-α,
wherein the additional TNF-α peptide is a peptide consisting of residues Val$_{13}$-Ala$_{14}$-His$_{15}$-Val$_{16}$-Val$_{17}$-Ala$_{18}$-Asn$_{19}$-Pro$_{20}$-Gln$_{21}$-Ala$_{22}$-Glu$_{23}$-Gly$_{24}$-Gln$_{25}$-Leu$_{26}$ (peptide 306) of mature human TNF-α.

43. The cell line according to claim 42 wherein the antibody or fragment thereof does not competitively inhibit sheep anti-sera raised against an additional TNF-α peptide for specific binding to mature human TNF-α,
wherein the additional TNF-α peptide is a peptide consisting of residues Ala$_{111}$-Lys$_{112}$-Pro$_{113}$-Trp$_{114}$-Tyr$_{115}$-Glu$_{116}$-Pro$_{117}$-Ile$_{118}$-Tyr$_{119}$-Leu$_{120}$ (peptide 275) of mature human TNF-α.

44. The cell line according to any one of claims 36-43, wherein the antibody is a humanized antibody.

45. A composition comprising a cell line producing an antibody or fragment thereof that specifically binds to mature human TNF-α,
wherein the antibody or fragment thereof competitively inhibits sheep anti-sera raised against a TNF-α peptide for specific binding to mature human TNF-α,
wherein the TNF-α peptide is a peptide consisting of residues Val$_1$-Arg$_2$-Ser$_3$-Ser$_4$-Ser$_5$-Arg$_6$-Thr$_7$-Pro$_8$-Ser$_9$-Asp$_{10}$-Lys$_{11}$-Pro$_{12}$-Val$_{13}$-Ala$_{14}$-His$_{15}$-Val$_{16}$-Val$_{17}$-Ala$_{18}$ (peptide 301) of mature human TNF-α; and
wherein when the antibody or fragment thereof binds mature human TNF-α, the induction of endothelial procoagulant activity, cytotoxicity, tumor regression and tumor receptor binding to TNF-α are inhibited;
wherein the antibody or fragment thereof competitively inhibits Mab 25 (ECACC Accession No. 89121401) for specific binding to mature human TNF-α; and
wherein the cell line has been isolated.

46. A composition comprising a cell line producing an antibody or fragment thereof that specifically binds to mature human TNF-α,
wherein when the antibody or fragment thereof binds mature human TNF-α, the induction of endothelial procoagulant activity, cytotoxicity, tumor regression and tumor receptor binding to TNF-α are inhibited; and,
wherein the antibody or fragment thereof competitively inhibits sheep anti-sera raised against a TNF-α peptide for specific binding to mature human TNF-α,
wherein the TNF-α peptide is a peptide consisting of residues Val$_1$-Arg$_2$-Ser$_3$-Ser$_4$-Ser$_5$-Arg$_6$-Thr$_7$-Pro$_8$-Ser$_9$-Asp$_{10}$-Lys$_{11}$-Pro$_{12}$-Val$_{13}$-Ala$_{14}$-His$_{15}$-Val$_{16}$-Val$_{17}$-Ala$_{18}$ (peptide 301) of mature human TNF-α; and
wherein the antibody or fragment thereof competitively inhibits sheep anti-sera raised against a second TNF-α peptide for specific binding to mature human TNF-α,
wherein the second TNF-α peptide is a peptide consisting of residues Ala$_{22}$-Glu$_{23}$-Gly$_{24}$-Gln$_{25}$-Leu$_{26}$-Gln$_{27}$-Trp$_{28}$-Leu$_{29}$-Asn$_{30}$-Arg$_{31}$-Arg$_{32}$-Ala$_{33}$-Asn$_{34}$-Ala$_{35}$-Leu$_{36}$-Leu$_{37}$-Ala$_{38}$-Asn$_{39}$-Gly$_{40}$ (peptide 307) of mature human TNF-α; and
wherein the cell line has been isolated.

47. A cell line producing an antibody or fragment thereof that specifically binds to mature human TNF-α,
wherein when the antibody or fragment thereof binds mature human TNF-α, the induction of endothelial procoagulant activity is inhibited; and
wherein the antibody or fragment thereof competitively inhibits sheep anti-sera raised against a TNF-α peptide for specific binding to mature human TNF-α,
wherein the TNF-α peptide is a peptide consisting of residues Val$_1$-Arg$_2$-Ser$_3$-Ser$_4$-Ser$_5$-Arg$_6$-Thr$_7$-Pro$_8$-Ser$_9$-Asp$_{10}$-Lys$_{11}$-Pro$_{12}$-Val$_{13}$-Ala$_{14}$-His$_{15}$-Val$_{16}$-Val$_{17}$-Ala$_{18}$ (peptide 301) of mature human TNF-α; and
wherein the antibody or fragment thereof competitively inhibits sheep anti-sera raised against a second TNF-α peptide for specific binding to mature human TNF-α, wherein the second TNF-α peptide is a peptide consisting of residues Ala$_{22}$-Glu$_{23}$-Gly$_{24}$-Gln$_{25}$-Leu$_{26}$-Gln$_{27}$-Trp$_{28}$-Leu$_{29}$-Asn$_{30}$-Arg$_{31}$-Arg$_{32}$-Ala$_{33}$-Asn$_{34}$-Ala$_{35}$-Leu$_{36}$-Leu$_{37}$-Ala$_{38}$-Asn$_{39}$-Gly$_{40}$ (peptide 307) of mature human TNF-α; and wherein the cell line has been isolated.

48. The cell line according to claim 47, wherein the antibody is a monoclonal antibody.

49. The cell line according to claim 47, wherein the antibody or fragment thereof inhibits tumor receptor binding to TNF-α.

50. The cell line according to claim 47, wherein the antibody or fragment thereof has no effect on tumor receptor binding to TNF-α.

51. The cell line according to claim 49, wherein the antibody or fragment thereof inhibits cytotoxicity.

52. The cell line according to claim 47, wherein the antibody or fragment thereof inhibits cytotoxicity.

53. The cell line according to claim 52, wherein the antibody or fragment thereof inhibits tumor regression.

54. The cell line according to claim 49, wherein the antibody or fragment thereof inhibits tumor regression.

55. The cell line according to claim 47, wherein the antibody or fragment thereof inhibits tumor regression.

56. The cell line according to claim 47, where comparative binding specificity between the antibody or fragment thereof and the sheep anti-sera is determined by antibody-anti-sera competition assays in the presence of mature human TNF-α.

57. The cell line according to claim 56, wherein in the antibody-anti-sera competition assays the antibody is immobilized.

58. The cell line according to claim 56, wherein in the antibody-anti-sera competition assays the TNF-α is immobilized.

59. The cell line according to claim 56, wherein the antibody or fragment thereof inhibits tumor receptor binding to TNF-α.

60. The cell line according to claim 56, wherein the antibody or fragment thereof has no effect on tumor receptor binding to TNF-α.

61. The cell line according to claim 56, wherein the antibody or fragment thereof inhibits cytotoxicity.

62. The cell line according to claim 56, wherein the antibody or fragment thereof inhibits tumor regression.

63. The cell line according to claim 47, wherein the antibody or fragment thereof does not competitively inhibit sheep anti-sera raised against an additional TNF-α peptide for specific binding to mature human TNF-α, wherein the additional TNF-α peptide is a peptide consisting of residues Ala$_{111}$-Lys$_{112}$-Pro$_{113}$-Trp$_{114}$-Tyr$_{115}$-Glu$_{116}$-Pro$_{117}$-Ile$_{118}$-Tyr$_{119}$-Leu$_{120}$ (peptide 275) of mature human TNF-α.

64. The cell line according to claim 47, wherein the antibody or fragment thereof does not competitively inhibit sheep anti-sera raised against an additional TNF-α peptide for specific binding to mature human TNF-α, wherein the additional TNF-α peptide is a peptide consisting of residues Leu$_{132}$-Ser$_{133}$-Ala$_{134}$-Glu$_{135}$-Ile$_{136}$-Asn$_{137}$-Arg$_{138}$-Pro$_{139}$-Asp$_{140}$-Tyr$_{141}$-Leu$_{142}$-Asp$_{143}$-Phe$_{144}$-Ala$_{145}$-Glu$_{146}$-Ser$_{147}$-Gly$_{148}$-Gln$_{149}$-Val$_{150}$ (peptide 305) of mature human TNF-α.

65. The cell line according to claim 47, wherein the antibody or fragment thereof does not competitively inhibit sheep anti-sera raised against an additional TNF-α peptide for specific binding to mature human TNF-α, wherein the additional TNF-α peptide is a peptide consisting of residues Val$_{13}$-Ala$_{14}$-His$_{15}$-Val$_{16}$-Val$_{17}$-Ala$_{18}$-Asn$_{19}$-Pro$_{20}$-Gln$_{21}$-Ala$_{22}$-Glu$_{23}$-Gly$_{24}$-Gln$_{25}$-Leu$_{26}$ (peptide 306) of mature human TNF-α.

66. The cell line according to any one of claims 47-65, wherein the antibody is a humanized antibody.

67. A composition comprising a cell line producing an antibody or fragment thereof that specifically binds to mature human TNF-α, wherein when the antibody or fragment thereof binds mature human TNF-α, the induction of endothelial procoagulant activity is inhibited; and wherein the antibody or fragment thereof competitively inhibits sheep anti-sera raised against a TNF-α peptide for specific binding to mature human TNF-α, wherein the TNF-α peptide is a peptide consisting of residues Val$_1$-Arg$_2$-Ser$_3$-Ser$_4$-Ser$_5$-Arg$_6$-Thr$_7$-Pro$_8$-Ser$_9$-Asp$_{10}$-Lys$_{11}$-Pro$_{12}$-Val$_{13}$-Ala$_{14}$-His$_{15}$-Val$_{16}$-Val$_{17}$-Ala$_{18}$ (peptide 301) of mature human TNF-α; and, wherein the antibody or fragment thereof competitively inhibits sheep anti-sera raised against a second TNF-α peptide for specific binding to mature human TNF-α, wherein the second TNF-α peptide is a peptide consisting of residues Ala$_{22}$-Glu$_{23}$-Gly$_{24}$-Gln$_{25}$-Leu$_{26}$-Gln$_{27}$-Trp$_{28}$-Leu$_{29}$-Asn$_{30}$-Arg$_{31}$-Arg$_{32}$-Ala$_{33}$-Asn$_{34}$-Ala$_{35}$-Leu$_{36}$-Leu$_{37}$-Ala$_{38}$-Asn$_{39}$-Gly$_{40}$ (peptide 307) of mature human TNF-α; and wherein the cell line has been isolated.

68. A cell line producing an antibody or fragment thereof that specifically binds to mature human TNF-α, wherein when the antibody or fragment thereof binds mature human TNF-α, the induction of endothelial procoagulant activity is inhibited; and wherein the antibody or fragment thereof competitively inhibits sheep anti-sera raised against a TNF-α peptide for specific binding to mature human TNF-α, wherein the TNF-α peptide is a peptide consisting of residues Val$_1$-Arg$_2$-Ser$_3$-Ser$_4$-Ser$_5$-Arg$_6$-Thr$_7$-Pro$_8$-Ser$_9$-Asp$_{10}$-Lys$_{11}$-Pro$_{12}$-Val$_{13}$-Ala$_{14}$-His$_{15}$-Val$_{16}$-Val$_{17}$-Ala$_{18}$ (peptide 301) of mature human TNF-α; and wherein the antibody or fragment thereof competitively inhibits sheep anti-sera raised against a second TNF-α peptide for specific binding to mature human TNF-α, wherein the second TNF-α peptide is a peptide consisting of residues Val$_{13}$-Ala$_{14}$-His$_{15}$-Val$_{16}$-Val$_{17}$-Ala$_{18}$-Asn$_{19}$-Pro$_{20}$-Gln$_{21}$-Ala$_{22}$-Glu$_{23}$-Gly$_{24}$-Gln$_{25}$-Leu$_{26}$ (peptide 306) of mature human TNF-α; and wherein the cell line has been isolated.

69. The cell line according to claim 68, wherein the antibody is a monoclonal antibody.

70. The cell line according to claim 68, wherein the antibody or fragment thereof has no effect on cytotoxicity.

71. The cell line according to claim 70, wherein the antibody or fragment thereof enhances tumor regression.

72. The cell line according to claim 68, wherein the antibody or fragment thereof enhances tumor regression.

73. The cell line according to claim 68, wherein the antibody or fragment thereof has no effect on tumor receptor binding to TNF-α.

74. The cell line according to claim 68, where comparative binding specificity between the antibody or fragment thereof and the sheep anti-sera is determined by antibody-anti-sera competition assays in the presence of mature human TNF-α.

75. The cell line according to claim 74, wherein in the antibody-anti-sera competition assays the antibody is immobilized.

76. The cell line according to claim 74, wherein in the antibody-anti-sera competition assays the TNF-α is immobilized.

77. The cell line according to claim 74, wherein the antibody or fragment thereof has no effect on cytotoxicity.

78. The cell line according to claim 74, wherein the antibody or fragment thereof enhances tumor regression.

79. The cell line according to claim 74, wherein the antibody or fragment thereof has no effect on tumor receptor binding to TNF-α.

80. The cell line according to claim 68, wherein the antibody or fragment thereof does not competitively inhibit sheep anti-sera raised against an additional TNF-α peptide for specific binding to mature human TNF-α,
wherein the additional TNF-α peptide is a peptide consisting of residues $Ala_{111}$-$Lys_{112}$-$Pro_{113}$-$Trp_{114}$-$Tyr_{115}$-$Glu_{116}$-$Pro_{117}$-$Ile_{118}$-$Tyr_{119}$-$Leu_{120}$ (peptide 275) of mature human TNF-α.

81. The cell line according to claim 68, wherein the antibody or fragment thereof does not competitively inhibit sheep anti-sera raised against an additional TNF-α peptide for specific binding to mature human TNF-α,
wherein the additional TNF-α peptide is a peptide consisting of residues $Ala_{22}$-$Glu_{23}$-$Gly_{24}$-$Gln_{25}$-$Leu_{26}$-$Gln_{27}$-$Trp_{28}$-$Leu_{29}$-$Asn_{30}$-$Arg_{31}$-$Arg_{32}$-$Ala_{33}$-$Asn_{34}$-$Ala_{35}$-$Leu_{36}$-$Leu_{37}$-$Ala_{38}$-$Asn_{39}$-$Gly_{40}$ (peptide 307) of mature human TNF-α.

82. The cell line according to claim 68, wherein the antibody competitively inhibits sheep anti-sera raised against an additional TNF-α peptide for specific binding to mature human TNF-α,
wherein the additional TNF-α peptide is a peptide consisting of residues $Leu_{132}$-$Ser_{133}$-$Ala_{134}$-$Glu_{135}$-$Ile_{136}$-$Asn_{137}$-$Arg_{138}$-$Pro_{139}$-$Asp_{140}$-$Tyr_{141}$-$Leu_{142}$-$Asp_{143}$-$Phe_{144}$-$Ala_{145}$-$Glu_{146}$-$Ser_{147}$-$Gly_{148}$-$Gln_{149}$-$Val_{150}$ (peptide 305) of mature human TNF-α.

83. The cell line according to any one of claims 68-82, wherein the antibody is a humanized antibody.

84. The cell line according to any one of claims 68-82, wherein the antibody is a chimeric antibody.

85. The cell line according to any one of claims 68-82, wherein the antibody is a human antibody.

86. A composition comprising a cell line producing an antibody or fragment thereof that specifically binds to mature human TNF-α,
wherein when the antibody or fragment thereof binds mature human TNF-α, the induction of endothelial procoagulant activity is inhibited; and
wherein the antibody or fragment thereof competitively inhibits sheep anti-sera raised against a TNF-α peptide for specific binding to mature human TNF-α,
wherein the TNF-α peptide is a peptide consisting of residues $Val_1$-$Arg_2$-$Ser_3$-$Ser_4$-$Ser_5$-$Arg_6$-$Thr_7$-$Pro_8$-$Ser_9$-$Asp_{10}$-$Lys_{11}$-$Pro_{12}$-$Val_{13}$-$Ala_{14}$-$His_{15}$-$Val_{16}$-$Val_{17}$-$Ala_{18}$ (peptide 301) of mature human TNF-α; and,
wherein the antibody or fragment thereof competitively inhibits sheep anti-sera raised against a second TNF-α peptide for specific binding to mature human TNF-α,
wherein the second TNF-α peptide is a peptide consisting of residues $Val_{13}$-$Ala_{14}$-$His_{15}$-$Val_{16}$-$Val_{17}$-$Ala_{18}$-$Asn_{19}$-$Pro_{20}$-$Gln_{21}$-$Ala_{22}$-$Glu_{23}$-$Gly_{24}$-$Gln_{25}$-$Leu_{26}$ (peptide 306) of mature human TNF-α; and
wherein the cell line has been isolated.

87. A cell line producing a single domain antibody or fragment thereof that specifically binds to mature human TNF-α,
wherein when the antibody or fragment thereof binds mature human TNF-α, the induction of endothelial procoagulant activity is inhibited; and
wherein the antibody or fragment thereof competitively inhibits sheep anti-sera raised against a TNF-α peptide for specific binding to mature human TNF-α,
wherein the TNF-α peptide is a peptide consisting of residues $Val_1$-$Arg_2$-$Ser_3$-$Ser_4$-$Ser_5$-$Arg_6$-$Thr_7$-$Pro_8$-$Ser_9$-$Asp_{10}$-$Lys_{11}$-$Pro_{12}$-$Val_{13}$-$Ala_{14}$-$His_{15}$-$Val_{16}$-$Val_{17}$-$Ala_{18}$ (peptide 301) of mature human TNF-α; and
wherein the antibody or fragment thereof competitively inhibits Mab 25 (ECACC Accession No. 89121401) for specific binding to mature human TNF-α; and
wherein the cell line has been isolated.

88. The cell line according to claim 87, wherein the antibody is a monoclonal antibody.

89. The cell line according to claim 87, wherein the antibody or fragment thereof inhibits tumor receptor binding to TNF-α.

90. The cell line according to claim 87, wherein the antibody or fragment thereof has no effect on tumor receptor binding to TNF-α.

91. The cell line according to claim 89, wherein the antibody or fragment thereof inhibits cytotoxicity.

92. The cell line according to claim 87, wherein the antibody or fragment thereof inhibits cytotoxicity.

93. The cell line according to claim 92, wherein the antibody or fragment thereof inhibits tumor regression.

94. The cell line according to claim 91, wherein the antibody or fragment thereof inhibits tumor regression.

95. The cell line according to claim 89, wherein the antibody or fragment thereof inhibits tumor regression.

96. The cell line according to claim 87, wherein the antibody or fragment thereof inhibits tumor regression.

97. The cell line according to claim 87, wherein the antibody or fragment thereof has no effect on tumor regression.

98. The cell line according to claim 87, where comparative binding specificity between the antibody or fragment thereof and the sheep anti-sera is determined by antibody-anti-sera competition assays in the presence of mature human TNF-α.

99. The cell line according to claim 98, wherein in the antibody-anti-sera competition assays the antibody is immobilized.

100. The cell line according to claim 98, wherein in the antibody-anti-sera competition assays the TNF-α is immobilized.

101. The cell line according to claim 98, wherein the antibody or fragment thereof inhibits tumor receptor binding to TNF-α.

102. The cell line according to claim 98, wherein the antibody or fragment thereof has no effect on tumor receptor binding to TNF-α.

103. The cell line according to claim 98, wherein the antibody or fragment thereof inhibits cytotoxicity.

104. The cell line according to claim 87, wherein the antibody or fragment thereof has no effect on cytotoxicity.

105. The cell line according to claim 98, wherein the antibody or fragment thereof inhibits tumor regression.

106. The cell line according to claim 87, wherein the antibody or fragment thereof does not competitively inhibit sheep anti-sera raised against an additional TNF-α peptide for specific binding to mature human TNF-α,
wherein the additional TNF-α peptide is a peptide consisting of residues $Ala_{111}$-$Lys_{112}$-$Pro_{113}$-$Trp_{114}$-$Tyr_{115}$-$Glu_{116}$-$Pro_{117}$-$Ile_{118}$-$Tyr_{119}$-$Leu_{120}$ (peptide 275) of mature human TNF-α.

107. The cell line according to claim 87, wherein the antibody or fragment thereof does not competitively inhibit sheep anti-sera raised against an additional TNF-α peptide for specific binding to mature human TNF-α, wherein the TNF-α peptide is a peptide consisting of residues Leu$_{132}$-Ser$_{133}$-Ala$_{134}$-Glu$_{135}$-Ile$_{136}$-Asn$_{137}$-Arg$_{138}$-Pro$_{139}$-Asp$_{140}$-Tyr$_{141}$-Leu$_{142}$-Asp$_{143}$-Phe$_{144}$-Ala$_{145}$-Glu$_{146}$-Ser$_{147}$-Gly$_{148}$-Gln$_{149}$-Val$_{150}$ (peptide 305) of mature human TNF-α.

108. The cell line according to claim 87, wherein the antibody or fragment thereof does not competitively inhibit sheep anti-sera raised against an additional TNF-α peptide for specific binding to mature human TNF-α,
    wherein the additional TNF-α peptide is a peptide consisting of residues Val$_{13}$-Ala$_{14}$-His$_{15}$-Val$_{16}$-Val$_{17}$-Ala$_{18}$-Asn$_{19}$-Pro$_{20}$-Gln$_{21}$-Ala$_{22}$-Glu$_{23}$-Gly$_{24}$-Gln$_{25}$-Leu$_{26}$ (peptide 306) of mature human TNF-α.

109. The cell line according to claim 87, wherein the antibody or fragment thereof does not competitively inhibit sheep anti-sera raised against an additional TNF-α peptide for specific binding to mature human TNF-α,
    wherein the additional TNF-α peptide is a peptide consisting of residues Ala$_{22}$-Glu$_{23}$-Gly$_{24}$-Gln$_{25}$-Leu$_{26}$-Gln$_{27}$-Trp$_{28}$-Leu$_{29}$-Asn$_{30}$-Arg$_{31}$-Arg$_{32}$-Ala$_{33}$-Asn$_{34}$-Ala$_{35}$-Leu$_{36}$-Leu$_{37}$-Ala$_{38}$-Asn$_{39}$-Gly$_{40}$ (peptide 307) of mature human TNF-α.

110. The cell line according to any one of claims 87-109, wherein the antibody is a humanized antibody.

111. The cell line according to any one of claims 87-109, wherein the antibody is a chimeric antibody.

112. The cell line according to any one of claims 87-109, wherein the antibody is a human antibody.

113. A composition comprising a cell line producing a single domain antibody or fragment thereof that specifically binds to mature human TNF-α,
    wherein when the antibody or fragment thereof binds mature human TNF-α, the induction of endothelial procoagulant activity is inhibited; and
    wherein the antibody or fragment thereof competitively inhibits sheep anti-sera raised against a TNF-α peptide for specific binding to mature human TNF-α,
    wherein the TNF-α peptide is a peptide consisting of residues Val$_1$-Arg$_2$-Ser$_3$-Ser$_4$-Ser$_5$-Arg$_6$-Thr$_7$-Pro$_8$-Ser$_9$-Asp$_{10}$-Lys$_{11}$-Pro$_{12}$-Val$_{13}$-Ala$_{14}$-His$_{15}$-Val$_{16}$-Val$_{17}$-Ala$_{18}$ (peptide 301) of mature human TNF-α; and
    wherein the antibody or fragment thereof competitively inhibits Mab 25 (ECACC Accession No. 89121401) for specific binding to mature human TNF-α; and
    wherein the cell line has been isolated.

114. A cell line producing a single domain antibody or fragment thereof that specifically binds to mature human TNF-α,
    wherein the antibody or fragment thereof competitively inhibits sheep anti-sera raised against a TNF-α peptide for specific binding to mature human TNF-α, and
    wherein the TNF-α peptide is a peptide consisting of residues Val$_1$-Arg$_2$-Ser$_3$-Ser$_4$-Ser$_5$-Arg$_6$-Thr$_7$-Pro$_8$-Ser$_9$-Asp$_{10}$-Lys$_{11}$-Pro$_{12}$-Val$_{13}$-Ala$_{14}$-His$_{15}$-Val$_{16}$-Val$_{17}$-Ala$_{18}$ (peptide 301) of mature human TNF-α;
    wherein when the antibody or fragment thereof binds mature human TNF-α the induction of endothelial procoagulant activity, cytotoxicity, tumor regression and tumor receptor binding to TNF-α are inhibited; and
    wherein the antibody or fragment thereof competitively inhibits Mab 25 (ECACC Accession No. 89121401) for specific binding to mature human TNF-α; and
    wherein the cell line has been isolated.

115. The cell line according to claim 114, where comparative binding specificity between the antibody or fragment thereof and the sheep anti-sera is determined by antibody-anti-sera competition assays in the presence of mature human TNF-α.

116. The cell line according to claim 114, wherein in the antibody-anti-sera competition assays the antibody is immobilized.

117. The cell line according to claim 114, wherein in the antibody-anti-sera competition assays the TNF-α is immobilized.

118. The cell line according to claim 114 wherein the antibody is a monoclonal antibody.

119. The cell line according to claim 114 wherein the antibody or fragment thereof does not competitively inhibit sheep anti-sera raised against an additional TNF -α peptide for specific binding to mature human TNF-α,
    wherein the additional TNF-α peptide is a peptide consisting of residues Ala$_{22}$-Glu$_{23}$-Gly$_{24}$-Gln$_{25}$-Leu$_{26}$-Gln$_{27}$-Trp$_{28}$-Leu$_{29}$-Asn$_{30}$-Arg$_{31}$-Arg$_{32}$-Ala$_{33}$-Asn$_{34}$-Ala$_{35}$-Leu$_{36}$-Leu$_{37}$-Ala$_{38}$-Asn$_{39}$-Gly$_{40}$ (peptide 307) of mature human TNF-α.

120. The cell line according to claim 114 wherein the antibody or fragment thereof does not competitively inhibit sheep anti-sera raised against an additional TNF -α peptide for specific binding to mature human TNF-α,
    wherein the additional TNF-α peptide is a peptide consisting of residues Leu$_{132}$-Ser$_{133}$-Ala$_{134}$-Glu$_{135}$-Ile$_{136}$-Asn$_{137}$-Arg$_{138}$-Pro$_{139}$-Asp$_{140}$-Tyr$_{141}$-Leu$_{142}$-Asp$_{143}$-Phe$_{144}$-Ala$_{145}$-Glu$_{146}$-Ser$_{147}$-Gly$_{148}$-Gln$_{149}$-Val$_{150}$ (peptide 305) of mature human TNF-α.

121. The cell line according to claim 114 wherein the antibody or fragment thereof does not competitively inhibit sheep anti-sera raised against an additional TNF -α peptide for specific binding to mature human TNF-α,
    wherein the additional TNF-α peptide is a peptide consisting of residues Val$_{13}$-Ala$_{14}$-His$_{15}$-Val$_{16}$-Val$_{17}$-Ala$_{18}$-Asn$_{19}$-Pro$_{20}$-Gln$_{21}$-Ala$_{22}$-Glu$_{23}$-Gly$_{24}$-Gln$_{25}$-Leu$_{26}$ (peptide 306) of mature human TNF-α.

122. The cell line according to claim 114 wherein the antibody or fragment thereof does not competitively inhibit sheep anti-sera raised against an additional TNF -α peptide for specific binding to mature human TNF-α,
    wherein the additional TNF-α peptide is a peptide consisting of residues Ala$_{111}$-Lys$_{112}$-Pro$_{113}$-Trp$_{114}$-Tyr$_{115}$-Glu$_{116}$-Pro$_{117}$-Ile$_{118}$-Tyr$_{119}$-Leu$_{120}$ (peptide 275) of mature human TNF-α.

123. The cell line according to any one of claims 114-122, wherein the antibody is a humanized antibody.

124. A cell line producing a single domain antibody or fragment thereof that specifically binds to mature human TNF-α,
    wherein when the antibody or fragment thereof binds mature human TNF-α, the induction of endothelial procoagulant activity, cytotoxicity, tumor regression and tumor receptor binding to TNF-α are inhibited; and
    wherein the antibody or fragment thereof competitively inhibits sheep anti-sera raised against a TNF-α peptide for specific binding to mature human TNF-α,
    wherein the TNF-α peptide is a peptide consisting of residues Val$_1$-Arg$_2$-Ser$_3$-Ser$_4$-Ser$_5$-Arg$_6$-Thr$_7$-Pro$_8$-Ser$_9$-Asp$_{10}$-Lys$_{11}$-Pro$_{12}$-Val$_{13}$-Ala$_{14}$-His$_{15}$-Val$_{16}$-Val$_{17}$-Ala$_{18}$ (peptide 301) of mature human TNF-α; and
    wherein the antibody or fragment thereof competitively inhibits sheep anti-sera raised against a second TNF-α peptide for specific binding to mature human TNF-α,
    wherein the second TNF-α peptide is a peptide consisting of residues Ala$_{22}$-Glu$_{23}$-Gly$_{24}$-Gln$_{25}$-Leu$_{26}$-Gln$_{27}$-

Trp$_{28}$-Leu$_{29}$-Asn$_{30}$-Arg$_{31}$-Arg$_{32}$-Ala$_{33}$-Asn$_{34}$-Ala$_{35}$-Leu$_{36}$-Leu$_{37}$-Ala$_{38}$-Asn$_{39}$-Gly$_{40}$ (peptide 307) of mature human TNF-α; and wherein the cell line has been isolated.

125. The cell line according to claim 124, where comparative binding specificity between the antibody or fragment thereof and the sheep anti-sera is determined by antibody-anti-sera competition assays in the presence of mature human TNF-α.

126. The cell line according to claim 124, wherein in the antibody-anti-sera competition assays the antibody is immobilized.

127. The cell line according to claim 124, wherein in the antibody-anti-sera competition assays the TNF-α is immobilized.

128. The cell line according to claim 124 wherein the antibody is a monoclonal antibody.

129. The cell line according to claim 124 wherein the antibody or fragment thereof does not competitively inhibit sheep anti-sera raised against an additional TNF α peptide for specific binding to mature human TNF-α, wherein the additional TNF-α peptide is a peptide consisting of residues Leu$_{132}$-Ser$_{133}$-Ala$_{134}$-Glu$_{135}$-Ile$_{136}$-Asn$_{137}$-Arg$_{138}$-Pro$_{139}$-Asp$_{140}$-Tyr$_{141}$-Leu$_{142}$-Asp$_{143}$-Phe$_{144}$-Ala$_{145}$-Glu$_{146}$-Ser$_{147}$-Gly$_{148}$-Gln$_{149}$-Val$_{150}$ (peptide 305) of mature human TNF-α.

130. The cell line according to claim 124 wherein the antibody or fragment thereof does not competitively inhibit sheep anti-sera raised against an additional TNF α peptide for specific binding to mature human TNF-α, wherein the additional TNF-α peptide is a peptide consisting of residues Val$_{13}$-Ala$_{14}$-His$_{15}$-Val$_{16}$-Val$_{17}$-Ala$_{18}$-Asn$_{19}$-Pro$_{20}$-Gln$_{21}$-Ala$_{22}$-Glu$_{23}$-Gly$_{24}$-Gln$_{25}$-Leu$_{26}$ (peptide 306) of mature human TNF-α.

131. The cell line according to claim 124 wherein the antibody or fragment thereof does not competitively inhibit sheep anti-sera raised against an additional TNF -α peptide for specific binding to mature human TNF-α, wherein the additional TNF-α peptide is a peptide consisting of residues Ala$_{111}$-Lys$_{112}$-Pro$_{113}$-Trp$_{114}$-Tyr$_{115}$-Glu$_{116}$-Pro$_{117}$-Ile$_{118}$-Tyr$_{119}$-Leu$_{120}$ (peptide 275) of mature human TNF-α.

132. The cell line according to any one of claims 124-131, wherein the antibody is a humanized antibody.

133. A composition comprising a cell line producing a single domain antibody or fragment thereof that specifically binds to mature human TNF-α, wherein the antibody or fragment thereof competitively inhibits sheep anti-sera raised against a TNF-α peptide for specific binding to mature human TNF-α, wherein the TNF-α peptide is a peptide consisting of residues Val$_1$-Arg$_2$-Ser$_3$-Ser$_4$-Ser$_5$-Arg$_6$-Thr$_7$-Pro$_8$-Ser$_9$-Asp$_{10}$-Lys$_{11}$-Pro$_{12}$-Val$_{13}$-Ala$_{14}$-His$_{15}$-Val$_{16}$-Val$_{17}$-Ala$_{18}$ (peptide 301) of mature human TNF-α; and wherein when the antibody or fragment thereof binds mature human TNF-α, the induction of endothelial procoagulant activity, cytotoxicity, tumor regression and tumor receptor binding to TNF-α are inhibited; and wherein the antibody or fragment thereof competitively inhibits Mab 25 (ECACC Accession No. 89121401) for specific binding to mature human TNF-α; and wherein the cell line has been isolated.

134. A composition comprising a cell line producing a single domain antibody or fragment thereof that specifically binds to mature human TNF-α, wherein when the antibody or fragment thereof binds mature human TNF-α, the induction of endothelial procoagulant activity, cytotoxicity, tumor regression and tumor receptor binding to TNF-α are inhibited; and wherein the antibody or fragment thereof competitively inhibits sheep anti-sera raised against a TNF-α peptide for specific binding to mature human TNF-α, wherein the TNF-α peptide is a peptide consisting of residues Val$_1$-Arg$_2$-Ser$_3$-Ser$_4$-Ser$_5$-Arg$_6$-Thr$_7$-Pro$_8$-Ser$_9$-Asp$_{10}$-Lys$_{11}$-Pro$_{12}$-Val$_{13}$-Ala$_{14}$-His$_{15}$-Val$_{16}$-Val$_{17}$-Ala$_{18}$ (peptide 301) of mature human TNF-α; and wherein the antibody or fragment thereof competitively inhibits sheep anti-sera raised against a second TNF-α peptide for specific binding to mature human TNF-α, wherein the second TNF-α peptide is a peptide consisting of residues Ala$_{22}$-Glu$_{23}$-Gly$_{24}$-Gln$_{25}$-Leu$_{26}$-Gln$_{27}$-Trp$_{28}$-Leu$_{29}$-Asn$_{30}$-Arg$_{31}$-Arg$_{32}$-Ala$_{33}$-Asn$_{34}$-Ala$_{35}$-Leu$_{36}$-Leu$_{37}$-Ala$_{38}$-Asn$_{39}$-Gly$_{40}$ (peptide 307) of mature human TNF-α; and wherein the cell line has been isolated.

135. A cell line producing a single domain antibody or fragment thereof that specifically binds to mature human TNF-α, wherein when the antibody or fragment thereof binds mature human TNF-α, the induction of endothelial procoagulant activity is inhibited; and wherein the antibody or fragment thereof competitively inhibits sheep anti-sera raised against a TNF-α peptide for specific binding to mature human TNF-α, wherein the TNF-α peptide is a peptide consisting of residues Val$_1$-Arg$_2$-Ser$_3$-Ser$_4$-Ser$_5$-Arg$_6$-Thr$_7$-Pro$_8$-Ser$_9$-Asp$_{10}$-Lys$_{11}$-Pro$_{12}$-Val$_{13}$-Ala$_{14}$-His$_{15}$-Val$_{16}$-Val$_{17}$-Ala$_{18}$ (peptide 301) of mature human TNF-α; and wherein the antibody or fragment thereof competitively inhibits sheep anti-sera raised against a second TNF-α peptide for specific binding to mature human TNF-α, wherein the second TNF-α peptide is a peptide consisting of residues Ala$_{22}$-Glu$_{23}$-Gly$_{24}$-Gln$_{25}$-Leu$_{26}$-Gln$_{27}$-Trp$_{28}$-Leu$_{29}$-Asn$_{30}$-Arg$_{31}$-Arg$_{32}$-Ala$_{33}$-Asn$_{34}$-Ala$_{35}$-Leu$_{36}$-Leu$_{37}$-Ala$_{38}$-Asn$_{39}$-Gly$_{40}$ (peptide 307) of mature human TNF-α; and wherein the cell line has been isolated.

136. The cell line according to claim 135, wherein the antibody is a monoclonal antibody.

137. The cell line according to claim 135, wherein the antibody or fragment thereof inhibits tumor receptor binding to TNF-α.

138. The cell line according to claim 135, wherein the antibody or fragment thereof has no effect on tumor receptor binding to TNF-α.

139. The cell line according to claim 137, wherein the antibody or fragment thereof inhibits cytotoxicity.

140. The cell line according to claim 135, wherein the antibody or fragment thereof inhibits cytotoxicity.

141. The cell line according to claim 135, wherein the antibody or fragment thereof inhibits tumor regression.

142. The cell line according to claim 140, wherein the antibody or fragment thereof inhibits tumor regression.

143. The cell line according to claim 137, wherein the antibody or fragment thereof inhibits tumor regression.

144. The cell line according to claim 135, where comparative binding specificity between the antibody or fragment thereof and the sheep anti-sera is determined by antibody-anti-sera competition assays in the presence of mature human TNF-α.

145. The cell line according to claim 144, wherein in the antibody-anti-sera competition assays the antibody is immobilized.

146. The cell line according to claim 144, wherein in the antibody-anti-sera competition assays the TNF-α is immobilized.

147. The cell line according to claim 144, wherein the antibody or fragment thereof inhibits tumor receptor binding to TNF-α.

148. The cell line according to claim 144, wherein the antibody or fragment thereof has no effect on tumor receptor binding to TNF-α.

149. The cell line according to claim 144, wherein the antibody or fragment thereof inhibits cytotoxicity.

150. The cell line according to claim 144, wherein the antibody or fragment thereof inhibits tumor regression.

151. The cell line according to claim 135, wherein the antibody or fragment thereof does not competitively inhibit sheep anti-sera raised against an additional TNF -α peptide for specific binding to mature human TNF-α,
   wherein the additional TNF-α peptide is a peptide consisting of residues $Ala_{111}$-$Lys_{112}$-$Pro_{113}$-$Trp_{114}$-$Tyr_{115}$-$Glu_{116}$-$Pro_{117}$-$Ile_{118}$-$Tyr_{119}$-$Leu_{120}$ (peptide 275) of mature human TNF-α.

152. The cell line according to claim 135, wherein the antibody or fragment thereof does not competitively inhibit sheep anti-sera raised against an additional TNF α peptide for specific binding to mature human TNF-α,
   wherein the additional TNF-α peptide is a peptide consisting of residues $Leu_{132}$-$Ser_{133}$-$Ala_{134}$-$Glu_{135}$-$Ile_{136}$-$Asn_{137}$-$Arg_{138}$-$Pro_{139}$-$Asp_{140}$-$Tyr_{141}$-$Leu_{142}$-$Asp_{143}$-$Phe_{144}$-$Ala_{145}$-$Glu_{146}$-$Ser_{147}$-$Gly_{148}$-$Gln_{149}$-$Val_{150}$ (peptide 305) of mature human TNF-α.

153. The cell line according to claim 135, wherein the antibody or fragment thereof does not competitively inhibit sheep anti-sera raised against an additional TNF -α peptide for specific binding to mature human TNF-α,
   wherein the additional TNF-α peptide is a peptide consisting of residues $Val_{13}$-$Ala_{14}$-$His_{15}$-$Val_{16}$-$Val_{17}$-$Ala_{18}$-$Asn_{19}$-$Pro_{20}$-$Gln_{21}$-$Ala_{22}$-$Glu_{23}$-$Gly_{24}$-$Gln_{25}$-$Leu_{26}$ (peptide 306) of mature human TNF-α.

154. The cell line according to any one of claims 135-153, wherein the antibody is a humanized antibody.

155. A composition comprising a cell line producing a single domain antibody or fragment thereof that specifically binds to mature human TNF-α,
   wherein when the antibody or fragment thereof binds mature human TNF-α, the induction of endothelial pro-coagulant activity is inhibited; and
   wherein the antibody or fragment thereof competitively inhibits sheep anti-sera raised against a TNF-α peptide for specific binding to mature human TNF-α,
   wherein the TNF-α peptide is a peptide consisting of residues $Val_1$-$Arg_2$-$Ser_3$-$Ser_4$-$Ser_5$-$Arg_6$-$Thr_7$-$Pro_8$-$Ser_9$-$Asp_{10}$-$Lys_{11}$-$Pro_{12}$-$Val_{13}$-$Ala_{14}$-$His_{15}$-$Val_{16}$-$Val_{17}$-$Ala_{18}$ (peptide 301) of mature human TNF-α; and
   wherein the antibody or fragment thereof competitively inhibits sheep anti-sera raised against a second TNF-α peptide for specific binding to mature human TNF-α,
   wherein the second TNF-α peptide is a peptide consisting of residues $Ala_{22}$-$Glu_{23}$-$Gly_{24}$-$Gln_{25}$-$Leu_{26}$-$Gln_{27}$-$Trp_{28}$-$Leu_{29}$-$Asn_{30}$-$Arg_{31}$-$Arg_{32}$-$Ala_{33}$-$Asn_{34}$-$Ala_{35}$-$Leu_{36}$-$Leu_{37}$-$Ala_{38}$-$Asn_{39}$-$Gly_{40}$ (peptide 307) of mature human TNF-α; and
   wherein the cell line has been isolated.

156. A cell line producing a single domain antibody or fragment thereof that specifically binds to mature human TNF-α,
   wherein when the antibody or fragment thereof binds mature human TNF-α, the induction of endothelial pro-coagulant activity is inhibited; and
   wherein the antibody or fragment thereof competitively inhibits sheep anti-sera raised against a TNF-α peptide for specific binding to mature human TNF-α,
   wherein the TNF-α peptide is a peptide consisting of residues $Val_1$-$Arg_2$-$Ser_3$-$Ser_4$-$Ser_5$-$Arg_6$-$Thr_7$-$Pro_8$-$Ser_9$-$Asp_{10}$-$Lys_{11}$-$Pro_{12}$-$Val_{13}$-$Ala_{14}$-$His_{15}$-$Val_{16}$-$Val_{17}$-$Ala_{18}$ (peptide 301) of mature human TNF-α; and
   wherein the antibody or fragment thereof competitively inhibits sheep anti-sera raised against a second TNF-α peptide for specific binding to mature human TNF-α,
   wherein the second TNF-α peptide is a peptide consisting of residues $Val_{13}$-$Ala_{14}$-$His_{15}$-$Val_{16}$-$Val_{17}$-$Ala_{18}$-$Asn_{19}$-$Pro_{20}$-$Gln_{21}$-$Ala_{22}$-$Glu_{23}$-$Gly_{24}$-$Gln_{25}$-$Leu_{26}$ (peptide 306) of mature human TNF-α; and
   wherein the cell line has been isolated.

157. The cell line according to claim 156, wherein the antibody is a monoclonal antibody.

158. The cell line according to claim 156, wherein the antibody or fragment thereof has no effect on cytotoxicity.

159. The cell line according to claim 158, wherein the antibody or fragment thereof enhances tumor regression.

160. The cell line according to claim 156, wherein the antibody or fragment thereof enhances tumor regression.

161. The cell line according to claim 156, wherein the antibody or fragment thereof has no effect on tumor receptor binding to TNF-α.

162. The cell line according to claim 156, where comparative binding specificity between the antibody or fragment thereof and the sheep anti-sera is determined by antibody-anti-sera competition assays in the presence of mature human TNF-α.

163. The cell line according to claim 162, wherein in the antibody-anti-sera competition assays the antibody is immobilized.

164. The cell line according to claim 162, wherein in the antibody-anti-sera competition assays the TNF-α is immobilized.

165. The cell line according to claim 162, wherein the antibody or fragment thereof has no effect on cytotoxicity.

166. The cell line according to claim 162, wherein the antibody or fragment thereof enhances tumor regression.

167. The cell line according to claim 162, wherein the antibody or fragment thereof has no effect on tumor receptor binding to TNF-α.

168. The cell line according to claim 156, wherein the antibody or fragment thereof does not competitively inhibit sheep anti-sera raised against an additional TNF -α peptide for specific binding to mature human TNF-α,
   wherein the additional TNF-α peptide is a peptide consisting of residues $Ala_{111}$-$Lys_{112}$-$Pro_{113}$-$Trp_{114}$-$Tyr_{115}$-$Glu_{116}$-$Pro_{117}$-$Ile_{118}$-$Tyr_{119}$-$Leu_{120}$ (peptide 275) of mature human TNF-α.

169. The cell line according to claim 156, wherein the antibody or fragment thereof does not competitively inhibit sheep anti-sera raised against an additional TNF -α peptide for specific binding to mature human TNF-α,
   wherein the additional TNF-α peptide is a peptide consisting of residues $Ala_{22}$-$Glu_{23}$-$Gly_{24}$-$Gln_{25}$-$Leu_{26}$-$Gln_{27}$-$Trp_{28}$-$Leu_{29}$-$Asn_{30}$-$Arg_{31}$-$Arg_{32}$-$Ala_{33}$-$Asn_{34}$-$Ala_{35}$-$Leu_{36}$-$Leu_{37}$-$Ala_{38}$-$Asn_{39}$-$Gly_{40}$ (peptide 307) of mature human TNF-α.

170. The cell line according to claim 156, wherein the antibody competitively inhibits sheep anti-sera raised against an additional TNF-α peptide for specific binding to mature human TNF-α, wherein the additional TNF-α peptide is a peptide consisting of residues $Leu_{132}$-$Ser_{133}$-$Ala_{134}$-$Glu_{135}$-$Ile_{136}$-$Asn_{137}$-$Arg_{138}$-$Pro_{135}$-$Asp_{140}$-$Tyr_{141}$-$Leu_{142}$-$Asp_{143}$-$Phe_{144}$-$Ala_{145}$-$Glu_{146}$-$Ser_{147}$-$Gly_{148}$-$Gln_{149}$-$Val_{150}$ (peptide 305) of mature human TNF-α.

171. The cell line according to any one of claims 156-170, wherein the antibody is a humanized antibody.

172. The cell line according to any one of claims 156-170, wherein the antibody is a chimeric antibody.

173. The cell line according to any one of claims 156-170, wherein the antibody is a human antibody.

174. A composition comprising a cell line producing a single domain antibody or fragment thereof that specifically binds to mature human TNF-α, wherein when the antibody or fragment thereof binds mature human TNF-α, the induction of endothelial procoagulant activity is inhibited; and wherein the antibody or fragment thereof competitively inhibits sheep anti-sera raised against a TNF-α peptide for specific binding to mature human TNF-α, wherein the TNF-α peptide is a peptide consisting of residues $Val_1$-$Arg_2$-$Ser_3$-$Ser_4$-$Ser_5$-$Arg_6$-$Thr_7$-$Pro_8$-$Ser_9$-$Asp_{10}$-$Lys_{11}$-$Pro_{12}$-$Val_{13}$-$Ala_{14}$-$His_{15}$-$Val_{16}$-$Val_{17}$-$Ala_{18}$ (peptide 301) of mature human TNF-α; and wherein the antibody or fragment thereof competitively inhibits sheep anti-sera raised against a second TNF-α peptide for specific binding to mature human TNF-α, wherein the second TNF-α peptide is a peptide consisting of residues $Val_{13}$-$Ala_{14}$-$His_{15}$-$Val_{16}$-$Val_{17}$-$Ala_{18}$-$Asn_{19}$-$Pro_{20}$-$Gln_{21}$-$Ala_{22}$-$Glu_{23}$-$Gly_{24}$-$Gln_{25}$-$Leu_{26}$ (peptide 306) of mature human TNF-α; and wherein the cell line has been isolated.

175. The cell line according to claim 2, wherein the antibody is MAb 1 (ECACC Accession No. 89080301).

176. The composition according to claim 25, wherein the antibody is MAb 1 (ECACC Accession No. 89080301).

177. The cell line according to claim 2, wherein the antibody is MAb 47 (ECACC Accession No. 89121402).

178. The composition according to claim 25, wherein the antibody is MAb 47 (ECACC Accession No. 89121402).

179. The cell line according to claim 2, wherein the antibody is MAb 54 (ECACC Accession No. 89083103).

180. The composition according to claim 25, wherein the antibody is MAb 54 (ECACC Accession No. 89083103).

181. The cell line according to claim 68, wherein the antibody is MAb 32 (ECACC Accession No. 89090302).

182. The composition according to claim 86, wherein the antibody is MAb 32 (ECACC Accession No. 89080302).

183. The cell line according to claim 36, wherein the antibody is MAb 53 (ECACC Accession No. 90012433).

184. The composition according to claim 46, wherein the antibody is MAb 53 (ECACC Accession No. 90012433).

185. The cell line according to claim 47, wherein the antibody is MAb 42 (ECACC Accession No. 89080304).

186. The composition according to claim 67, wherein the antibody is MAb 42 (ECACC Accession No. 89080304).

187. The cell line according to claim 2, wherein the antibody is MAb 21 (ECACC Accession No. 90012432).

188. The composition according to claim 25, wherein the antibody is MAb 21 (ECACC Accession No. 90012432).

\* \* \* \* \*

Disclaimer

7,553,641 - Deborah A. Rathjen, Flagstaff Hill (AU); Roger Aston, Gloucester (GB). TUMOUR NECROSIS FACTOR BINDING LIGANDS. Patent Dated June 30, 2009. Disclaimer Dated June 24, 2010 by the Assignee, Arana Therapeutics Limited.

The term of this patent shall not extend beyond the expiration date of Patent No. 7,605,233.

*(Official Gazette, July 20, 2010)*